(12) United States Patent
Fushihara et al.

(10) Patent No.: US 6,576,627 B1
(45) Date of Patent: Jun. 10, 2003

(54) PHOSPHONIC ACID DERIVATIVES HAVING CARBOXYPEPTIDASE B INHIBITORY ACTIVITY

(75) Inventors: Kenichi Fushihara, Ayase (JP); Chika Kikuchi, Yokohama (JP); Tetsuya Matsushima, Kawasaki (JP); Kenichi Kanemoto, Yokohama (JP); Eriko Satoh, Kawasaki (JP); Takehiro Yamamoto, Hachiouji (JP); Kokichi Suzuki, Yokohama (JP)

(73) Assignee: Meiji Seika Kaisha Ltd., Tokyo (JP)

(*) Notice: Subject to any disclaimer, the term of this patent is extended or adjusted under 35 U.S.C. 154(b) by 0 days.

(21) Appl. No.: 09/926,125

(22) PCT Filed: Sep. 13, 2000

(86) PCT No.: PCT/JP00/06248

§ 371 (c)(1),
(2), (4) Date: Nov. 13, 2001

(87) PCT Pub. No.: WO01/19836

PCT Pub. Date: Mar. 22, 2001

(30) Foreign Application Priority Data

Sep. 14, 1999 (JP) .............................. 11-260993
Mar. 24, 2000 (JP) ........................ 2000-084145

(51) Int. Cl.$^7$ .......................... A61K 31/662; C07F 9/30
(52) U.S. Cl. .......................... 514/119; 558/170; 562/15
(58) Field of Search .................... 558/170; 562/15; 514/119

(56) References Cited

U.S. PATENT DOCUMENTS

| | | | |
|---|---|---|---|
| 4,452,791 A | 6/1984 | Ryono et al. | 424/200 |
| 4,560,680 A | 12/1985 | Ryono et al. | 514/82 |
| 4,616,005 A | 10/1986 | Karanewsky et al. | 514/80 |
| 5,030,732 A | * 7/1991 | Morita et al. | |
| 6,121,252 A | 9/2000 | Jackson et al. | 514/89 |
| 6,444,657 B1 | * 9/2002 | Slusher et al. | 514/114 |

FOREIGN PATENT DOCUMENTS

| | | |
|---|---|---|
| DE | 212739 | 8/1984 |
| EP | 282219 | * 9/1988 |
| WO | 00/66557 | 11/1990 |
| WO | 99/08521 | 2/1999 |
| WO | 99/50272 | 10/1999 |
| WO | 00/66152 | 11/2000 |
| WO | WO-00/66550 | * 11/2000 |

OTHER PUBLICATIONS

Bajzar et al., Journal of Biological Chemistry, vol. 270, No. 24, 14477–14484 (1995).
Redlitz et al., J. Clin. Invest., vol. 96, 2534–2538 (1995).
Bajzar et al., Jouranl of Biological Chemistry, vol. 271, No. 28, 16603–16608 (1996).
Mosnier et al., Thromb. Haemost., vol. 80, 829–835 (1998).
Redlitz et al., Circulation, 1328–1330 (1996).
McKay et al., Biochemistry, vol. 17, No. 3, 401–405 (1978).
McKay et al., Archives of Biochemistry and Biophysics, vol. 197, No. 2, 487–492 (1979).
Ondetti et al., Biochemistry, vol. 18, No. 8, 1427–1430 (1979).
Cheng et al., Tetrahedron Lett., vol. 32, No. 49, 7333–7336 (1991).
Soroka et al., Synthesis, 370–372 (1988).
Natchev, Liebigs. Ann. Chem., 861–867 (1988).
Baylis et al., J. Chem. Soc. Perkin Trans. 1, 2845–2853 (1984).
Morgan et al., J. Am. Chem. Soc., vol. 113, No. 1, 297–307 (1991).
Campbell et al., J. Org. Chem., vol. 59, No. 3, 658–660 (1994).
Qiao et al., J. Med. Chem., vol. 41, No. 18, 3303–3306 (1998).
Yamashita et al., Synthesis, 556–557 (1986).
Karanewsky et al., J. Med. Chem., vol. 33, No. 5, 1459–1469 (1990).
Karanewsky et al., Tetrahedron Lett., vol. 27, No. 16, 1751–1754 (1986).

(List continued on next page.)

Primary Examiner—Fiona T. Powers
(74) Attorney, Agent, or Firm—Greenblum & Bernstein, P.L.C.

(57) ABSTRACT

A compound represented by the following general formula (I) and a pharmacologically acceptable salt thereof:

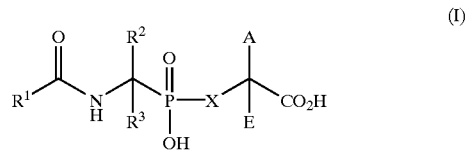

wherein $R^1$ represents hydrogen atom, an alkyl group, a substituted alkyl group and the like; $R^2$ and $R^3$ represent hydrogen atom, an alkyl group, a substituted alkyl group, an alkoxyl group and the like; X represents —$CH_2$—, —O—, or —NH—; A represents the following group (II):

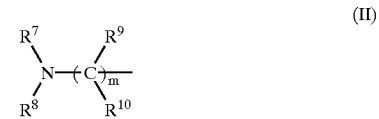

[in which $R^7$ and $R^8$ represent hydrogen atom, an alkyl group, an acyl group, an alkoxycarbonyl group and the like; $R^9$ and $R^{10}$ represents hydrogen atom, a halogen atom, hydroxyl group, phenyl group, an alkyl group and the like] and the like; and E represents hydrogen atom and the like, which has inhibitory activity against carboxypeptidase B and is useful for therapeutic and/or preventive treatment of a thrombotic disease.

20 Claims, No Drawings

OTHER PUBLICATIONS

Zhang et al., Tetrahedron Lett., vol. 37, No. 31, 5457–5460 (1996).

Cao et al., Tetrahedron Lett., vol. 37, No. 34, 6073–6076 (1996).

Chackalamannil et al., Bioorganic & Medical Chemistry Letters, vol. 6, No. 11, 1257–1260 (1996).

Allen et al., J. Med. Chem., vol. 32, No. 7, 1652–1661 (1989).

Dorff et al., Tetrahedron Lett., vol. 39, 3375–3378 (1998).

Boyd et al., Tetrahedron Lett., vol. 31, No. 20, 2933–2936 (1990).

Neustadt et al., J. Med. Chem., vol. 37, No. 15, 246–2476 (1994).

McKittrick et al., Bioorganic & Medical Chemistry Letters, vol. 6, No. 14, 1629–1634 (1996).

Hanson et al., Biochemistry, vol. 28, No. 15, 6294–6305 (1989).

Aketa et al., Chem. Pharm. Bull., vol. 24, No. 4, 621–631 (1976).

Seebach et al., Helv. Chem. Acta., Col. 71, 155–167 (1988).

Marco et al., Tetrahedron, vol. 55, 7625–7644 (1999).

Bernatowicz et al., Tetrahedron Lett., 3389 (1993).

Hosaka et al., Thromb. Haemost., vol. 79, 371–377 (1998).

Maffre–Lafron et al., "A Rational Approach to the Synthesis of Phosphonamidate Peptides", Letters in Peptide Science, Escom.

Fricker et al., Biochem. Biophys. Res. Commun. (1983), 111(3), 00.994–1000, accompanied by an English abstract.

Mackin et al, Endrocrinology, vol. 120, No. 2, pp. 457–468, 1987.

Neustadt et al., J. Med. Chem., vol. 37, No. 15, 2461–2476 (1994).

Maffre–Lafron et al., "A Rational Approach to the Synthesis of Phosphonamidate Peptides", Letters in Peptide Science, Escom Science Publishers, NL, vol. 1, No. 1, 1994, pp. 51–55.

* cited by examiner

PHOSPHONIC ACID DERIVATIVES HAVING CARBOXYPEPTIDASE B INHIBITORY ACTIVITY

TECHNICAL FIELD

The present invention relates to phosphonic acid derivatives having inhibitory activity against carboxypeptidase B, and to pharmaceutical compositions which comprise at least one of said derivative as an active ingredient and are useful for therapeutic and preventive treatment of various thrombosis, diseases caused by a vascular disorder, and organ disorders resulting from reduction of fibrinolysis.

BACKGROUND ART

Numbers of patients suffering from circulatory diseases have been increasing due to growth of aged population and changes in social circumstances. Among the aforementioned diseases, those caused by thrombus such as cerebral infarction and myocardial infarction show an increasing tendency. For these diseases, various antithrombotic treatments have been clinically applied.

The antithrombotic treatments are classified basically into anticoagulant, antiplatelet, and thrombolytic treatments. Among them, the thrombolytic treatments involve the lysis of formed thrombus, per se. In that sense, they are considered as more reasonable remedies for therapeutic treatment of thrombosis than the anticoagulant treatments which prevent generation and development of secondary thrombus. At present, enzymatic agents such as urokinase and plasminogen activator have been clinically used as thrombolytic agents, and their clinical effectiveness has been recognized as one of therapeutic treatments for patients suffering from thrombosis.

Detailed mechanisms as to fibrinolysis have been being revealed with the progress of biochemical researches. A factor, which was reported as a fibrinogenolysis-inhibitory factor TAFI (thrombin activatable fibrinolysis inhibitor factor) activated by stimulation of coagulation, was revealed to be identical to plasma carboxypeptidase B (J. Biol. Chem., 14477(1995)). It was elucidated that plasma carboxypeptidase B inhibits fibrinolysis by interrupting plasminogen, which is a fibrinolytic enzyme mainly acting in the lysis of thrombus (fibrin), from binding to thrombi (J. Clin. Invest., 2534(1995)., J. Biol. Chem., 16603(1996), Thromb. Haemost., 829(1998), Circulation, 1328(1996)). Accordingly, plasma carboxypeptidase B inhibitors are expected to be used as agents for therapeutic and preventive treatments of various thromboses, which are antithrombotic agents based on enhancement of the lysis of thrombi.

As substances inhibiting pancreatic carboxypeptidase B, GEMSA (Biochemistry, 401(1978), Arch. Biochem. Biophys., 487(1979)), SQ24798 (Biochemistry, 1427 (1979)) and the like have been known so far.

Plasminogen activators and the like, which have been clinically used as thrombolytic agents at present, are not fully satisfactory from a clinical therapeutic viewpoint as their low safety such as hemorrhagic adverse effects and poor pharmacokinetics such as a short-half-life, although their thrombolytic activities in an acute stage after thrombus formation are reliable.

DISCLOSURE OF THE INVENTION

In order to provide a thrombolytic agent having higher safety, the inventors of the present invention conducted researches to find a compound having inhibitory activity against plasma carboxypeptidase B. As a result, they found that phosphonic acid derivatives have potent inhibitory activity against carboxypeptidase B.

The present invention thus provide a compound represented by the following general formula (I) or a pharmacologically acceptable salt thereof, or a hydrate thereof or a solvate thereof:

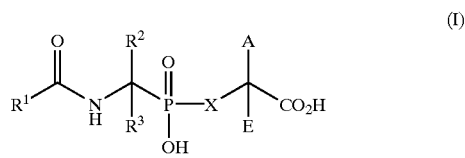

wherein $R^1$ represents hydrogen atom, an alkyl group, a substituted alkyl group, an alkoxyl group, a substituted alkoxyl group, amino group, a substituted amino group, a carbocyclic group, a substituted carbocyclic group, a heterocyclic group, or a substituted heterocyclic group;

$R^2$ and $R^3$ may be the same or different and independently represent hydrogen atom, an alkyl group, a substituted alkyl group, an alkoxyl group, a substituted alkoxyl group, amino group, a substituted amino group, a carbocyclic group, a substituted carbocyclic group, a heterocyclic group, or a substituted heterocyclic group, or $R^2$ and $R^3$ may form a 5 to 7 membered carbon ring together with the carbon atom to which they bind;

X represents —$CH_2$—, —O—, or —NH—;

A represents a group of the following formula (II):

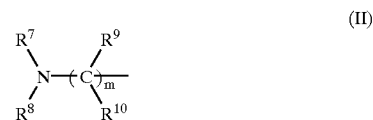

[in which $R^7$ and $R^8$ may be the same or different and independently represent hydrogen atom, an alkyl group, an acyl group, an alkoxycarbonyl group, an aryloxycarbonyl group, carbamoyl group, a substituted carbamoyl group, or amidino group;

$R^9$ and $R^{10}$ may be the same or different and independently represent hydrogen atom, a halogen atom, hydroxyl group, phenyl group, an alkyl group, an alkoxyl group, an aryloxy group, an acyl group, carboxyl group, an alkoxycarbonyl group, carbamoyl group, a substituted carbamoyl group, amino group, a substituted amino group, nitro group, —$SR^{11}$ group ($R^{11}$ represents an alkyl group, phenyl group, or a substituted phenyl group), —$SOR^{12}$ group ($R^{12}$ represents an alkyl group, phenyl group, a substituted phenyl group, an alkoxyl group, an aryloxy group, amino group, or a substituted amino group), or —$SO_2R^{13}$ group ($R^{13}$ represents an alkyl group, phenyl group, a substituted phenyl group, an alkoxyl group, an aryloxy group, amino group, or a substituted amino group);

m represents an integer of from 1 to 8; and

—$(C)_m$— represents a saturated or unsaturated carbon chain], or

A represents a group of the following formula (III):

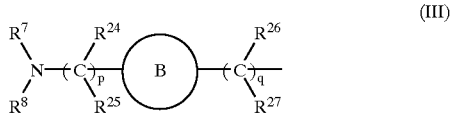

(III)

[in which

R$^7$ and R$^8$ may be the same or different and independently represent hydrogen atom, an alkyl group, an acyl group, an alkoxycarbonyl group, an aryloxycarbonyl group, carbamoyl group, a substituted carbamoyl group, or amidino group;

R$^{24}$, R$^{25}$, R$^{26}$ and R$^{27}$ may be the same or different and independently represent hydrogen atom, a halogen atom, hydroxyl group, an alkyl group, amino group, or a substituted amino group;

p and q independently represent an integer of from 0 to 2; —(C)$_p$— and —(C)$_q$— independently represent single bond, or a saturated or unsaturated carbon chain; and B represents a carbocyclic group, a substituted carbocyclic group, a heterocyclic group, or a substituted heterocyclic group], or A represents a group of the following formula (IV):

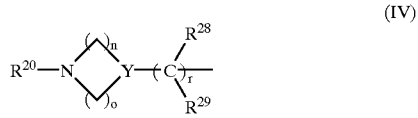

(IV)

[in which

R$^{20}$ represents hydrogen atom, an alkyl group, an acyl group, an alkoxycarbonyl group, carbamoyl group, an alkylcarbamoyl group, or amidino group; R$^{28}$ and R$^{29}$ may be the same or different and independently represent hydrogen atom, a halogen atom, hydroxyl group, an alkyl group, amino group, or an alkylamino group;

n and o independently represent an integer of from 0 to 5;

r represents an integer of from 0 to 4;

—(C)$_r$— independently represents single bond, or a saturated or unsaturated carbon chain; and Y represents CH or nitrogen atom], or A represents a group of the following formula (XI):

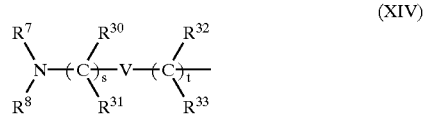

(XIV)

[in which

R$^7$ and R$^8$ may be the same or different and independently represent hydrogen atom, an alkyl group, an acyl group, an alkoxycarbonyl group, an aryloxycarbonyl group, carbamoyl group, a substituted carbamoyl group, or amidino group;

R$^{30}$, R$^{31}$, R$^{32}$ and R$^{33}$ may be the same or different and independently represent hydrogen atom, a halogen atom, hydroxyl group, an alkyl group, oxo group, amino group, or an alkylamino group;

s represents an integer of from 0 to 3;

t represents an integer of from 1 to 3;

—(C)$_s$— and —(C)$_t$— independently represent single bond, or a saturated or unsaturated carbon chain; and V represents —O— or —NH—]; and, E represents hydrogen atom, or —CH$_2$CH$_2$— to form together with A a piperidine ring group or a N-substituted piperidine ring group.

The present invention also provides a medicament which comprises as an active ingredient a substance selected from the group consisting of the compound represented by the aforementioned general formula (I) and a pharmacologically acceptable salt thereof, and a hydrate thereof and a solvate thereof. According to a preferred embodiment, there is provided the aforementioned medicament in the form of a pharmaceutical composition which comprises the aforementioned substance as an active ingredient together with a pharmacologically acceptable carrier. These medicaments are useful for therapeutic and/or preventive treatment of thrombotic diseases.

The present invention also provides an inhibitor against carboxypeptidase B which comprises as an active ingredient the substance selected from the group consisting of the compound represented by the aforementioned general formula (I) and a pharmacologically acceptable salt thereof, and a hydrate thereof and a solvate thereof.

The present invention further provides a use of the substance selected from the group consisting of the compound represented by the aforementioned general formula (I) and a pharmacologically acceptable salt thereof, and a hydrate thereof and a solvate thereof for the manufacture of the aforementioned medicament; and a method for therapeutic and/or preventive treatment of thrombotic diseases which comprises the step of administering to a mammal including a human a therapeutically and/or preventively effective amount of the substance selected from the group consisting of the compound represented by the aforementioned general formula (I) and a pharmacologically acceptable salt thereof, and a hydrate thereof and a solvate thereof.

BEST MODE FOR CARRYING OUT THE INVENTION

In the specification, the alkyl group or an alkyl which constitutes a part of a substituent (e.g., alkoxyl groups) means a $C_{1-10}$ alkyl group unless otherwise specifically mentioned, which encompasses straight chain alkyl groups including methyl group, ethyl group, n-propyl group, n-butyl group, n-pentyl group, n-hexyl group, n-heptyl group, n-octyl group and the like as typical examples; branched chain alkyl groups such as isopropyl group, s-butyl group, t-butyl group, 2-pentyl group, 3-pentyl group, and 1,1-dimethylpropyl group; cyclic alkyl groups such as cyclopropyl group, cyclobutyl group, cyclopentyl group, cyclohexyl group, and cycloheptyl group; and alkyl groups as combinations of a straight or branched chain alkyl group and a cyclic alkyl group, such as cyclopropylmethyl group, cyclopropylethyl group, and cyclobutylmethyl group. In the groups containing an alkenyl moiety, the number of double bonds contained in the alkenyl moiety is not particularly limited. The alkenyl moiety may be any of a straight chain, a branched chain, cyclic moiety, or a combination thereof unless otherwise specifically mentioned, and is preferably straight chain or branched chain. A double bond contained in the alkenyl moiety may be in either Z- or E-configuration.

In the specification, the acyl group or an acyl group which constitutes a part of a substituent means a functional group selected from the group consisting of formyl group, straight chain or branched chain $C_{2-10}$ alkylcarbonyl groups, $C_{7-15}$ aralkylcarbonyl groups, and $C_{4-7}$ cycloalkycarbonyl groups. Examples include, for example, formyl group, acetyl group, propionyl group, butenyl group, benzoyl group, pivaloyl group and the like, and is preferably acetyl group.

The halogen atom means fluorine atom, chlorine atom, bromine atom, or iodine atom, and preferably fluorine atom or chlorine atom.

In the specification, the aryl group or an aryl group which constitutes a part of a substituent means, unless otherwise specifically mentioned, a 6 to 14-membered (monocyclic to tricyclic, preferably monocyclic or bicyclic) aromatic ring group such as phenyl, 1-naphthyl, 2-naphthyl, biphenyl, and 2-anthrylnaphthyl.

A heterring means a 5 to 14-membered, preferably 5 to 10-membered, (monocyclic to tricyclic, preferably monocyclic or bicyclic) heterring which contains 1 to 4, preferably 1 to 3, heteroatoms of 1 or 2 kinds selected from oxygen atom, nitrogen atom, and sulfur atom other than carbon atom. Examples include, for example, furan ring, pyrrole ring, pyrrolidine ring, pyrazole ring, imidazole ring, oxazole ring, thiazole ring, triazole ring, pyrane ring, pyridine ring, piperidine ring, dioxane ring, morpholine ring, pyridazine ring, pyrimidine ring, pyrazine ring, piperazine ring, triazine ring and the like, and preferably imidazole ring, triazole ring, pyridine ring, piperidine ring, pyrimidine ring, pyrazine ring, piperazine ring and the like. The heterocyclic group or a heterocyclic group which constitutes a part of the substituent means a residue of the aforementioned heterring.

A carbon ring preferably means a saturated or unsaturated 5 to 7-membered ring. Examples include, for example, cyclopropane ring, cyclobutane ring, cyclopentane ring, cyclopentyl ring, cyclohexane ring, cycloheptane ring, benzene ring and the like.

When m represents an integer of 2 or more, the description:

shows an alkylene group which consists of "m" groups of the methylene defined in the parenthesis bound to each other in a chain, and respective "m" groups of $R^9$ and $R^{10}$, each existing one to every "m" groups of the methylene, are independent and may be the same or different. The aforementioned description should not be interpreted as mere repetition of "m" groups of the same methylene. The other alkylene groups defined by p, q, r, s, or t are described in the same manner.

In formula (I), the alkyl group represented by $R^1$, $R^2$, or $R^3$, or an alkyl group existing on the substituent represented by $R^1$, $R^2$, or $R^3$ is preferably a $C_{1-8}$ alkyl group, more preferably a $C_{1-6}$ alkyl group, and further preferably a $C_{1-4}$ alkyl group. When the alkyl group represented by $R^1$, $R^2$, or $R^3$ is a cyclic alkyl group, the group may preferably be a $C_{3-7}$ cycloalkyl group. Examples include, for example, cyclopropyl, cyclobutyl, cyclohexyl, cycloheptyl and the like.

One or more hydrogen atoms on the alkyl group represented by $R^1$, $R^2$, or $R^3$ may be substituted. Examples of the substituent include hydroxyl group, phenyl group, a substituted phenyl group, a halogen atom, an alkoxyl group, a substituted alkoxyl group, an acyl group, carboxyl group, an alkoxycarbonyl group, an aryloxycarbonyl group, carbamoyl group, a substituted carbamoyl group, amino group, a substituted amino group, nitro group, oxo group, a carbocyclic group, a substituted carbocyclic group, a heterocyclic group, a substituted heterocyclic group, —$SR^4$ group ($R^4$ represents an alkyl group, phenyl group, or a substituted phenyl group (examples of the substituent include a $C_{1-4}$ alkyl group, a $C_{1-4}$ alkoxyl groups and the like)), —$SOR^5$ groups ($R^5$ represents an alkyl group, phenyl group, a substituted phenyl group (examples of the substituent include a $C_{1-4}$ alkyl group, a $C_{1-4}$ alkoxyl group and the like), an alkoxyl group, amino group, or an alkylamino group), —$SO_2R^6$ group ($R^6$ represents an alkyl group, phenyl group, a substituted phenyl group (examples of the substituent include a $C_{1-4}$ alkyl group, a $C_{1-4}$ alkoxyl group and the like), an alkoxyl group, amino group, or an alkylamino group) and the like. Preferred substituents include hydroxyl group, phenyl group, a substituted phenyl group (substituted with hydroxyl group, a halogen atom, an alkoxyl group, an amino group), a halogen atom, an alkoxyl group, an acyl group (e.g., acetyl group), carboxyl group, amino group, oxo group, and a heterocyclic group. The position of the substituent on the alkyl group is not particularly limited. When 2 or more substituents exist on the alkyl group, they may be the same or different.

In formula (I), the alkoxyl group represented by $R^1$, $R^2$, or $R^3$, or an alkoxyl group existing on the substituent represented by $R^1$, $R^2$, or $R^3$ is preferably a $C_{1-8}$ alkoxyl group, more preferably a $C_{1-6}$ alkoxyl group, and further preferably a $C_{1-5}$ alkoxyl group.

One or more hydrogen atoms on the alkoxyl group represented by $R^1$, $R^2$, or $R^3$ may be substituted. Examples of the substituent include hydroxyl group, phenyl group, a substituted phenyl group, a halogen atom, an alkoxyl group, a substituted alkoxyl group, an acyl group, carboxyl group, an alkoxycarbonyl group, an aryloxycarbonyl group, carbamoyl group, a substituted carbamoyl group, amino group, a substituted amino group, —$SR^{21}$ group ($R^{21}$ represents an alkyl group, phenyl group, or a substituted phenyl group (examples of the substituent include a $C_{1-4}$ alkyl group, a $C_{1-4}$ alkoxyl group and the like)), —$SOR^{22}$ group ($R^{22}$ represents an alkyl group, phenyl group, a substituted phenyl group (examples of the substituent include a $C_{1-4}$ alkyl group, a $C_{1-4}$ alkoxyl group and the like), an alkoxyl group, amino group, or an alkylamino group), —$SO_2R^{23}$ group ($R^{23}$ represents an alkyl group, phenyl group, a substituted phenyl group (examples of the substituent include a $C_{1-4}$ alkyl group, a $C_{1-4}$ alkoxyl group and the like), an alkoxyl group, amino group, or an alkylamino group) and the like. A preferred substituent includes phenyl group. The position of the substituent on the alkoxyl group is not particularly limited. When 2 or more substituents exist on the alkoxyl group, they may be the same or different.

In formula (I), one or two hydrogen atoms of the amino group represented by $R^1$, $R^2$, or $R^3$ may be substituted. When two hydrogen atoms are substituted, the substituents may be the same or different. Examples of the substituent include an alkyl group, an alkenyl group, an acyl group, an acylalkyl group, an alkoxycarbonyl group, an alkoxycarbonylalkyl group, an arylalkyloxycarbonyl group, an alkylsulfonyl group, an alkylsulfonylalkyl group, an arylsulfonyl groups, an arylsulfonylalkyl group and the like. Examples of the substituted amino group include methylamino group, ethylamino group, n-propylamino group, isopropylamino group, allylamino group, phenylamino group, benzylamino group, cyclohexylamino group, dimethylamino group, allylmethylamino group, allylcyclohexylamino group, formylamino group, acetylamino group, benzoylamino group, pivaloylamino group, acetylmethylamino group, phthaloylamino group, methoxycarbonylamino group, isopropoxycarbonylamino group, methoxycarbonylmethylamino group, benzyloxycarbonylamino group, methylsulfonylamino group, phenylsulfonylamino group, benzenesulfonylamino group, and methyl(methylsulfonyl)amino group. Methylamino group, allylamino group, acetylamino group, methylsulfonylamino group, dimethylamino group, allylmethylamino group, or benzoylamino group is preferred.

In formula (I), the carbon ring represented by $R^1$, $R^2$, or $R^3$, or the carbon ring represented by $R^2$ and $R^3$ together with the carbon atom to which they bind may be substituted with a halogen atom, an alkyl group, an alkoxyl group, oxo group, an acyl group, carbamoyl group, amino group, or a substituted amino group. A specific example includes 1-(3,5-dioxo)cyclohexyl group.

In formula (I), the heteroring represented by $R^1$, $R^2$, or $R^3$ may be substituted with an alkyl group, an alkoxyl groups, oxo group, an acyl group, carbamoyl group, amino group, or a substituted amino group.

In formula (I), the group or atom represented by X is preferably oxygen atom.

In group (II), group (III), and group (XIV) represented by A in formula (I), examples of the group represented by $R^7$ or $R^8$ include hydrogen atom, an alkyl group, an acyl group, an alkoxycarbonyl group (e.g., methoxycarbonyl group, ethoxycarbonyl group, isopropoxycarbonyl group, t-butoxycarbonyl group and the like), an aryloxycarbonyl group (e.g., phenoxycarbonyl group and the like), carbamoyl group, an alkylcarbamoyl group (e.g., methylcarbamoyl group, ethylcarbamoyl group, N,N-dimethylcarbamoyl group, N,N'-diethylcarbamoyl group and the like), an arylalkylcarbamoyl group (e.g., benzylcarbamoyl group and the like), and amidino group. Hydrogen atom, methyl group, ethyl group, formyl group, or amidino group is preferred, and hydrogen atom or methyl group is more preferred.

In group (II) represented by A in formula (I), examples of the group represented by $R^9$ or $R^{10}$ include hydrogen atom, a halogen atom, hydroxyl group, phenyl group, an alkyl group, an alkoxyl group, an aryloxy group (e.g., phenoxy group and the like), an acyl group, carboxyl group, an alkoxycarbonyl group (e.g., methoxycarbonyl group, isopropoxycarbonyl group and the like), carbamoyl group, an alkylcarbamoyl group (e.g., methylcarbamoyl group, N,N-dimethylcarbamoyl group, and the like), an alkenylcarbamoyl group (e.g., allylcarbamoyl group and the like), amino group, an alkylamino groups (e.g., methylamino group, ethylamino group, dimethylamino group and the like), an alkenylamino group (e.g., allylmethylamino group and the like), an acylamino group (e.g., acetylamino group, formylamino group, benzoylamino group and the like), an acylalkylamino group (e.g., acetylmethylamino group and the like), an alkoxycarbonylamino group (e.g., methoxycarbonylamino group and the like), nitro group, —$SR^{11}$ group {$R^{11}$ represents an alkyl group, phenyl group or a substituted phenyl group (examples of the substituent include $C_{1-4}$ alkyl groups, $C_{1-4}$ alkoxyl groups and the like)}, —$SOR^{12}$ group {$R^{12}$ represents an alkyl group, phenyl group, a substituted phenyl group (examples of the substituent include $C_{1-4}$ alkyl groups, $C_{1-4}$ alkoxyl groups and the like), an alkoxyl group (e.g., methoxy group, n-propoxy group and the like), an aryloxy group (e.g., phenoxy group and the like), amino group, or an alkylamino group (e.g., methylamino group, dimethylamino group and the like)}, and —$SO_2R^{13}$ group {$R^{13}$ represents an alkyl group, phenyl group, a substituted phenyl group (examples of the substituent include a $C_{1-4}$ alkyl group, a $C_{1-4}$ alkoxyl group and the like), an alkoxyl group (e.g., methoxy group, n-propoxy group and the like), an aryloxy group (e.g., phenoxy group and the like), amino group, or an alkylamino group (e.g., methylamino group, dimethylamino group and the like)}. Hydrogen atom, fluorine atom, chlorine atom, methyl group, ethyl group, or acetyl group is preferred, and hydrogen atom is more preferred.

In group (II) represented by A in formula (I), the integer represented by m is preferably from 2 to 6, and more preferably 4 or 5.

In group (III) represented by A in formula (I), examples of the group represented by $R^{24}$, $R^{25}$, $R^{26}$, or $R^{27}$ include hydrogen atom, a halogen atom, hydroxyl group, an alkyl group, amino group, and a substituted amino group (examples of the substituent include $C_{1-4}$ alkyl groups and the like).

In group (III) represented by A in formula (I), the carbon ring represented by B is preferably cyclohexane ring or benzene ring. One or more hydrogen atoms on the carbon ring represented by B may be substituted. Examples of the substituent include hydroxyl group, a halogen atom, phenyl group, an alkyl group, an alkoxyl group, an aryloxy group (e.g., phenoxy group and the like), an acyl group (e.g., formyl group, acetyl group, benzoyl group and the like), carboxyl group, an alkoxycarbonyl group, carbamoyl group, an alkylcarbamoyl group (e.g., methylcarbamoyl group, N,N-dimethylcarbamoyl group and the like), an alkenylcarbamoyl group (e.g., allylcarbamoyl group and the like), amino group, an alkylamino group (e.g., methylamino group, ethylamino group, dimethylamino group and the like), an alkenylamino group (e.g., allylmethylamino group and the like), an acylamino group (e.g., acetylamino group, formylamino group, benzoylamino group and the like), an acylalkylamino group (e.g., acetylmethylamino group and the like), an alkoxycarbonylamino group (e.g., methoxycarbonylamino group and the like), nitro group, —$SR^{14}$ group {$R^{14}$ represents an alkyl group, phenyl group, or a substituted phenyl group (examples of the substituent include a $C_{1-4}$ alkyl group, a $C_{1-4}$ alkoxyl group and the like)}, —$SOR^{15}$ group {$R^{15}$ represents an alkyl group, phenyl group, or a substituted phenyl group (examples of the substituent include a $C_{1-4}$ alkyl group, a $C_{1-4}$ alkoxyl group and the like), an alkoxyl group, amino group, or an alkylamino group (e.g., methylamino group, dimethylamino group and the like)} and —$SO_2R^{16}$ group {$R^{16}$ represents an alkyl group, phenyl group, or a substituted phenyl group (examples of the substituent include a $C_{1-4}$ alkyl group, a $C_{1-4}$ alkoxyl group and the like), an alkoxyl group, amino group, or an alkylamino group (e.g., methylamino group, dimethylamino group and the like)}. Hydrogen atom, fluorine atom, chlorine atom, methyl group, ethyl group, acetyl group, carbamoyl group, carboxyl group, or nitro group is preferred.

In group (III) represented by A in formula (I), the heteroring represented by B is preferably imidazole ring, triazole ring, pyridine ring, piperidine ring, pyrimidine ring, pyrazine ring, or piperazine ring. One or more hydrogen atoms on the heteroring represented by B may be substituted. Examples of the substituent include hydroxyl group, a halogen atom, phenyl group, an alkyl group, an alkoxyl group, an aryloxy group (e.g., phenoxy group and the like), an acyl group (e.g., formyl group, acetyl group, benzoyl group and the like), carboxyl group, an alkoxycarbonyl group, carbamoyl group, an alkylcarbamoyl group (e.g., methylcarbamoyl group, N,N-dimethylcarbamoyl group and the like), an alkenylcarbamoyl group (e.g., allylcarbamoyl group and the like), amino group, an alkylamino group (e.g., methylamino group, ethylamino group, dimethylamino group and, the like), an acylamino group (e.g., acetylamino group, formylamino group, benzoylamino group and the like), an acylalkylamino group (e.g., acetylmethylamino group and the like), an alkoxycarbonylamino group (e.g., methoxycarbonylamino group and the like), nitro group, —$SR^{17}$ group {$R^{17}$ represents an alkyl group, phenyl group, or a substituted phenyl group (examples of the substituent include a $C_{1-4}$ alkyl group, a $C_{1-4}$ alkoxyl group and the like)}, —$SOR^{18}$ group {$R^{18}$ represents an alkyl group, phenyl group, a substituted phenyl group (examples of the substituent include a $C_{1-4}$ alkyl group, a $C_{1-4}$ alkoxyl group and the like.), an alkoxyl group, amino group, or an alkylamino group (e.g., methylamino group, dimethylamino group and the like)}, and —$SO_2R^{19}$ group {$R^{19}$ represents an alkyl group, phenyl group, a substituted phenyl group (examples of the substituent include a $C_{1-4}$ alkyl group, a $C_{1-4}$ alkoxyl group and the like), an alkoxyl group, amino group, or an alkylamino group (e.g., methylamino group, dimethylamino group and the like)}. Hydrogen atom, fluorine atom, chlorine atom, methyl group, ethyl group, acetyl group, carbamoyl group, carboxyl group, or nitro group is preferred.

In group (IV) represented by A in formula (I), examples of the group represented by $R^{20}$ include hydrogen atom, alkyl groups, acyl groups, alkoxycarbonyl groups, carbamoyl group, alkylcarbamoyl groups (e.g., methylcarbamoyl group and the like), and amidino group. Hydrogen atom or amidino group is preferred.

In group (IV) represented by A in formula (I), examples of the group represented by $R^{28}$ or $R^{29}$ include hydrogen atom, halogen atoms, hydroxyl group, alkyl groups, amino group, and alkylamino groups. Hydrogen atom is preferred.

In group (IV) represented by A in formula (I), the group or atom represented by Y is preferably CH.

In group (IV) represented by A in formula (I), the integer represented by n or o is preferably 2.

In group (IV) represented by A in formula (I), the integer represented by r is preferably 2.

In group (XIV) represented by A in formula (I), examples of the group represented by $R^{30}$, $R^{31}$, $R^{32}$, or $R^{33}$ include hydrogen atom, halogen atoms, hydroxyl group, alkyl groups, amino group, oxo group, alkylamino groups and the like. Hydrogen atom, an alkyl group, or oxo group is preferred.

In group (XIV) represented by A in formula (I), the group or atom represented by V is preferably —O—.

In group (XIV) represented by A in formula (I), the integer represented by s or t is preferably 1 or 2.

In formula (I), examples of the N-substituent of the piperidine ring represented by E together with A include hydrogen atom, an alkyl group, a substituted alkyl group (examples of the substituent include hydroxyl group, a halogen atom, amino group, an alkylamino group, an acylamino group, an alkoxycarbonylamino group, carbamoylamino group, guanidino group, oxo group, amidino group and the like), an acyl group, and amidino group. Hydrogen atom, an aminoalkyl group, an aminoalkyl group having oxo group, or amidino group is preferred.

In formula (I), examples of the substituent of the substituted phenyl group, which may substitute on the alkyl group or the alkoxyl group represented by $R^1$, $R^2$ or $R^3$, include hydroxyl group, a halogen atom, phenyl group, an alkyl group (e.g., a $C_{1-4}$ alkyl group and the like), an alkoxyl group (e.g., a $C_{1-4}$ alkoxyl group and the like), an acyl group (e.g., formyl group, acetyl group, propionyl group, butenyl group, benzoyl group, pivaloyl group and the like), carboxyl group, an alkoxycarbonyl group (e.g., a $C_{1-4}$ alkoxycarbonyl group and the like), an arylalkyloxycarbonyl group (e.g., benzyloxycarbonyl group and the like), an aryloxycarbonyl group (phenoxycarbonyl group and the like), amino group, an alkylamino group (e.g., a $C_{1-4}$ alkylamino group, dimethylamino group, cyclohexylamino group and the like), an alkenylamino group (e.g., allylamino group, allylmethylamino group, allylcyclohexylamino group and the like), an arylamino group (e.g., phenylamino group and the like), an arylalkylamino group (e.g., benzylamino group and the like), an acylamino group (e.g., formylamino group, acetylamino group, benzoylamino group, pivaloylamino group and the like), an acylalkylamino group (e.g., acetylmethylamino group, phthaloylamino group and the like), an alkoxycarbonylamino group (e.g., methoxycarbonylamino group, isopropoxycarbonylamino group and the like), an aryloxycarbonylamino group (e.g., benzyloxycarbonylamino group and the like), an alkoxycarbonylalkylamino group (e.g., methoxycarbonylmethylamino group and the like), an alkylsulfonylamino group (e.g., methylsulfonylamino group, methyl(methylsulfonyl)amino group and the like), an alkylsulfonylalkylamino group, an arylsulfonylamino group (e.g., benzenesulfonylamino group and the like), an arylsulfonylalkylamino group, carbamoyl group, an alkylcarbamoyl group (e.g., methylcarbamoyl group, ethylcarbamoyl group, N,N-dimethylcarbamoyl group, N,N'-dimethylcarbamoyl group and the like), an arylalkylcarbamoyl group (e.g., benzylcarbamoyl group and the like), and nitro group. Hydroxyl group, a halogen atom, an alkoxyl group, or amino group is preferred.

In formula (I), an example of the substituent of the substituted alkoxyl group, which may substitute on the alkyl group or alkoxyl group represented by $R^1$, $R^2$, or $R^3$, includes a $C_{1-4}$ alkoxyl group. Methoxy group or isopropoxy group is preferred.

In formula (I), examples of the alkoxycarbonyl group or aryloxycarbonyl group, which may substitute on the alkyl group or the alkoxyl group represented by $R^1$, $R^2$, or $R^3$, include a $C_{2-5}$ alkoxycarbonyl group, benzyloxycarbonyl group, and phenoxycarbonyl group. Methoxycarbonyl group or isopropoxycarbonyl group is preferred.

In formula (I), examples of the substituted carbamoyl group, which may substitute on the alkyl group or the alkoxyl group represented by $R^1$, $R^2$, or $R^3$, include a N-($C_{1-4}$ alkyl)carbamoyl group, a N,N-di($C_{1-4}$ alkyl)carbamoyl group, and a N,N'-di($C_{1-4}$ alkyl)carbamoyl group. Methylcarbamoyl group or N,N-dimethylcarbamoyl group is preferred.

In formula (I), examples of the substituted amino group, which may substitute on the alkyl group or the alkoxyl group represented by $R^1$, $R^2$, or $R^3$, include an alkylamino group (e.g., methylamino group, ethylamino group, n-propylamino group, isopropylamino group, cyclohexylamino group, dimethylamino group and the like), an alkenylamino group (e.g., allylamino group, allylmethylamino group, allylcyclohexylamino group and the like), an arylamino group (e.g., phenylamino group and the like), an arylalkylamino group (e.g., benzylamino group and the like), an acylamino group (e.g., formylamino group, acetylamino group, benzoylamino group, pivaloylamino group, phthaloylamino group and the like), an acylalkylamino group (e.g., acetylmethylamino group and the like), an alkoxycarbonylamino group (e.g., methoxycarbonylamino group, isopropoxycarbonylamino group and the like), an alkoxycarbonylalkylamino group (e.g., methoxycarbonylmethylamino group and the like), an arylalkyloxycarbonyl group (e.g., benzyloxycarbonylamino group and the like), an alkylsulfonylamino group (e.g., methylsulfonylamino group, methyl(methylsulfonyl)amino group and the like), an alkylsulfonylalkylamino group, an arylsulfonylamino group (e.g., phenylsulfonylamino group and the like), and an arylsulfonylalkylamino group. Methylamino group, allylamino group, acetylamino group, or methylsulfonylamino group is preferred.

Among the compounds represented by general formula (I), preferred compounds include those wherein X is —O—.

Other preferred compounds include those wherein A is group (II).

Other preferred compounds also include those wherein E is —CH$_2$CH$_2$— that forms piperidine ring group or a N-substituted piperidine ring group together with A.

More preferred compounds are those wherein R$^1$ is an alkyl group, a substituted alkyl group, an alkoxyl group, a substituted alkoxyl group, phenyl group, a substituted phenyl group, or a heterocyclic group, R$^2$ and R$^3$ may be the same or different and independently are hydrogen atom, an alkyl group, a substituted alkyl group, phenyl group, or a heterocyclic group, or R$^2$ and R$^3$ form a 5 to 7-membered carbon ring together with the carbon atom to which they bind, X is —O—, A is group (II), and E is hydrogen atom, or E is —CH$_2$CH$_2$— that forms piperidine ring group or a N-substituted piperidine ring group together with A.

Other class of more preferred compounds are those wherein R$^1$ is an alkyl group, a substituted alkyl group, an alkoxyl group, a substituted alkoxyl group, phenyl group, a substituted phenyl group, or a heterocyclic group; R$^2$ and R$^3$ may be the same or different and are independently hydrogen atom, an alkyl group, a substituted alkyl group, phenyl group, or a heterocyclic group, or R$^2$ and R$^3$ form a 5 to 7-membered carbon ring together with the carbon atom to which they bind; X is —CH$_2$—, —O—, or —NH—; A is:

(a) group (II) in which R$^7$ and R$^8$ may be the same or different and are independently hydrogen atom, carbamoyl group, or amidino group; R$^9$ and R$^{10}$ may be the same or different and are independently hydrogen atom or an alkyl group; m is an integer of from 1 to 8; and —(C)$_m$— is a saturated carbon chain;

(b) group (III) in which both R$^7$ and R$^8$ are hydrogen atom; R$^{24}$, R$^{25}$, R$^{26}$, and R$^{27}$ may be the same or different and are independently hydrogen atom or an alkyl group; p and q are independently an integer of from 0 to 2; —(C)$_p$— and —(C)$_q$— are independently single bond or a saturated carbon chain; and B is a carbocyclic group;

(c) group (IV) in which R$^{20}$ is hydrogen atom; R$^{28}$ and R$^{29}$ may be the same or different and are independently hydrogen atom or an alkyl group; n and o are independently an integer of from 0 to 5; r is independently an integer of from 0 to 4; —(C)$_r$— is independently single bond or a saturated carbon chain; and Y is CH; or (d) group (XIV) in which both R$^7$ and R$^8$ are hydrogen atom; R$^{30}$, R$^{31}$, R$^{32}$, and R$^{33}$ may be the same or different and are independently hydrogen atom, an alkyl group, or oxo group; s is an integer of from 0 to 3; t is an integer of 1 to 3; —(C)$_s$— and —(C)$_t$— are independently single bond or a saturated carbon chain; and V is —O—; and E is hydrogen atom, or E is —CH$_2$CH$_2$— that forms piperidine ring group or a N-substituted piperidine ring group together with A.

Further preferred compounds include those wherein R$^1$ is an alkyl group, a substituted alkyl group, an alkoxyl group, a substituted alkoxyl group, phenyl group, a substituted phenyl group, or a heterocyclic group; R$^2$ and R$^3$ may be the same or different and are independently hydrogen atom, an alkyl group, a substituted alkyl group, phenyl group, or a heterocyclic group, or R$^2$ and R$^3$ form a 5 to 7-membered carbon ring together with the carbon atom to which they bind; X is —O—; A is:

(a) group (II) in which R$^7$ and R$^8$ may be the same or different and are independently hydrogen atom, carbamoyl group, or amidino group; R$^9$ and R$^{10}$ may be the same or different and are independently hydrogen atom or an alkyl group; m is an integer of from 1 to 8; and —(C)$_m$— is a saturated carbon chain; or (b) group (XIV) in which both R$^7$ and R$^8$ are hydrogen atom; R$^{30}$, R$^{31}$, R$^{32}$, and R$^{33}$ may be the same or different and are independently hydrogen atom, an alkyl group, or oxo group; s is an integer of from 0 to 3; t is an integer of from 1 to 3; —(C)$_s$— and —(C)$_t$— are independently single bond or a saturated carbon chain; and V is —O—; and E is hydrogen atom, or E is —CH$_2$CH$_2$— that forms piperidine ring group or a N-substituted piperidine ring group together with A.

Still further preferred compounds include those wherein R$^1$ is an alkyl group or a phenylalkyl group; R$^2$ and R$^3$ may be the same or different and are independently an alkyl group; X is —O—; A is group (II) in which R$^7$ and R$^8$ may be the same or different and are independently hydrogen atom, carbamoyl group, or amidino group; R$^9$ and R$^{10}$ may be the same or different and are independently hydrogen atom or an alkyl group; m is an integer of from 1 to 8; and —(C)$_m$— is a saturated carbon chain; and E is hydrogen atom.

Preferred specific examples of the compound represented by general formula (I) include, but not limited thereto:

(S)-6-amino-2-(((R)-1-(benzyloxycarbonylamino)ethyl)(hydroxyphosphinoyl)oxy)hexanoic acid, (S)-6-amino-2-((2-methyl-1-(3-phenylpropanoylamino)propyl)(hydroxyphosphinoyl)oxy)hexanoic acid, (S)-6-amino-2-((2-ethyl-1-(3-phenylpropanoylamino)butyl)(hydroxyphosphinoyl)oxy)hexanoic acid, (S)-6-amino-2-((1-(3-phenylpropanoylamino)ethyl)(hydroxyphosphinoyl)oxy)hexanoic acid, (S)-6-amino-2-(((3-phenylpropanoylamino)methyl)(hydroxyphosphinoyl)oxy)hexanoic acid, (S)-6-amino-2-((cyclopropyl(3-phenylpropanoylamino)methyl)(hydroxyphosphinoyl)oxy)hexanoic acid, (S)-5-amino-2-((2-methyl-1-(3-phenylpropanoylamino)propyl)(hydroxyphosphinoyl)oxy)pentanoic acid, (S)-6-amino-2-((1-(3-phenylpropanoylamino)butyl)(hydroxyphosphinoyl)oxy)hexanoic acid, (S)-6-amino-2-((1-cyclohexyl-1-(3-phenylpropanoylamino)methyl)(hydroxyphosphinoyl)oxy)hexanoic acid, (S)-6-amino-2-((1-cyclobutyl-1-(3-phenylpropanoylamino)methyl)(hydroxyphosphinoyl)oxy)hexanoic acid, (S)-4-amino-2-((2-methyl-1-(3-phenylpropanoylamino)propyl)(hydroxyphosphinoyl)oxy)butanoic acid, (S)-6-amino-2-((3-methyl-1-(3-phenylpropanoylamino)butyl)(hydroxyphosphinoyl)oxy)hexanoic acid, (S)-2-((2-methyl-1-(3-phenylpropanoylamino)propyl)(hydroxyphosphinoyl)oxy)-4-ureido-butanoic acid, (S)-6-amino-2-((1-(3-phenylpropanoylamino)cyclohexyl)(hydroxyphosphinoyl)oxy)hexanoic acid, (S)-2-((2-methyl-1-(3-phenylpropanoylamino)propyl)(hydroxyphosphinoyl)oxy)-5-ureido-pentanoic acid, (S)-6-amino-2-((1-(3-phenylpropanoylamino)propyl)(hydroxyphosphinoyl)oxy)hexanoic acid, (S)-4-guanidino-2-((2-methyl-1-(3-phenylpropanoylamino)propyl)(hydroxyphosphinoyl)oxy)butanoic acid, (S)-5-guanidino-2-((2-methyl-1-(3-phenylpropanoylamino)propyl)(hydroxyphosphinoyl)oxy)pentanoic acid, (S)-6-amino-2-((2-methyl-(1R)-(3-phenylpropanoylamino)propyl)(hydroxyphosphinoyl)oxy)hexanoic acid, (S)-6-amino-2-((1-(3-phenylpropanoylamino)cyclopentyl)(hydroxyphosphinoyl)oxy)hexanoic acid,
(S)-6-amino-2-((2-methyl-(1S)-(3-phenylpropanoylamino)propyl)(hydroxyphosphinoyl)oxy)hexanoic acid,
6-amino-2-((2-methyl-1-(3-phenylpropanoylamino)propyl)hydroxyphosphinoyl)methylhexanoic acid,
(S)-6-amino-2-((3,3-dimethyl-1-(3-phenylpropanoylamino)butyl)(hydroxyphosphinoyl)oxy)hexanoic acid,
(S)-6-amino-2-(2-methyl-1-(4-phenylbutanoylamino)propyl)(hydroxyphosphinoyl)oxy)hexanoic acid,
(S)-6-amino-2-((4,4,4-trifluoro-1-(3-phenylpropanoylamino)buty)hydroxyphosphinoyl)oxy)hexanoic acid,
(S)-7-amino-2-((1-(3-phenylpropanoylamino)cyclopentyl)(hydroxyphosphinoyl)oxy)heptanoic acid,
(R)-7-amino-2-((1-(3-phenylpropanoylamino)cyclopentyl)(hydroxyphosphinoyl)oxy)heptanoic acid,
(S)-7-amino-2-((2-methyl-(1R)-(3-phenylpropanoylamino)propyl)(hydroxyphosphinoyl)oxy)heptanoic acid,
2-(2-methyl-(1R)-(3-phenylpropanoylamino)propyl(hydroxyphosphinoyl)oxy)-4-(piperidin-4-yl)butanoic acid,
1-(trans-(4-aminomethylcyclohexyl))-1-(2-methyl-(1R)-(3-phenylpropanoylamino)propyl(hydroxyphosphinoyl)oxy)acetic acid,
3-aminoacetoxy-2-(2-methyl-(1R)-(3-phenylpropanoylamino)propyl(hydroxyphosphinoyl)oxy)propanoic acid,
8-amino-2-(2-methyl-(1R)-(3-phenylpropanoylamino)propyl(hydroxyphosphinoyl)oxy)octanoic acid,
(S)-6-amino-2-((1-phenyl-1-(3-phenylpropanoylamino)methyl)(hydroxyphosphinoyl)oxy)hexanoic acid,
(S)-6-amino-2-((1-(3-phenylpropanoylamino)-1-(tetrahydropyran-4-yl)methyl)(hydroxyphosphinoyl)oxy)hexanoic acid,
(S)-5-amino-2-((3-methyl-1-(3-phenylpropanoylamino)butyl)(hydroxyphosphinoyl)oxy)pentanoic acid,
(S)-6-amino-2-((2-hydroxy-1-(3-phenylpropanoylamino)ethyl)(hydroxyphosphinoyl)oxy)hexanoic acid,
(S)-6-amino-2-((1-cycloheptyl-1-(3-phenylpropanoylamino)methyl)(hydroxyphosphinoyl)oxy)hexanoic acid,
(S)-6-amino-2-((1-(piperidin-4-yl)-1-(3-phenylpropanoylamino)methyl)(hydroxyphosphinoyl)oxy)hexanoic acid,
(S)-6-amino-2-((4-amino-1-(3-phenylpropanoylamino)butyl)(hydroxyphosphinoyl)oxy)hexanoic acid,
(S)-6-amino-2-((1-(4-methylcyclohexyl)-1-(3-phenylpropanoylamino)methyl)(hydroxyphosphinoyl)oxy)hexanoic acid,
(S)-6-amino-2-(((1R)-((2S)-amino-3-phenylpropanoylamino)-2-methylpropyl)(hydroxyphosphinoyl)oxy)hexanoic acid,
(S)-6-amino-2-((2-methyl-(1R)-phenylacetylaminopropyl)(hydroxyphosphinoyl)oxy)hexanoic acid,
(S)-6-amino-2-((1-((2R)-amino-3-phenylpropanoylamino)-2-methylpropyl)(hydroxyphosphinoyl)oxy)hexanoic acid,
(S)-6-amino-2-((1-(3-cyclopentylpropanoylamino)-2-methylpropyl)(hydroxyphosphinoyl)oxy)hexanoic acid,
(S)-6-amino-2-((1-(2,4-difluorobenzoylamino)-2-methylpropyl)(hydroxyphosphinoyl)oxy)hexanoic acid,
(S)-6-amino-2-((1-benzoylamino-2-methylpropyl)(hydroxyphosphinoyl)oxy)hexanoic acid,
(S)-6-amino-2-((1-(3-(2-methoxyphenyl)propanoylamino)-2-methylpropyl)(hydroxyphosphinoyl)oxy)hexanoic acid,
(S)-6-amino-2-((1-(4-methoxyphenyl)acetylamino-2-methylpropyl)(hydroxyphosphinoyl)oxy)hexanoic acid,
(S)-6-amino-2-((1-heptanoylamino-2-methylpropyl)(hydroxyphosphinoyl)oxy)hexanoic acid,
(S)-6-amino-2-((1-(2-amino-2-phenylacetylamino)-2-methylpropyl)(hydroxyphosphinoyl)oxy)hexanoic acid,
(S)-6-amino-2-((2-methyl-1-((pyridin-2-yl)acetylamino)propyl)(hydroxyphosphinoyl)oxy)hexanoic acid,
(S)-6-amino-2-((1-(4-methoxybenzoylamino)-2-methylpropyl)(hydroxyphosphinoyl)oxy)hexanoic acid,
(S)-6-amino-2-(((1R)-(4-methoxybenzoylamino)-2-methylpropyl)(hydroxyphosphinoyl)oxy)hexanoic acid,
(S)-6-amino-2-((1-dodecanoylamino-2-methylpropyl)(hydroxyphosphinoyl)oxy)hexanoic acid,
(S)-2-((1-acetylamino-2-methylpropyl)(hydroxyphosphinoyl)oxy)-6-aminohexanoic acid,
(S)-6-amino-2-((1-(3-(4-aminophenyl)propanoylamino)-2-methylpropyl)(hydroxyphosphinoyl)oxy)hexanoic acid,
(S)-6-amino-2-((1-(3-(3-aminophenyl)propanoylamino)-2-methylpropyl)(hydroxyphosphinoyl)oxy)hexanoic acid,
(S)-6-amino-2-((2-methyl-1-(trifluoroacetylamino)propyl)(hydroxyphosphinoyl)oxy)hexanoic acid,
(S)-6-amino-2-((2-methyl-1-(3-phenyl-(2S)-(3-phenylpropanoylamino)propanoylamino)propyl)(hydroxyphosphinoyl)oxy)hexanoic acid,
(S)-6-amino-2-((2-methyl-1-(5-oxohexanoylamino)propyl)(hydroxyphosphinoyl)oxy)hexanoic acid,
(S)-6-amino-2-((1-((3R)-hydroxybutanoylamino)-2-methylpropyl)(hydroxyphosphinoyl)oxy)hexanoic acid,
(S)-6-amino-2-((1-(3-methoxypropanoylamino)-2-methylpropyl)(hydroxyphosphinoyl)oxy)hexanoic acid,
(S)-6-amino-2-((2-methyl-1-(3,4,5-trimethoxybenzoylamino)propyl)(hydroxyphosphinoyl)oxy)hexanoic acid,
(S)-6-amino-2-((1-(3-carboxypropanoylamino)-2-methylpropyl)(hydroxyphosphinoyl)oxy)hexanoic acid,
(S)-6-amino-2-((2-methyl-1-(pyridin-2-carbonylamino)propyl)(hydroxyphosphinoyl)oxy)hexanoic acid,
(S)-6-amino-2-((2-methyl-1-(morpholine-4-carbonylamino)propyl)(hydroxyphosphinoyl)oxy)hexanoic acid,
4-((2-methyl-1-(3-phenylpropionylamino)propyl)(hydroxyphosphinoyl)oxy)piperidine-4-carboxylic acid,
1-amidino-4-((2-methyl-1-(3-phenylpropionylamino)propyl)(hydroxyphosphinoyl)oxy)piperidine-4-carboxylic acid,
1-(2-aminoethyl)-4-((2-methyl-1-(3-phenylpropionylamino)propyl)(hydroxyphosphinoyl)oxy)piperidine-4-carboxylic acid,
(R)-6-amino-2-((2-methyl-(1R)-(3-phenylpropanoylamino)propyl)(hydroxyphosphinoyl)oxy)hexanoic acid, and
7-amino-2-((2-methyl-1-(3-phenylpropanoylamino)propyl)hydroxyphosphinoyl)methylheptanoic acid.

The compound represented by the aforementioned formula (I) may optionally have one or more asymmetric carbon atoms and exist as a stereoisomer (an optical isomer or a diastereoisomer) based on the asymmetric carbon atom(s). Any mixtures of the stereoisomers and racemates as well as the stereoisomers in a pure form fall within the scope of the present invention, and any of the aforementioned substances may be used as an active ingredient of the medicament of the present invention. When the compound represented by the aforementioned formula (I) has an olefinic double bond, the compound may exist as a geometrical isomer in either Z- or E-form or a mixture thereof, any of which falls within the scope of the present invention. The geometrical isomer in a pure form or a mixture thereof may be used as an active ingredient of the medicament of the present invention.

Among the compounds of formula (I) according to the present invention, those wherein X is oxygen atom or —NH— in formula (I) can be prepared by synthetic method (I), (II), or (III) shown below. The compounds wherein X is —CH$_2$— and E is hydrogen atom can be prepared by the following synthetic method (IV), (V), (VI), or (VII). The compounds wherein X is —CH$_2$— and E is —CH$_2$CH$_2$— that forms a piperidine ring group or a N-substituted piperidine ring group together with A can be prepared by synthetic method (VI) or (VII). However, preparations of the compounds of the present invention are not limited to these methods.

In order to synthesize the compound of formula (I) of the present invention, the amino group (the amino group herein defined includes an amino group on the piperidine ring formed by E together with A.), imino group, and carboxyl group used in the following synthetic methods (I) to (VII) may be protected, if desired. As a protecting group, ordinary protecting groups can be used. Preferably, examples for an amino group. or an imino group includes methoxycarbonyl group, tert-butyloxycarbonyl group, benzyloxycarbonyl group, methoxybenzyloxycarbonyl group, nitrobenzyloxycarbonyl group, allylbenzyloxycarbonyl group, acetyl group, trifluoroacetyl group, trichloroacetyl group, benzoyl group, phthaloyl group, trityl group, benzyl group, methoxybenzyl group, allyl group, formyl group and the like, and examples for carboxyl group include methyl group, tert-butyl group, benzyl group, paramethoxybenzyl group, nitrobenzyl group, allyl group, benzhydryl group, trityl group and the like.

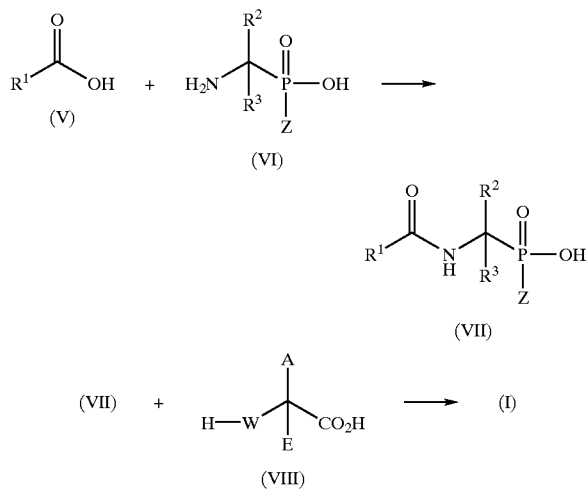

Synthetic method (I)

[In the scheme, R$^1$, R$^2$, R$^3$, A, and E have the same meanings as those defined in formula (I), W represents oxygen atom or —NH—, and Z represents hydrogen atom, hydroxyl group, or alkoxyl group.]

A compound of the formula (VII) can be prepared according to the method described in Tetrahedron Lett., 7333 (1991), U.S. Pat. No. 4,616,005 or the like. Specifically, the method comprises condensing a compound of formula (V) and a compound of formula (VI) by applying, for example, the dehydration method using N,N'-dicyclohexylcarbodiimide (DCC), benzotriazoleoxytrisdimethylamino-phosphonium tetrafluorophosphate (BOP) or the like, the acid halide method using thionyl chloride, oxalyl chloride, phosphorus oxychloride or the like, the mixed acid anhydride method using pivaloyl chloride, a chloroformic acid ester or the like in a solvent which does not participate in the reaction for a reaction time of from 0.5 to 72 hours, preferably from 2 to 24 hours at a reaction temperature of from –78° C. to 100° C., preferably from 0° C. to 30° C.

As the amine of formula (VI), a commercially available compound maybe used, or the amine can be synthesized according to the method described in Synthesis, 370(1988), Liebigs. Ann. Chem., 861(1988), J. Chem. Soc. Perkin trans. 1, 2846(1984) or the like. Where Z is hydrogen atom in the compound of formula (VII), the hydrogen atom can be converted into hydroxyl group by an ordinary oxidation in this step, and the hydroxyl group may be converted into an alkoxyl group, if desired.

The condensation between the compound of formula (VII) and a carboxylic acid compound of formula (VIII) can be carried out according to the method described in J. Am. Clem. Soc., 297(1991), J. Org. Chem., 658(1994), J. Med. Chem., 3303(1998), Synthesis, 556(1986), J. Med. Chem., 1459(1990), Tetrahedron Lett., 1751(1986) or the like. Specifically, the method comprises condensing the compound of formula (VII) and the compound of formula (VIII) by applying, for example, the dehydration method using N-(dimethylaminopropyl)-N'-ethylcarbodiimide hydrochloride, N,N'-dicyclohexylcarbodiimide (DCC), benzotriazoleoxytrisdimethylamino-phosphonium tetrafluorophosphate (BOP) or the like, the acid halide method using thionyl chloride, oxalyl chloride, phosphorus oxychloride or the like, the mixed acid anhydride method using pivaloyl chloride, a chloroformic acid ester or the like in a solvent which does not participate in the reaction for a reaction time of from 0.5 to 72 hours, preferably from 2 to 24 hours at a reaction temperature of from –78° C. to 100° C., preferably from 0° C. to 30° C. The compound wherein X is oxygen atom or —NH— in formula (I) can be synthesized through deprotection at need after the condensation, or when Z is hydrogen atom, by performing oxidation according to a conventional method after the condensation, and then deprotection at need.

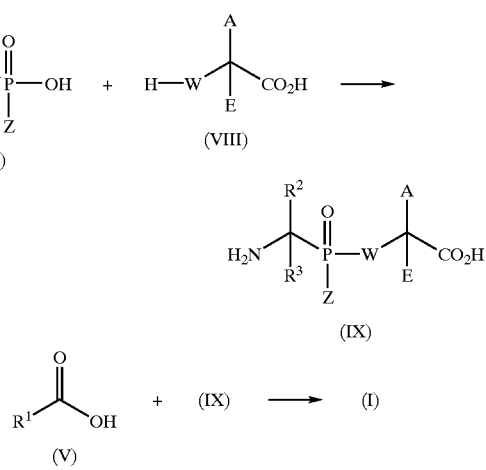

Synthetic method (II)

[In the scheme, R$^1$, R$^2$, R$^3$, A, E, W, and Z have the same meanings as those defined above.]

The compound of formula (I) can be synthesized according to the method shown in the aforementioned synthetic method (I).

Where Z is hydrogen atom in a compound of formula (IX), the hydrogen atom can be converted into hydroxyl group by an ordinary oxidation in this step, and the resulting hydroxyl group may be converted into an alkoxyl group, if desired.

The condensation between the compound of formula (V) and the compound of formula (IX) can be performed in the same manner as those described in the aforementioned synthetic method (I). The compound wherein X is oxygen atom or —NH— in formula (I) can be synthesized through deprotection at need after the condensation, or where Z is hydrogen atom, by an oxidation in a conventional manner after the condensation, and then deprotection at need.

Synthetic method (III)

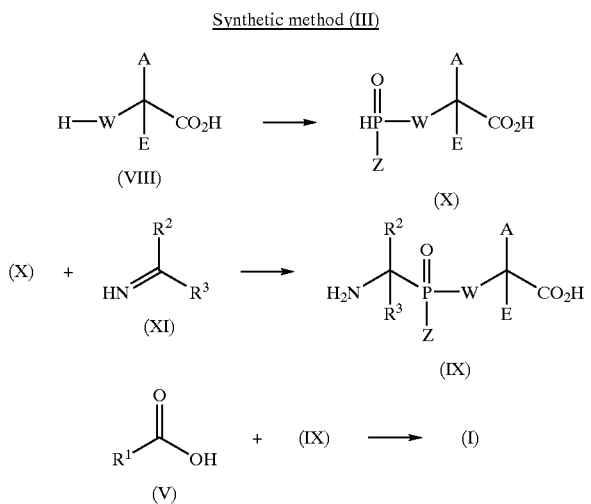

[In the scheme, $R^1$, $R^2$, $R^3$, A, E, W, and Z have the same meanings as those defined above.]

A compound of formula (X) can be prepared according to the method described in Tetrahedron Lett., 5457(1996), Ibid., 6073(1996) or the like. Specifically, the compound of formula (X) wherein Z is hydroxyl group or an alkoxyl group can be obtained by reacting a compound of formula (VIII) with a phosphorylating agent such as 2-chloro-4H-1,3,2-benzodioxaphophorin-4-one, 2-chloro-1,3,2-dioxaphophorane, 2-cyanoethyl N,N'-diisopropylchlorophosphoramidate, and phosphorus trichloride in a solvent which does not participate in the reaction for a reaction time of from 0.5 to 72 hours, preferably from 2 to 24 hours, at a reaction temperature of from −78° C. to 100° C., preferably from −30° C. to 30° C., and then performing hydrolysis or alcoholysis, if desired. When Z is hydroxyl group in formula (X), a compound wherein Z is an alkoxyl group in formula (X) can also be obtained by performing esterification by a conventional method.

A compound of formula (IX) can be synthesized according to the method described in Tetrahedron Lett., 5457 (1996) or the like. Specifically, the compound of formula (IX) wherein Z is hydroxyl group or an alkoxyl group can be obtained by reacting the compound of formula (X) with the compound of formula (XI), per se, or under irradiation by ultrasound or in the presence of a Lewis acid such as boron trifluoride, titanium chloride, tin chloride and yttrium triflate, in a solvent which does not participate in the reaction for a reaction time of from 0.5 to 72 hours, preferably from 2 to 24 hours at a reaction temperature of from −78° C. to 100° C., preferably from −30° C. to 60° C., and then performing deprotection at need. The compound of formula (I) can be synthesized according to the method of synthetic method (I).

Snythetic method (IV)

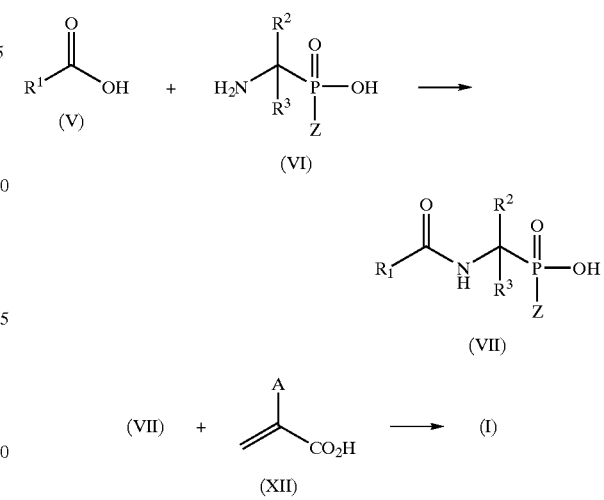

[In the scheme, $R^1$, $R^2$, $R^3$, and A have the same meanings as those defined above, and Z represents hydrogen atom.]

A compound of formula (VII) can be synthesized by the method shown in the aforementioned synthesis method (I).

The reaction of the compound of formula (VII) and a compound of formula (XII) can be carried out according to the method described in Bioorg. Med. Chem. Lett., 1257 (1996), J. Med. Chem., 1652(1989), J. Am. Chem. Soc., 297(1991), Tetrahedron Lett., 3375(1998), Tetrahedron Lett., 2933(1990), or the like. Specifically, the method comprises activating or esterifying the compound of formula (VII), if desired, by using a silyl group or the like to elevate the reactivity of the compound of formula (VII), and subjecting the compound of formula (XII) to Michael addition in a solvent which does not participate in the reaction or without solvent, for a reaction time of from 0.5 to 72 hours, preferably from 2 to 24 hours at a reaction temperature of from −78° C. to 100° C., preferably from 0° C. to 50° C. The compound wherein X is —$CH_2$— and E is hydrogen atom in formula (I) can be synthesized through deprotection at need after the Michael addition.

A compound of formula (XII) can be synthesized according to the method described in J. Med. Chem., 2461(1994) or the like.

Synthetic method (V)

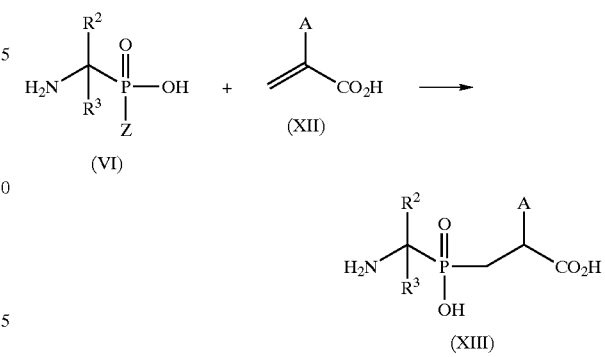

-continued

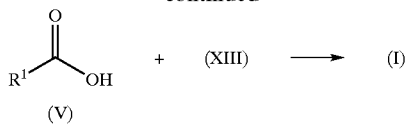

[In the scheme, $R^1$, $R^2$, $R^3$, and A have the same meanings as those defined above, and Z represents hydrogen atom.]

A compound of formula (XIII) can be synthesized according to the method shown in the aforementioned synthetic method (IV).

The condensation between the compound of formula (V) and the compound of formula (XIII) can be performed according to the method shown in the aforementioned synthetic method (I), and the compound wherein X is —$CH_2$— and E is hydrogen atom in formula (I) can be synthesized through deprotection at need after the condensation.

Synthetic method (VI)

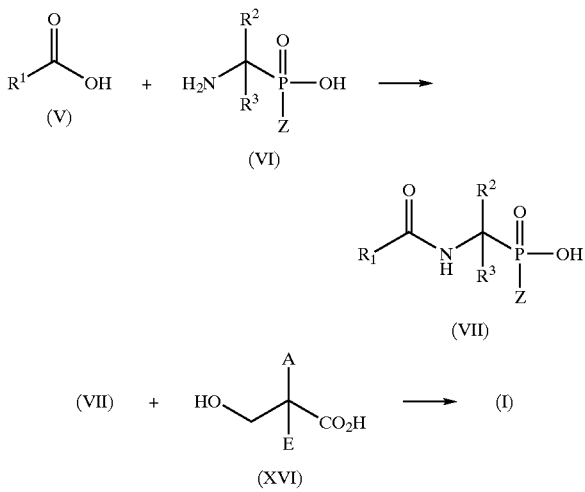

[In the scheme, $R^1$, $R^2$, $R^3$, and A have the same meanings as those defined above, E represents hydrogen atom or —$CH_2CH_2$— that forms piperidine ring group or a N-substituted piperidine ring group together with A, and Z represents hydrogen atom.]

The compound of formula (VII) can be synthesized by the method shown in the aforementioned synthetic method (I).

A compound of formula (XVI) can be synthesized according to the method described in J. Med. Chem., 2461(1994) or the like.

The condensation between the compound of formula (VII) and the compound of formula (XVI) can be performed according to the method described in Bioorg. Med. Chem. Lett., 1629(1996). Specifically, the compound wherein X is carbon atom in formula (I) can be synthesized by activating the hydroxyl group in formula (XVI) with trifluoromethanesulfonic anhydride, methanesulfonyl chloride, toluenesulfonyl chloride or the like, or substituting the hydroxyl group in formula (XVI) with a halogen atom by a conventional method, and by activating or esterifying the compound of formula (VII) with silyl group or the like at need to elevate the reactivity of the compound of formula (VII), and then, carrying out the reaction in a solvent which does not participate in the reaction or without solvent, in the presence of base at need such as triethylamine, diisopropylethylamine, pyridine, lutidine, potassium carbonate, sodium hydrogencarbonate, sodium hydride and lithium diisopropylamide, for a reaction time of from 0.5 to 72 hours, preferably from 2 to 24 hours at a reaction temperature of from −78° C. to 100° C., preferably from −78° C. to 60° C., and performing deprotection at need.

Synthetic method (VII)

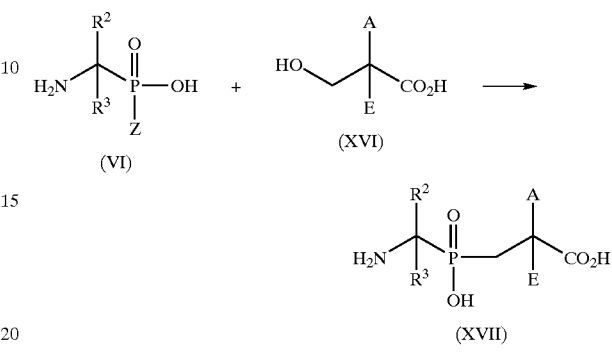

[In the scheme, $R^1$, $R^2$, $R^3$, and A have the same meanings as those defined above, E represents hydrogen atom or —$CH_2CH_2$— that forms piperidine ring group or a N-substituted piperidine ring group together with A, and Z represents hydrogen atom.]

A compound of formula (XVII) can be synthesized according to the method shown in the aforementioned synthetic method (VI). The condensation between the compound of formula (V) and the compound of formula (XVII) can be performed according to the method shown in the aforementioned synthetic method (I), and the compound wherein X is —$CH_2$— in formula (I) can be synthesized through deprotection after the condensation.

Specific preparations of the compound of the present invention encompassed within formula (I) are shown in Examples of the specification. Those of ordinary skill in the art can easily prepare the compound of the present invention falling within formula (I) by referring to the aforementioned general explanation and specific explanation in examples, and by appropriately selecting a starting material, a reagent, reaction conditions and the like, and if necessary, applying appropriate modifications and alterations to these methods.

The compound of formula (I) according to the present invention may exist as a salt, and may preferably exist as a pharmacologically acceptable salt. Such salts include medicinally acceptable nontoxic salts, for example, alkali metal salts and alkaline-earth metal salts such as sodium salt, potassium salt, and calcium salt, hydrogen halide salts such as hydrochloride, inorganic salts such as nitrate, sulfate and phosphate, salts of sulfonic acids such as methanesulfonic acid and benzenesulfonic acid, salts of organic acids such as fumaric acid, succinic acid, citric acid, oxalic acid and maleic acid, salts of amino acids such as glutamic acid and aspartic acid, and the like.

The compound of formula (I) according to the present invention may exist as a hydrate or a solvate. Preferred solvates include a solvate with ethanol and the like. Any salts, hydrates, and solvates of the compound of formula (I) fall within the scope of the present invention.

The compound of formula (I) according to the present invention have thrombolytic activity based on inhibition of carboxypeptidase B in human plasma. Accordingly, a substance selected from the group consisting of the compound of formula (I) according to the present invention and a pharmacologically acceptable salt thereof, and a hydrate thereof and a solvate thereof is useful as an active ingredient of medicaments for therapeutic and/or preventive treatment of various thrombotic diseases such as myocardial infarction, cerebral infarction, angina, pulmonary embolus, chronic arterial obliteration, acute arterial thrombus and embolus, angitis syndrome, diabetic gangrene, thrombophlebitis and deep vein thrombosis, thrombotic thrombocytopenic purpura and hemolytic-uremic syndrome, disseminated intravascular coagulation, and anti-phospholipid antibody syndrome, and pathologic conditions such as diabetes, hyperlipemia, and inflammation in which thrombotic tendency due to the decrease of in vivo fibrinoliablity have been recognized.

The substance selected from the group consisting of the compound of formula (I) according to the present invention and a pharmacologically acceptable salt thereof, and a hydrate thereof and a solvate thereof is also effective as a carboxypeptidase B inhibitor. As the carboxypeptidase B inhibitor according to the present invention, the aforementioned substance, per se, can be used. For example, the inhibitor can also be used as a reagent for enzymes.

The substance selected from the group consisting of the compound of formula (I) according to the present invention and a pharmacologically acceptable salt thereof, and a hydrate thereof and a solvate thereof, per se, may be used as a medicament. However, the medicament of the present invention is preferably provided as a pharmaceutical composition which comprises the aforementioned substance together with a pharmacologically acceptable carrier, and can be administered to a human as well as an animal other than human by either an oral or parenteral (e.g., intravenous, intramuscular, subcutaneous, rectal, transdermal and the like) administration. Two or more of the aforementioned substances may be formulated in combination in the pharmaceutical composition.

The pharmaceutical composition which comprises as an active ingredient a substance selected from the group consisting of the compound of formula (I) according to the present invention and a pharmacologically acceptable salt thereof, and a hydrate thereof and a solvate thereof can be prepared as a formulation suitable for a route of administration. Specifically, the pharmaceutical composition can be prepared typically in any one of formulations including preparations for parenteral administration such as injections for intravenous or intramuscular administration, drip infusions, inhalants, transdermal preparations, transmucosal preparations, rectal preparations, oleaginous suppositories, and aqueous suppositories, and preparations for oral administration such as capsules, tablets, granules, powders, pills, fine granules, and troches.

As the pharmacologically acceptable carrier used for the manufacture of these various preparations, one or more solid or liquid carriers suitable for administration to humans as well as animals other than humans can be used. Examples of the solid carriers include, for example, starch, lactose, crystalline cellulose, calcium carbonate and the like. Examples of the liquid carriers include, for example, physiological saline, ethanol and the like.

One or more kinds of commonly used excipients, bulking agents, binders, moisturizing agents, disintegrators, surface active agents, lubricants, dispersants, buffering agents, preservatives, solubilizing aids, antiseptics, corrigents, soothing agents, stabilizers and the like may be used as the pharmacologically acceptable carrier. Examples of usable nontoxic carriers include, for example, lactose, fructose, glucose, starch, gelatin, magnesium carbonate, synthetic magnesium silicate, talc, magnesium stearate, methylcellulose and its salts, gum arabic, polyethylene glycol, syrup, Vaseline, ethanol, propylene glycol, citric acid, sodium chloride, sodium sulfite, sodium phosphate and the like.

The content of the substance selected from the group consisting of the compound of formula (I) according to the present invention and a pharmacologically acceptable salt thereof, and a hydrate thereof and a solvate thereof contained in the pharmaceutical composition may vary depending on dosage forms. Generally, the amount may be from about 1% to about 70% by weight, preferably from about 5% to about 50% by weight based on the total weight of the composition.

A dose can be appropriately chosen in view of the use of the medicament, the age, sexuality and conditions of a patient and the like. The dose may generally be from about 0.1 mg to 1,000 mg, and preferably from 1 mg to 300 mg per day for an adult for therapeutic treatment of thrombotic diseases. The aforementioned dose can be administered once a day or several times a day as divided portions.

EXAMPLES

The present invention will be explained more specifically by examples. However, the scope of the present invention is not limited to the following examples.

Example 1

(S)-6-Amino-2-(((R)-1-(benzyloxycarbonylamino)ethyl)(hydroxyphosphinoyl)oxy)hexanoic acid (a) (R)-1-(benzyloxycarbonylamino)ethylphophonic acid monomethyl ester (40.7 mg) described in Biochemistry, 6294(1989) was dissolved in tetrahydrofuran (1 ml), and pivaloyl chloride (71.8 mg) and triethylamine (90.4 mg) were added. The mixture was stirred at room temperature for 30 minutes, then added with a tetrahydrofuran (1 ml) solution of methyl (S)-2-hydroxy-6-(tert-butoxycarbonylamino)hexanoate (38.9 mg), which is obtainable from 6-amino-2-hydroxyhexanoic acid described in Chem. Pharm. Bull., 621(1976) by a conventional method, and stirred at room temperature overnight. The organic substances were extracted with ethyl acetate and the extract was washed with saturated brine, and then the organic layer was dried over anhydrous sodium sulfate. The residue was purified by silica gel thin-layer chromatography to obtain methyl (S)-2-(((R)-1-(benzyloxycarbonylamino)ethyl)(methoxyphosphinoyl)oxy)-6-(tert-butoxycarbonylamino)hexanoate (9.7 mg, 13%). This compound was subjected to the measurement of molecular weight and then used in the following reaction.

TSPMS(m/z): 517($M^+$+1).

(b) A methanol (1 ml) solution of the methyl (S)-2-(((R)-1-(benzyloxycarbonylamino)ethyl)(methoxyphosphinoyl)oxy)-6-(tert-butoxycarbonylamino)hexanoate (9.7 mg) obtained in the above step (a) was added with potassium carbonate (5.7 mg), and the mixture was stirred at room temperature for 3 hours. The mixture was acidified with hydrochloric acid and the organic substances were extracted with ethyl acetate. The extract was washed with saturated brine, and then the organic layer was dried over anhydrous sodium sulfate to obtain (S)-2-(((R)-1-(benzyloxycarbonylamino)ethyl)(hydroxyphosphinoyl)oxy)-6-(tert-butoxycarbonylamino)hexanoic acid (3.1 mg, 34%). This compound was subjected to the measurement of molecular weight and then used in the following reaction without further purification.

TSPMS(m/z): 489(M$^+$+1).

(c) A dichloromethane (0.5 ml) suspension of the (S)-2-(((R)-1-(benzyloxycarbonylamino)ethyl)(hydroxyphosphinoyl)oxy)-6-(tert-butoxycarbonylamino)hexanoic acid (3.1 mg) obtained in the above step (b) was added with anisol (0.05 ml) and trifluoroacetic acid (0.5 ml) at 0° C., and the mixture was stirred at the same temperature for 2 hours. The reaction mixture was concentrated, and the residue was washed with isopropyl ether to obtain trifluoroacetic acid salt of the title compound: (S)-6-amino-2-(((R)-1-(benzyloxycarbonylamino)ethyl)(hydroxyphosphinoyl)oxy)hexanoic acid (3.0 mg, 94%).

$^1$H-NMR(D$_2$O): δ1.1–1.8(9H,m), 2.8–2.9(2H,m), 3.5–3.7(1H,m), 4.1–4.2(1H,m), 4.97(2H,s), 7.2–7.5(5H,m).

TSPMS(m/z): 389(M$^+$+1).

Example 2

(S)-6-Amino-2-((2-methyl-1-(3-phenylpropanoylamino)propyl)(hydroxyphosphinoyl)oxy)hexanoic acid (a) 1-Amino-2-methylpropylphosphinic acid (99.8 mg) prepared by the method described in J. Chem. Soc. Perkin tans 1, 2845(1984) was dissolved in 5 N aqueous sodium hydroxide (0.3 ml). 3-Phenylpropanoyl chloride (0.1 ml) was added to the solution at 0° C., and the resulting mixture was stirred at 0° C. for 1 hour and at room temperature for 3 hours. The mixture was acidified with hydrochloric acid and added with sodium chloride, and then the organic substances were extracted with ethyl acetate. The extract was washed with saturated aqueous sodium chloride and then the organic layer was dried over anhydrous magnesium sulfate. The solvent was evaporated to obtain 2-methyl-1-(3-phenylpropanoylamino)propylphosphinic acid (162 mg, 82%). This compound was subjected to the measurement of molecular weight and then used in the following reaction without further purification.

TSPMS (m/z): 270(M$^+$+1).

(b) Under an argon atmosphere, a dichloromethane (15 ml) solution of the 2-methyl-1-(3-phenylpropanoylamino)propylphosphinic acid (162 mg) obtained in the above step (a) was added with benzyl (S)-6-benzyloxycarbonylamino-2-hydroxyhexanoate (228 mg) which was obtained from 6-amino-2-hydroxyhexanoic acid described in Chem. Pharm. Bull., 621(1976) in a conventional manner, N-(dimethylaminopropyl)-N'-ethylcarbodiimide hydrochloride (180 mg), and dimethylaminopyridine (38.7 mg), and then the mixture was stirred at room temperature for 16 hours. The organic substances were extracted with ethyl acetate, and the extract was washed with saturated brine and dried over anhydrous magnesium sulfate. The solvent was evaporated, and the residue was purified by silica gel column chromatography (10 g, chloroform:methanol=10:1) to obtain benzyl (S)-6-(benzyloxycarbonylamino)-2-((2-methyl-1-(3-phenylpropanoylamino)propyl)phosphinoyloxy)hexanoate (117 mg, 31%). This compound was subjected to the measurement of molecular weight and then used in the following reaction.

TSPMS(m/z): 623(M$^+$+1).

(c) The benzyl (S)-6-(benzyloxycarbonylamino)-2-((2-methyl-1-(3-phenylpropanoylamino)propyl)phosphinoyloxy)hexanoate (117 mg) obtained in the above step (b) was dissolved in a mixed solvent of dioxane (4.5 ml) and water (1.5 ml) and added with sodium periodate (40.4 mg), and then the mixture was stirred at room temperature for 15 hours. The organic substances were extracted with ethyl acetate, and the extract was washed with saturated aqueous sodium thiosulfate and saturated brine, successively, and dried over anhydrous magnesium sulfate. Then the solvent was evaporated to obtain benzyl (S)-6-(benzyloxycarbonylamino)-2-((2-methyl-1-(3-phenylpropanoylamino)propyl)(hydroxyphosphinoyl)oxy)hexanoate (100.8 mg, 84%). This compound was subjected to the measurement of molecular weight and then used in the following reaction without further purification.

TSPMS(m/z): 639(M$^+$+1).

(d) The benzyl (S)-6-(benzyloxycarbonylamino)-2-((2-methyl-1-(3-phenylpropanoylamino)propyl)(hydroxyphosphinoyl)oxy)hexanoate (85 mg) obtained in the above step (c) was dissolved in a mixed solvent of dioxane (2.4 ml) and water (0.8 ml) and added with palladium hydroxide (45.8 mg), and the mixture was stirred under a hydrogen atmosphere at room temperature for 24 hours. The reaction mixture was filtered with celite and the filtrate was concentrated. The residue was purified with HP-20 (Diaion, 10 cc, methanol:water=1:4 to 1:1) to obtain the title compound: (S)-6-amino-2-((2-methyl-1-(3-phenylpropanoylamino)propyl)(hydroxyphosphinoyl)oxy)hexanoic acid (25 mg, 45%) (a diastereoisomeric mixture of 1:1).

$^1$H-NMR(D$_2$O): δ0.56(3/2H,d), 0.59(3H,m), 0.66(3/2H,d), 1.2–1.5(2H,m), 1.6–1.8(4H,m), 1.8–2.0(1H,m), 2.5–2.7(2H,m), 2.8–3.0(4H,m), 3.7–3.9(1H,m), 4.3–4.5(1H,m), 7.1–7.3(5H,m).

$^{31}$P-NMR(D$_2$O): δ18.7(1/2P,s), 19.7(1/2P,s).

TSPMS(m/z): 415(M$^+$+1).

Example 3

(S)-6-Amino-2-((2-ethyl-1-(3-phenylpropanoylamino)butyl)(hydroxyphosphinoyl)oxy)hexanoic acid In the same manner as the method of Example 2, the title compound: (S)-6-amino-2-((2-ethyl-1-(3-phenylpropanoylamino)butyl)(hydroxyphosphinoyl)oxy)hexanoic acid (a diastereoisomeric mixture of 1:1) was obtained by using 1-amino-2-ethylbutylphosphinic acid as a starting material.

$^1$H-NMR(D$_2$O): δ0.5–0.8(8H,m), 1.0–1.2(1H,m), 1.2–1.8(8H,m), 2.4–2.7(2H,m), 2.7–3.0(4H,m), 3.9–4.1(1H,m), 4.3–4.5(1H,m), 7.1–7.3(5H,m).

$^{31}$P-NMR(D$_2$O): δ19.5(1/2P,s), 20.6(1/2P,s).

TSPMS(m/z): 443(M$^+$+1).

Example 4

(S)-6-Amino-2-((1-(3-phenylpropanoylamino)ethyl)(hydroxyphosphinoyl)oxy)hexanoic acid In the same manner as the method of Example 2, the title compound: (S)-6-amino-2-((1-(3-phenylpropanoylamino)ethyl)(hydroxyphosphinoyl)oxy)hexanoic acid (a diastereoisomeric mixture of 1:1) was obtained by using 1-aminoethylphosphinic acid as a starting material.

$^1$H-NMR(D$_2$O): δ0.92(3/2H,dd), 0.95(3/2H,dd), 1.2–1.4(2H,m), 1.5–1.8(4H,m), 2.3–2.5(2H,m), 2.7–3.0(4H,m), 3.7–4.0(1H,m), 4.5–4.7(1H,m), 7.1–7.3(5H,m).

$^{31}$P-NMR(D$_2$O): δ20.4(1/2P,s), 20.8(1/2P,s).

TSPMS(m/z): 387(M$^+$+1).

Example 5

(S)-6-Amino-2-(((3-phenylpropanoylamino)methyl)(hydroxyphosphinoyl)oxy)hexanoic acid In the same manner as the method of Example 2, the title compound: (S)-6-amino-2-(((3-phenylpropanoylamino)methyl)(hydroxyphosphinoyl)oxy)hexanoic acid was obtained by using aminomethylphosphinic acid as a starting material.

$^1$H-NMR(D$_2$O): δ1.2–1.4(2H,m), 1.4–1.7(4H,m), 2.44 (2H,t), 2.78(2H,t), 2.85(2H,t), 3.1–3.3(2H,m), 4.3–4.4(1H, m), 7.1–7.3(5H,m).
TSPMS(m/z): δ373(M$^+$+1).

Example 6

(S)-6-Amino-2-((1-cyclopropyl(3-phenylpropanoylamino)methyl)(hydroxyphosphinoyl)oxy)hexanoic acid In the same manner as the method of Example 2, the title compound: (S)-6-amino-2-((1-cyclopropyl(3-phenylpropanoylamino)methyl)(hydroxyphosphinoyl)oxy)hexanoic acid (a diastereoisomeric mixture of 1:1) was obtained by using 1-amino-1-cyclopropylmethylphosphinic acid as a starting material.

$^1$H-NMR(D$_2$O): δ–0.1–0.2(2H,m), 0.2–0.4(1H,m), 0.4–0.6(1H,m), 0.8–1.1(1H,m), 1.3–1.6(2H,m), 1.6–1.9(4H, m), 2.5–2.7(2H,m), 2.8–3.1(4H,m), 3.45(0.5H,dd), 3.56 (0.5H,dd), 4.4–4.6(1H,m), 7.2–7.5(5H,m).
$^{31}$P-NMR(D$_2$O): δ15.6(1/2P,s), 16.4(1/2P,s).
TSPMS(m/z): 413(M$^+$+1).

Example 7

(S)-5-Amino-2-((2-methyl-1-(3-phenylpropanoylamino)propyl)(hydroxyphosphinoyl)oxy)pentanoic acid In the same manner as the method of Example 2, the title compound: (S)-5-amino-2-((2-methyl-1-(3-phenylpropanoylamino)propyl)(hydroxyphosphinoyl)oxy)pentanoic acid (a diastereoisomeric mixture of 1:1) was obtained by using benzyl (S)-5-benzyloxycarbonylamino-2-hydroxypentanoate instead of benzyl (S)-6-benzyloxycarbonylamino-2-hydroxyhexanoate in (b) of Example 2.

$^1$H-NMR(D$_2$O): δ0.50(3/2H,d), 0.52(3H,d), 0.58(3/2H, d), 1.4–1.7(4H,m), 1.86(1H,m), 2.5(2H,m), 2.76–2.99(4H, m), 3.72(1H,dd), 4.37(1H,m), 7.1–7.2(5H,m).
$^{31}$P-NMR(D$_2$O): δ18.81(1/2P,s), 18.82(1/2P,s).
TSPMS(m/z): 401(M$^+$+1).

Example 8

(S)-6-Amino-2-((1-(3-phenylpropanoylamino)butyl)(hydroxyphosphinoyl)oxy)hexanoic acid In the same manner as the method of Example 2, the title compound: (S)-6-amino-2-((1-(3-phenylpropanoylamino)butyl)(hydroxyphosphinoyl)oxy)hexanoic acid (a diastereoisomeric mixture of 1:1) was obtained by using 1-aminobutylphosphinic acid as a starting material.

$^1$H-NMR(D$_2$O): δ0.7–0.8(3H,m), 0.8–1.0(2H,m), 1.2–1.3 (1H,m), 1.3–1.9(7H,m), 2.6–2.7(2H,m), 2.9–3.1(4H,m), 3.9–4.0(1H,m), 4.4–4.6(1H,m), 7.2–7.4(5H,m).
$^{31}$P-NMR(D$_2$O): δ19.5(1/2P,s), 20.2(1/2P,s).
TSPMS(m/z): 415(M$^+$+1).

Example 9

(S)-6-Amino-2-((1-cyclohexyl-1-(3-phenylpropanoylamino)methyl)(hydroxyphosphinoyl)oxy)hexanoic acid In the same manner as the method of Example 2, the title compound: (S)-6-amino-2-((cyclohexyl(3-phenylpropanoylamino)methyl)(hydroxyphosphinoyl)oxy)hexanoic acid (a diastereoisomeric mixture of 1:1) was obtained by using 1-amino-1-cyclohexylmethylphosphinic acid as a starting material.

$^1$H-NMR(D$_2$O): δ0.4–0.7(2H,m), 0.8–1.0(1H,m), 1.0–1.2 (2H,m), 1.3–1.8(12H,m), 2.6–2.8(2H,m), 2.9–3.1(4H,m), 3.8–3.9(1H,m), 4.4–4.5(1H,m), 7.2–7.4(5H,m).
$^{31}$P-NMR(D$_2$O): δ18.6(1/2P,s), 19.9(1/2P,s).
TSPMS(m/z): 455(M$^+$+1).

Example 10

(S)-6-Amino-2-((1-cyclobutyl-1-(3-phenylpropanoylamino)methyl)(hydroxyphosphinoyl)oxy)hexanoic acid In the same manner as the method of Example 2, the title compound: (S)-6-amino-2-((1-cyclobutyl(3-phenylpropanoylamino)methyl)(hydroxyphosphinoyl)oxy)hexanoic acid was obtained by using 1-amino-1-cyclobutylmethylphosphinic acid as a starting material.

$^1$H-NMR(D$_2$O): δ1.3–1.6(5H,m), 1.6–1.9(7H,m), 2.5–2.7 (3H,m), 2.9–3.1(4H,m), 3.8–4.0(1H,m), 4.6–4.7(1H,m), 7.2–7.4(5H,m).
$^{31}$P-NMR(D$_2$O): δ18.5(1/2P,s), 19.1(1/2P,s).
TSPMS(m/z): 427(M$^+$+1).

Example 11

(S)-4-Amino-2-((2-methyl-1-(3-phenylpropanoylamino)propyl)(hydroxyphosphinoyl)oxy)butanoic acid In the same manner as the method of Example 2, the title compound: (S)-4-amino-2-((2-methyl-1-(3-phenylpropanoylamino)propyl)(hydroxyphosphinoyl)oxy)butanoic acid (a diastereoisomeric mixture of 1:1) was obtained by using benzyl (S)-4-benzyloxycarbonylamino-2-hydroxybutanoate instead of benzyl (S)-6-benzyloxycarbonylamino-2-hydroxyhexanoate in (b) of Example 2.

$^1$H-NMR(D$_2$O): δ0.50(3/2H,d), 0.52(3H,d), 0.58(3/2H, d), 1.8–1.9(3H,m), 2.5(2H,m), 2.8(2H,m), 2.9(2H,m), 3.79 (1H,dd), 4.38(1H,m), 7.1–7.2(5H,m).
$^{31}$P-NMR(D$_2$O): δ19.53(1/2P,s), 20.41(1/2P,s).
TSPMS(m/z): 387(M$^+$+1).

Example 12

(S)-6-Amino-2-((3-methyl-1-(3-phenylpropanoylamino)butyl)(hydroxyphosphinoyl)oxy)hexanoic acid In the same manner as the method of Example 2, the title compound: (S)-6-amino-2-((3-methyl-1-(3-phenylpropanoylamino)butyl)(hydroxyphosphinoyl)oxy)hexanoic acid (a diastereoisomeric mixture of 1:1) was obtained by using 1-amino-3-methylbutylphosphinic acid as a starting material.

$^1$H-NMR(D$_2$O): δ0.67(3H,d), 0.7–0.8(3H,m), 0.8–0.9 (1H,m), 1.3–1.6(4H,m), 1.6–1.8(2H,m), 1.8–1.9(2H,m), 2.5–2.6(2H,m), 2.8–3.0(4H,m), 3.9–4.1(1H,m), 4.6–4.7(1H, m), 7.2–7.4(5H,m).
$^{31}$P-NMR(D$_2$O): δ20.6(1/2P,s),20.9(1/2P,s).
TSPMS(m/z): 429(M$^+$+1).

Example 13

(S)-2-((2-Methyl-1-(3-phenylpropanoylamino)propyl)(hydroxyphosphinoyl)oxy)-4-ureido-butanoic acid An aqueous solution (20 ml) of the (S)-4-amino-2-((2-methyl-1-(3-phenylpropanoylamino)propyl)

(hydroxyphosphinoyl)oxy)butanoic acid (100 mg) obtained in Example 11 was added with potassium cyanate (84 mg) at room temperature and the mixture was stirred at 60° C. for 4 hours. The solvent was evaporated, and the residue was purified with HP-20 (Diaion, water:methanol=10:1) to obtain potassium salt of the title compound: (S)-2-((2-methyl-1-(3-phenylpropanoylamino)propyl)(hydroxyphosphinoyl)oxy)-4-ureido-butanoic acid (a diastereoisomeric mixture of 1:1) (95 mg).

$^1$H-NMR(D$_2$O): δ0.51(3/2H,d), 0.55(3H,d), 0.60(3/2H, d), 1.7–1.9(,3H,m), 2.5(2H,m), 2.8(2H,m), 3.0(2H,m), 3.74 (1H,dd), 4.36(1H,m), 7.1–7.2(5H,m).

TSPMS(m/z): 430(M$^+$+1).

Example 14

(S)-6-Amino-2-((1-(3-phenylpropanoylamino)cyclohexyl)(hydroxyphosphinoyl)oxy)hexanoic acid In the same manner as the method of Example 20, the title compound: (S)-6-amino-2-((1-(3-phenylpropanoylamino)cyclohexyl)(hydroxyphosphinoyl)oxy)hexanoic acid was obtained by using cyclohexanone as a starting material.

$^1$H-NMR(D$_2$O): δ0.7–0.9(2H,m), 1.0–1.1(1H,m), 1.4–1.6 (7H,m), 1.6–1.8(4H,m), 2.2–2.3(2H,m), 2.61(2H,t), 2.94 (2H,t), 3.03(2H,t), 4.4–4.5(1H,m), 7.2–7.4(5H,m).

TSPMS(m/z): 441(M$^+$+1).

Example 15

(S)-2-((2-Methyl-1-(3-phenylpropanoylamino)propyl)(hydroxyphosphinoyl)oxy)-5-ureido-pentanoic acid In the same manner as the method of Example 13, potassium salt of the title compound: (S)-2-((2-methyl-1-(3-phenylpropanoylamino)propyl)(hydroxyphosphinoyl)oxy)-5-ureido-pentanoic acid (a diastereoisomeric mixture of 1:1) was obtained by using the (S)-5-amino-2-((2-methyl-1-(3-phenylpropanoylamino)propyl)(hydroxyphosphinoyl)oxy) pentanoic acid obtained in Example 7 as a starting material.

$^1$H-NMR(D$_2$O): δ0.56(3/2H,d), 0.59(3H,d), 0.64(3/2H, d), 1.4(2H,m), 1.65(2H,brs), 1.92(1H,m), 2.59(2H,m), 2.85 (2H,m), 3.00(2H,m), 3.77(1H,dd), 4.39(1H,m), 7.1–7.3(5H, m).

TSPMS(m/z): δ444(M$^+$+1).

Example 16

(S)-6-Amino-2-((1-(3-phenylpropanoylamino)propyl)(hydroxyphosphinoyl)oxy)hexanoic acid In the same manner as the method of Example 2, sodium salt of the title compound: (S)-6-amino-2-((1-(3-phenylpropanoylamino)propyl)(hydroxyphosphinoyl)oxy) hexanoic acid (a diastereoisomeric mixture of 1:1) was obtained by using 1-aminopropylphosphinic acid as a starting material.

$^1$H-NMR(D$_2$O): δ0.5–0.7(3H,m), 1.2–1.9(8H,m), 2.5–2.7 (2H,m), 2.8–3.0(4H,m), 3.7–3.9(1H,m), 4.5–4.6(1H,m), 7.2–7.4(5H,m).

$^{31}$P-NMR(D$_2$O): δ19.2(1/2P,s), 19.9(1/2P,s).

TSPMS(m/z): 401(M$^+$+1).

Example 17

(S)-4-Guanidino-2-((2-methyl-1-(3-phenylpropanoylamino)propyl)(hydroxyphosphinoyl)oxy)butanoic acid In the same manner as the method of Example 2, the title compound: (S)-4-guanidino-2-((2-methyl-1-(3-phenylpropanoylamino)propyl)(hydroxyphosphinoyl)oxy) butanoic acid (a diastereoisomeric mixture of 1:1) was obtained by using benzyl (S)-4-(2,3-bis(benzyloxycarbonyl)guanidino)-2-hydroxybutanoate instead of benzyl (S)-6-benzyloxycarbonylamino-2-hydroxyhexanoate in (b) of Example 2.

$^1$H-NMR(D$_2$O): δ0.55(3/2H,d), 0.58(3H,d), 0.63(3/2H, d), 1.8–1.9(3H,m), 2.55(2H,m), 2.82(2H,m), 3.15(2H,m), 3.79(1H,dd), 4.39(1H,m), 7.1–7.2(5H,m).

$^{31}$P-NMR(D$_2$O): δ19.12(1/2P,s), 20.10(1/2P,s).

TSPMS(m/z): 429(M$^+$+1).

Example 18

(S)-5-Guanidino-2-((2-methyl-1-(3-phenylpropanoylamino)propyl)(hydroxyphosphinoyl)oxy)pentanoic acid In the same manner as the method of Example 2, the title compound: (S)-5-guanidino-2-((2-methyl-1-(3-phenylpropanoylamino)propyl)(hydroxyphosphinoyl)oxy) pentanoic acid (a diastereoisomeric mixture of 1:1) was obtained by using benzyl (S)-5-(2,3-bis(benzyloxycarbonyl)guanidino)-2-hydroxypentanoate instead of benzyl (S)-6-benzyloxycarbonylamino-2-hydroxyhexanoate in (b) of Example 2.

$^1$H-NMR(D$_2$O): δ0.52(3/2H,d), 0.56(3H,d), 0.61(3/2H, d), 1.5(2H,m), 1.65(2H,brs), 1.88(1H,m), 2.56(2H,m), 2.83 (2H,m), 3.07(2H,m), 3.74(1H,dd), 4.37(1H,m), 7.1–7.3(5H, m).

$^{31}$P-NMR(D$_2$O): δ18.77(1/2P,s), 19.77(1/2P,s).

TSPMS(m/z): 443(M$^+$+1).

Example 19

(S)-6-Amino-2-((2-methyl-(1R)-(3-phenylpropanoylamino)propyl)(hydroxyphosphinoyl)oxy)hexanoic acid In the same manner as the method of Example 2, the title compound: (S)-6-amino-2-((2-methyl-(1R)-(3-phenylpropanoylamino)propyl)(hydroxyphosphinoyl)oxy) hexanoic acid was obtained by using (1R)-amino-2-methylpropylphosphinic acid as a starting material.

$^1$H-NMR(D$_2$O): δ0.56(3H,d), 0.65(3H,d), 1.2–1.5(2H, m), 1.5–1.8(4H,m), 1.8–2.1(1H,m), 2.4–2.7(2H,m), 2.7–3.0 (4H,m), 3.78(1H,dd), 4.41(1H,dt), 7.1–7.3(5H,m).

Example 20

(S)-6-Amino-2-((1-(3-phenylpropanoylamino)cyclopentyl)(hydroxyphosphinoyl)oxy)hexanoic acid (a) Diphenylmethylamine (4.00 ml) and cyclopentanone (2.06 ml) were stirred at 120° C. for 3 hours, and then the mixture was returned to room temperature and added with tetrahydrofuran (2 ml) and phosphinic acid (1.8 g). The mixture was stirred at room temperature for 3 minutes, and then allowed to stand for 17 hours. Water (20 ml) was added to the reaction system, and the insoluble solid was collected by filtration and washed with tetrahydrofuran, and then dried to obtain crude 1-(diphenylmethylamino)cyclopentylphosphinic acid (1.53 g). This compound was subjected to the measurement of molecular weight and then used in the following reaction.

TSPMS(m/z): 316(M$^+$+1).

(b) The crude 1-(diphenylmethylamino)cyclopentylphosphinic acid (1.53 g) obtained in the above step (a) was added with 47% aqueous hydrobromic acid (20 ml) and stirred at 100° C. for 2 hours. The reaction product was extracted with water from the residue obtained by removing the solvent from the reaction system under reduced pressure. The aqueous layer was washed with diethyl ether and concentrated. The resulting oil was dissolved in ethanol and added with propylene oxide (3 ml) and ethyl acetate. The precipitated crystals were collected by filtration and dried to give 1-aminocyclopentylphosphinic acid (462 mg, 13%).

$^1$H-NMR(D$_2$O): δ1.6–1.8(6H,m), 2.0–2.1(2H,m), 6.83 (1H,d).

TSPMS(m/z): 150(M$^+$+1).

(c) In the same manner as the method of Example 2, the title compound: (S)-6-amino-2-((1-(3-phenylpropanoylamino)cyclopentyl)(hydroxyphosphinoyl) oxy)hexanoic acid was obtained by using the 1-aminocyclopentylphosphinic acid obtained in the above step (b) as a starting material.

$^1$H-NMR(D$_2$O): δ1.4–1.6(6H,m), 1.7–2.0(6H,m), 2.0–2.2 (2H,m), 2.55(2H,t), 2.92(2H,t), 3.02(2H,t), 4.5–4.6(1H,m), 7.2–7.4(5H,m).

TSPMS(m/z): 427(M$^+$+1).

Example 21

(S)-6-Amino-2-((2-methyl-(1S)-(3-phenylpropanoylamino)propyl) (hydroxyphosphinoyl)oxy)hexanoic acid In the same manner as the method of Example 2, the title compound: (S)-6-amino-2-((2-methyl-(1S)-(3-phenylpropanoylamino)propyl)(hydroxyphosphinoyl)oxy) hexanoic acid was obtained by using (1S)-amino-2-methylpropylphosphinic acid as a starting material.

$^1$H-NMR(D$_2$O): δ0.60(6H,d), 1.2–1.5(2H,m), 1.5–1.8 (4H,m), 1.8–2.0(1H,m), 2.5–2.7(2H,m), 2.8–3.0(4H,m), 3.79(1H,dd), 4.41(1H,dt), 7.1–7.4(5H,m).

$^{31}$P-NMR(D$_2$O): δ18.6(1P,s).

FABMS(m/Z): 415(M$^+$+1).

Example 22

6-Amino-2-((2-methyl-1-(3-phenylpropanoylamino) propyl)hydroxyphosphinoyl)methylhexanoic acid (a) 4-Amino-1-butanol (5 g) was dissolved in water (50 ml) and cooled to 0° C. The solution was added with 1 N aqueous sodium hydroxide (56.1 ml) and then with benzyl chloroformate (8 ml) and stirred at room temperature for 23 hours. 5 N aqueous sodium hydroxide (22.4 ml) and benzyl chloroformate (16 ml) were further added to the mixture, and stirring was continued for 2 hours. The reaction system was cooled to 0° C. and adjusted to pH 4 with 5 N hydrochloric acid, and the organic substances were extracted with ethyl acetate. The organic layer was concentrated under reduced pressure, and the precipitated crystals were washed with diethyl ether to obtain 4-benzyloxycarbonylamino-1-butanol (8.15 g, 65%).

$^1$H-NMR(CDCl$_3$): δ1.59(4H,m), 1.73(1H,m), 3.24(2H, dd), 3.66(2H,dd), 4.92(1H,s), 5.09(2H,s), 7.29–7.40(5H,m).

EIMS(m/z): 223(M$^+$).

(b) The 4-benzyloxycarbonylamino-1-butanol (8.15 g) obtained in the above step (a) and carbon tetrabromide (15.12 g) were dissolved in methylene chloride (130.4 ml) and cooled with water. The mixture was added with triph-enylphosphine (14.4 g) and returned to room temperature, and then stirred for 4 hours. The reaction system was concentrated under reduced pressure without any treatment, and the residue was purified by silica gel column chromatography (400 g, hexane:ethyl acetate=5:2) to obtain 1-benzyloxycarbonylamino-4-bromobutane (10.4 g, 99.5%).

$^1$H-NMR(CDCl$_3$): δ1.58–1.72(2H,m), 1.84–1.94(2H,m), 3.18–3.28(2H,dd), 3.42(2H,dd), 4.80(1H,s), 5.10(2H,s), 7.29–7.39(5H,m).

EIMS(m/z): 286(M$^+$).

(c) An ethanol (130.2 ml) solution of sodium ethoxide (5.83 g) was added with diethyl malonate (13 ml) and stirred at room temperature for 5 minutes. This solution was added with an ethanol (55.8 ml) solution of the 1-benzyloxycarbonylamino-4-bromobutane (4.9 g) obtained in the above step (b), and stirred at 40° C. for 20 hours. The reaction system was concentrated under reduced pressure without any treatment, and the residue was added with saturated aqueous ammonium chloride, and then the organic substances were extracted with ethyl acetate. The organic layer was concentrated under reduced pressure, and the residue was purified by silica gel column chromatography (1.2 kg, hexane:ethyl acetate=2:1) to obtain diethyl 2-(4-benzyloxycarbonylaminobutyl)malonate (5.2 g, 83%).

$^1$H-NMR(CDCl$_3$): δ1.26(6H,t), 1.30–1.40(2H,m), 1.48–1.58(2H,m), 1.87–1.94(2H,m), 3.19(2H,dd), 3.30(1H, dd), 4.19(4H,q), 4.83(1H,s), 5.10(2H,s), 7.28–7.38(5H,m).

FABMS(m/z): 366(M$^+$+1).

(d) An ethanol (10.2 ml) solution of the diethyl 2-(4-benzyloxycarbonylaminobutyl)malonate (3.4 g) obtained in the above step (c) was added with an ethanol (6.8 ml) solution of potassium hydroxide (584 mg), and the mixture was stirred at room temperature for 26 hours. The reaction system was concentrated under reduced pressure without any treatment, and water was added to the residue. The aqueous layer was washed with diethyl ether to remove impurities. The aqueous layer was adjusted to pH 3 with 1 N hydrochloric acid, and then the organic substances were extracted with ethyl acetate. The organic layer was concentrated under reduced pressure to obtain monoethyl 2-(4-benzyloxycarbonylaminobutyl)malonate (3.03 g, 96.5%).

$^1$H-NMR(CDCl$_3$): δ1.27(3H,t), 1.32–1.43(2H,m), 1.48–1.58(2H,m), 1.86–1.96(2H,m), 3.11–3.25(2H,m), 3.36 (1H,dd), 4.20(2H,q), 4.91(1H,s), 5.09(2H,s), 7.28–7.39(5H, m), 7.50–8.35(1H,brs).

FABMS(m/z): 338(M$^+$+1).

(e) The monoethyl 2-(4-benzyloxycarbonylaminobutyl) malonate (3.03 g) obtained in the above step (d) was cooled to 0° C. and added with 36% formaldehyde solution (3 ml) and then with diethylamine (3 ml), and then the mixture was stirred at room temperature for 19.5 hours. Ethyl acetate was added to the reaction system to extract the organic substances, and the organic layer was concentrated under reduced pressure. The residue was purified by silica gel column chromatography (150 g, hexane:acetone=5:1) to obtain ethyl 2-(4-benzyloxycarbonylaminobutyl)acrylate (1.69 g, 62%).

$^1$H-NMR(CDCl$_3$): δ1.30(3H,t), 1.47–1.56(4H,m), 2.32 (2H,t), 3.22(2H,q), 4.20(2H,q), 4.77(1H,s), 5.10(2H,s), 5.52 (1H,s), 6.14(1H,s), 7.29–7.37(5H,m).

TSPMS(m/z): 306(M$^+$+1).

(f) The 2-methyl-1-(3-phenylpropanoyl) aminopropylphosphinic acid (255 mg) obtained in (a) of Example 2 was added with hexamethyldisilazane (0.3 ml), and the mixture was stirred at 110° C. for 30 minutes. The mixture was then added with the ethyl 2-(4-benzyloxycarbonylaminobutyl)acrylate (356 mg) obtained in the above step (e), and further stirred at the same temperature for 18 hours. The organic substances were extracted with ethyl acetate, and the extract was washed with saturated brine and dried over anhydrous magnesium sulfate. The solvent was evaporated, and then the residue was purified by Sephadex LH-20 (300 cc, methylene chloride:methanol=1:1) to obtain crude ethyl 6-benzyloxycarbonylamino-2-((2-methyl-1-(3-phenylpropanoylamino)propyl)hydroxyphosphinoyl) methylhexanoate (222 mg, 41%). This compound was used in the following reaction without further purification. (g) The crude ethyl 6-benzyloxycarbonylamino-2-((2-methyl-1-(3-phenylpropanoylamino)propyl)hydroxyphosphinoyl) methylhexanoate (222 mg) obtained in the above step (f) was dissolved in a mixed solvent of ethanol:water (10:7) (3.4 ml). The mixture was added with 1 N aqueous sodium hydroxide (0.6 ml) and stirred at room temperature for 3 hours, at 50° C. for 2 hours, and then at room temperature for 16 hours. The reaction mixture was acidified with hydrochloric acid and the organic substances were extracted with ethyl acetate, and then the extract was washed with saturated brine and dried over anhydrous magnesium sulfate. The residue was concentrated to obtain crude 6-benzyloxycarbonylamino-2-((2-methyl-1-(3-phenylpropanoylamino)propyl)hydroxyphosphinoyl) methylhexanoic acid (181 mg, 86%). This compound was subjected to the measurement of molecular weight and then used in the following reaction without further purification.

TSPMS(m/Z): 547(M$^+$+1).

(h) The crude 6-benzyloxycarbonylamino-2-((2-methyl-1-(3-phenylpropanoylamino)propyl)hydroxyphosphinoyl) methylhexanoic acid (181 mg) obtained in the above step (g) was dissolved in a mixed solvent of dioxane and water (1:1) (4 ml). The solution was added with palladium hydroxide (37 mg), and the mixture was stirred under a hydrogen atmosphere at room temperature for 4 hours. The reaction mixture was filtered with celite and the filtrate was concentrated. The residue was purified with HP-20 (Diaion, 20 cc, methanol:water=1:9 to acetone:water=1:1) to obtain the title compound: 6-amino-2-((2-methyl-1-(3-phenylpropanoylamino)propyl)hydroxyphosphinoyl) methylhexanoic acid (74 mg, 54%) (a diastereoisomeric mixture of 3:1).

$^1$H-NMR(D$_2$O): δ0.6–0.8(6H,m), 1.2–1.7(8H,m), 2.0–2.2 (1H,m), 2.4–2.7(3H,m), 2.8–3.0(4H,m), 3.6–3.8(1H,m), 7.1–7.3(5H,m).

$^{31}$P-NMR(D$_2$O): δ37.9(3/4P,s), 38.3(1/4P,s).

TSPMS(m/z): 413(M$^+$+1).

Example 23

(S)-6-Amino-2-((3,3-dimethyl-1-(3-phenylpropanoylamino)butyl)(hydroxyphosphinoyl) oxy)hexanoic acid In the same manner as the method of Example 2, the title compound: (S)-6-amino-2-((3,3-dimethyl-1-(3-phenylpropanoylamino)butyl)(hydroxyphosphinoyl)oxy) hexanoic acid (a diastereoisomeric mixture of 1:1) was obtained by using 1-$^{amino}$-3,3-dimethylbutylphosphinic acid as a starting material.

1H-NMR(D$_2$O): δ0.77(9/2H,s), 0.79(9/2H,s), 1.3–1.6 (3H,m), 1.7–1.9(5H,m), 2.5–2.6(2H,m), 2.9–3.0(2H,m), 3.03(2H,t), 4.1–4.2(1H,m), 4.4–4.5(1H,m), 7.2–7.4(5H,m).

$^{31}$P-NMR(D$_2$O): δ20.1(1/2P,s), 20.8(1/2P,s).

TSPMS(m/z): 443(M$^+$+1).

Example 24

(S)-6-Amino-2-(2-methyl-1-(4-phenylbutanoylamino)propyl(hydroxyphosphinoyl) oxy)hexanoic acid (a) Benzyl (S)-6-benzyloxycarbonylamino-2-hydroxyhexanoate (3.4 g), which is obtainable from 6-amino-2-hydroxyhexanoic acid described in Chem. Pharm. Bull., 621(1976) in a conventional manner, was dissolved in dichloromethane (34 ml), and the solution was added with phosphorus trichloride (3.43 ml) at 0° C. and stirred for 1 hour. The reaction system was added with ice and further stirred for 30 minutes, and then the organic substances were extracted with ethyl acetate. The organic layer was concentrated under reduced pressure, and the residue was purified by silica gel column chromatography (170 g, hexane:ethyl acetate=1:1 to chloroform:methanol:acetic acid=2:1:0.01) to obtain benzyl 6-benzyloxycarbonylamino-2-((hydroxyphosphinoyl)oxy) hexanoate (3.68 g, 92%).

$^1$H-NMR(CDCl$_3$): δ1.20–1.55(4H,m), 1.56–1.91(2H,m), 2.97(2H,brs), 4.77(1H,brs), 4.94(1H,d), 5.16(1H,d), 5.00 (2H,s), 5.67(1H,brs), 6.88(1H,d), 7.16–7.29(10H,m).

TSPMS(m/z): 436(M$^+$+1).

(b) An acetonitrile (29.7 ml) solution of the benzyl 6-benzyloxycarbonylamino-2-((hydroxyphosphinoyl)oxy) hexanoate (2.97 g) obtained in the above step (a) was added with benzyl alcohol (3.53 ml) and a pyridine (11.9 ml)-acetonitrile (11.9 ml) mixed solution of pivaloyl chloride (4.20 ml), and the mixture was stirred at room temperature for 1 hour. Saturated aqueous ammonium chloride was added to the reaction system, and the organic substances were extracted with ethyl acetate. The organic layer was concentrated under reduced pressure, and pyridine was removed by azeotropic distillation using toluene. The residue was roughly purified by silica gel (Kanto Kagaku Co., 60 N, spherical, neutral) chromatography (300 g, hexane-:ethyl acetate=3:2) to obtain crude benzyl 6-benzyloxycarbonylamino-2-((benzyloxyphosphinoyl) oxy)hexanoate (2.45 g, 68%). This compound was subjected to the measurement of molecular weight and then used in the following reaction without further purification.

TSPMS(m/z): 526(M$^+$+1).

(c) Isobutylaldehyde (2.8 ml) was dissolved in tetrahydrofuran (10 ml), and the solution was added with 4-methoxybenzylamine (1 ml) and then stirred at 60° C. for 2 hours. The imine generation was observed by $^1$H-NMR, and then the reaction mixture was concentrated under reduced pressure to obtain crude (4-methoxybenzyl)-N-(2-methylpropylidene)amine.

$^1$H-NMR(CDCl$_3$): δ1.10(6H,d), 2.43–2.56(1H,m), 3.79 (3H,s), 4.49(2H,s), 6.86(2H,d), 7.17(2H,d), 7.63(1H,dt).

(d) To the crude benzyl 6-benzyloxycarbonylamino-2-((benzyloxyphosphinoyl)oxy)hexanoate (192.5 mg) obtained in the above step (b), a tetrahydrofuran (5.4 ml) solution of the crude (4-methoxybenzyl)-N-(2-methylpropylidene)amine obtained in (c) above was added, and the mixture was stirred at room temperature for 21 hours. To the reaction system, 10% aqueous citric acid was added, and then the organic substances were extracted with ethyl acetate. The organic layer was concentrated under reduced pressure, and then the residue was roughly purified by silica gel (Kanto Kagaku Co. 60 N, spherical, neutral) chromatography (20 g, hexane:acetone=2:1) to obtain crude benzyl (S)-6-benzyloxycarbonylamino-2-((1-((4-methoxy)benzylamino)-2-methylpropyl)(benzyloxyphosphinoyl)oxy)hexanoate (176.2 mg, 67%). This compound was subjected to the measurement of molecular weight and then used in the following reaction without further purification.

FABMS(m/z): 717(M$^+$+1).

(e) The crude benzyl (S)-6-benzyloxycarbonylamino-2-((1-((4-methoxy)benzylamino)-2-methylpropyl)(benzyloxyphosphinoyl)oxy)hexanoate (557.4 mg) obtained in the above step (d) was dissolved in a mixed solvent of acetonitrile and water (4:1) (5.6 ml). Cerium(IV) diammonium nitrate was dissolved in a mixed solvent of acetonitrile and water (4:1) (5.6 ml), and the resulting solution was added to the reaction system. The mixture was stirred at room temperature for 1.5 hours. The mixture was cooled to 0° C. and added with saturated aqueous sodium thiosulfate, and further stirred at room temperature for 30 minutes. The organic substances were extracted with ethyl acetate, and the organic layer was concentrated under reduced pressure, and then the residue was roughly purified by silica gel column chromatography (25 g, hexane:ethyl acetate:acetic acid=250:50:1.5 to chloroform:methanol=30:1) to obtain crude benzyl (S)-2-((1-amino-2-methylpropyl)(benzyloxyphosphinoyl)oxy)-6-benzyloxycarbonylaminohexanoate (271 mg, 62%). This compound was examined in the molecular weight and then used in the following reaction without further purification.

ESIMS(m/z): 597(M$^+$+1).

(f) 4-Phenylbutanoic acid (58.2 mg) was dissolved in methylene chloride (1 ml), and the solution was added with diisopropylethylamine (92.6 ml) and benzotriazol-1-yloxytris(dimethylamino)phosphonium hexafluorophophate and then stirred at room temperature for 7 minutes. The crude benzyl (S)-2-((1-amino-2-methylpropyl)(benzyloxyphosphinoyl)oxy)-6-benzyloxycarbonylaminohexanoate (105.7 mg) obtained in the above step (e) was dissolved in methylene chloride (640 ml), and the reaction mixture was added with the above solution and stirred at room temperature for 22 hours. Saturated aqueous ammonium chloride was added to the reaction mixture, and the organic substances were extracted with ethyl acetate, and then the organic layer was concentrated under reduced pressure. The residue was roughly purified by thin-layer chromatography to obtain benzyl (S)-6-benzyloxycarbonylamino-2-((2-methyl-1-(4-phenylbutanoylamino)propyl)(benzyloxyphosphinoyl)oxy)hexanoate (43.9 mg, 33%). This compound was subjected to the measurement of molecular weight and then used in the following reaction without further purification.

TSPMS(m/z): 743(M$^+$+1).

(g) The benzyl (S)-6-benzyloxycarbonylamino-2-((2-methyl-1-(4-phenylbutanoylamino)propyl)(benzyloxyphosphinoyl)oxy)hexanoate (43.9 mg) obtained in the above step (f) was dissolved in a mixed solvent of dioxane and water (3:1) (439 ml), and the solution was added with palladium hydroxide (8.8 mg) and stirred under a hydrogen atmosphere at room temperature for 18 hours. The reaction mixture was filtered with celite, and the filtrate was concentrated under reduced pressure. The residue was purified by HP-20 (Diaion, 5 g, water to methanol) to obtain the title compound: (S)-6-amino-2-(2-methyl-1-(4-phenylbutanoylamino)propyl(hydroxyphosphinoyl)oxy)hexanoic acid (17.5 mg, 70%, a diastereoisomeric mixture of 1:1).

1H-NMR(D$_2$O): δ0.74–0.86(6H,m), 1.16–1.41(2H,m), 1.45–1.59(2H,m), 1.59–1.67(2H,m), 1.73–1.84(2H,m), 1.90–2.07(1H,m), 2.12–2.27(2H,m), 2.49–2.57(2H,m), 2.83(2H,q), 3.37–3.89(1H,m), 4.32–4.42(1H,m), 7.10–7.26(5H,m).

$^{31}$P-NMR(D$_2$O): δ18.64(1/2P,s), 19.62(1/2P,s).

FABMS(m/z): 429(M$^+$+1).

Example 25

(S)-6-Amino-2-((4,4,4-trifluoro-1-(3-phenylpropanoylamino)butyl)(hydroxyphosphinoyl)oxy)hexanoic acid In the same manner as the method of Example 2, the title compound: (S)-6-amino-2-((4,4,4-trifluoro-1-(3-phenylpropanoylamino)butyl)(hydroxyphosphinoyl)oxy)hexanoic acid (a diastereoisomeric mixture of 1:1) was obtained by using 1-amino-4,4,4-trifluorobutylphosphinic acid as a starting material.

1H-NMR(D$_2$O): δ1.4–1.9(9H,m), 1.9–2.0(1H,m), 2.6–2.7(2H,m), 2.9–3.1(4H,m), 3.9–4.0(1H,m), 4.5–4.6(1H,m), 7.2–7.4(5H,m).

$^{31}$P-NMR(D$_2$O): δ17.7(1/2P,s), 18.4(1/2P,s).

TSPMS(m/z): 469(M$^+$+1).

Example 26

(S)-6-Amino-2-((2-methyl-1-(3-phenylpropanoylamino)propyl)(hydroxyphosphinoyl)oxy)hexanoic acid In the same manner as the method of Example 24, the title compound: (S)-6-amino-2-((2-methyl-1-(3-phenylpropanoylamino)propyl)(hydroxyphosphinoyl)oxy)hexanoic acid was obtained by using 3-phenylpropanoic acid instead of 4-phenylbutanoic acid used in the step (f) of Example 24. The spectrum data of the resulting compound showed similar values to those of the compound obtained in Example 2.

$^1$H-NMR(D$_2$O): δ0.56(3/2H,d), 0.59(3H,m), 0.66(3/2H,d), 1.2–1.5(2H,m), 1.6–1.8(4H,m), 1.8–2.0(1H,m), 2.5–2.7(2H,m), 2.8–3.0(4H,m), 3.7–3.9(1H,m), 4.3–4.5(1H,m), 7.1–7.3(5H,m).

$^{31}$P-NMR(D$_2$O): δ18.7(1/2P,s), 19.7(1/2P,s).

TSPMS(m/z): 415(M$^+$+1).

Example 27

(S)-7-Amino-2-((1-(3-phenylpropanoylamino)cyclopentyl)(hydroxyphosphinoyl)oxy)heptanoic acid In the same manner as the method of Example 2, the title compound: (S)-7-amino-2-((1-(3-phenylpropanoylamino)cyclopentyl)(hydroxyphosphinoyl)oxy)heptanoic acid was obtained by using benzyl (S)-7-benzyloxycarbonylamino-2-hydroxyheptanoate instead of benzyl (S)-6-benzyloxycarbonylamino-2-hydroxyhexanoate used in the step (b) of Example 2, and using the 1-aminocyclopentylphosphinic acid obtained in the step (b) of Example 20.

$^1$H-NMR(D$_2$O): δ1.25–1.34(6H,m), 1.45(2H,m), 1.55(2H,m), 1.65(2H,m), 1.78(2H,m), 1.93(2H,m), 2.44(2H,m), 2.79(2H,m), 2.89(2H,m), 4.40(1H,m), 7.15–7.27(5H,m).

$^{31}$P-NMR(D$_2$O): δ23.41(1P,s).

TSPMS(m/z): 441(M$^+$+1).

Example 28

(R)-7-Amino-2-((1-(3-phenylpropanoylamino)cyclopentyl)(hydroxyphosphinoyl)oxy)heptanoic acid In the same manner as the method of Example 2, the title compound: (R)-7-amino-2-((1-(3-phenylpropanoylamino)cyclopentyl)(hydroxyphosphinoyl)oxy)heptanoic acid was obtained by using benzyl (R)-7-benzyloxycarbonylamino-2-hydroxyheptanoate instead of benzyl (S)-6-benzyloxycarbonylamino-2-hydroxyhexanoate used in the step (b) of Example 2, and using the 1-aminocyclopentylphosphinic acid obtained in (b) of Example 20.

$^1$H-NMR(D$_2$O): δ1.25–1.34(6H,m), 1.45(2H,m), 1.55 (2H,m), 1.65(2H,m), 1.78(2H,m), 1.93(2H,m), 2.44(2H,m), 2.79(2H,m), 2.89(2H,m), 4.40(1H,m), 7.15–7.27(5H,m).

$^{31}$P-NMR(D$_2$O): δ23.41(1P,s).

TSPMS(m/z): 441(M$^+$+1).

Example 29

(S)-7-Amino-2-((2-methyl-(1R)-(3-phenylpropanoylamino)propyl)(hydroxyphosphinoyl)oxy)heptanoic acid In the same manner as the method of Example 2, the title compound: (S)-7-amino-2-((2-methyl-(1R)-(3-phenylpropanoylamino)propyl)(hydroxyphosphinoyl)oxy)heptanoic acid was obtained by using (1R)-amino-2-methylphosphinic acid instead of amino-2-methylphosphinic acid used in the step (a) of Example 2, and using benzyl (S)-7-benzyloxycarbonylamino-2-hydroxyheptanoate instead of benzyl (S)-6-benzyloxycarbonylamino-2-hydroxyhexanoate used in the step (b) of Example 2.

$^1$H-NMR(D$_2$O): δ0.61(6H,m), 1.24–1.32(4H,m), 1.55 (4H,m), 1.93(1H,m), 2.53(2H,m), 2.83(4H,m), 3.75(1H,dd), 4.38(1H,m), 7.13–7.27(5H,m).

$^{31}$P-NMR(D$_2$O): δ19.56(1P,s).

TSPMS(m/z): 429(M$^+$+1).

Example 30

2-(2-Methyl-(1R)-(3-phenylpropanoylamino)propyl(hydroxyphosphinoyl)oxy)-4-(piperidin-4-yl)butanoic acid In the same manner as the method of Example 2, the title compound: 2-(2-methyl-(1R)-(3-phenylpropanoylamino)propyl(hydroxyphosphinoyl)oxy)-4-(piperidin-4-yl)butanoic acid (a diastereoisomeric mixture of 1:1) was obtained by using (1R)-amino-2-methylphosphinic acid instead of amino-2-methylphosphinic acid used in the step (a) of Example 2, and using benzyl 4-(1-benzyloxycarbonylpiperidin-4-yl)-2-hydroxybutanoate instead of benzyl (S)-6-benzyloxycarbonylamino-2-hydroxyhexanoate used in the step (b) of Example 2.

$^1$H-NMR(D$_2$O): δ0.53–0.63(6H,m), 1.27(4H,m), 1.48 (1H,m), 1.64(2H,m), 1.84(3H,m), 2.57(2H,m), 2.84(4H,m), 3.25(2H,m), 2.72(1H,m), 4.37(1H,brs), 7.14–7.27(5H,m).

$^{31}$P-NMR(D$_2$O): δ18.49(1/2P,s), 19.50(1/2P,s).

TSPMS(m/z): 455(M$^+$+1).

Example 31

1-(trans-(4-Aminomethylcyclohexyl))-1-(2-methyl-(1R)-(3-phenylpropanoylamino)propyl(hydroxyphosphinoyl)oxy)acetic acid In the same manner as the method of Example 2, the title compound: 1-(trans-(4-aminomethylcyclohexyl))-1-(2-methyl-(1R)-(3-phenylpropanoylamino)propyl(hydroxyphosphinoyl)oxy)acetic acid (a diastereoisomeric mixture of 1:1) was obtained by using (1R)-amino-2-methylphosphinic acid instead of amino-2-methylphosphinic acid used in the step (a) of Example 2, and using 1-trans-(4-(benzyloxycarbonylaminomethyl)cyclohexyl)-1-hydroxyacetic acid instead of benzyl (S)-6-benzyloxycarbonylamino-2-hydroxyhexanoate in (b) of Example 2.

$^1$H-NMR(D$_2$O): δ0.53–0.66(6H,m), 0.92(2H,m), 1.16 (2H,m), 1.49–1.94(7H,m), 2.58(2H,m), 2.74–2.87(4H,m), 3.75(1H,m), 4.24(1H,m), 7.16(5H,m).

$^{31}$P-NMR(D$_2$O): δ19.12(1/2P,s), 20.10(1/2P,s).

TSPMS(m/z): 455(M$^+$+1).

Example 32

3-Aminoacetoxy-2-(2-methyl-(1R)-(3-phenylpropanoylamino)propyl(hydroxyphosphinoyl)oxy)propanoic acid In the same manner as the method of Example 2, the title compound: 3-aminoacetoxy-2-(2-methyl-(1R)-(3-phenylpropanoylamino)propyl(hydroxyphosphinoyl)oxy)propanoic acid (a diastereoisomeric mixture of 1:1) was obtained by using (1R)-amino-2-methylphosphinic acid instead of amino-2-methylphosphinic acid used in the step (a) of Example 2, and using benzyl 3-benzyloxycarbonylaminoacetoxy-2-hydroxypropanoate instead of benzyl (S)-6-benzyloxycarbonylamino-2-hydroxyhexanoate used in the step (b) of Example 2.

$^1$H-NMR(D$_2$O): δ0.54–0.64(6H,m), 2.55(2H,m), 2.86 (2H,m), 3.78(3H,m), 3.99(2H,m), 4.35(1H,m), 7.14–7.28 (5H,m).

$^{31}$P-NMR(D$_2$O): δ18.77(1/2P,s), 19.77(1/2P,s).

TSPMS(m/z): 431(M$^+$+1).

Example 33

8-Amino-2-(2-methyl-(1R)-(3-phenylpropanoylamino)propyl(hydroxyphosphinoyl)oxy)octanoic acid In the same manner as the method of Example 2, the title compound: 8-amino-2-(2-methyl-(1R)-(3-phenylpropanoylamino)propyl(hydroxyphosphinoyl)oxy)octanoic acid (a diastereoisomeric mixture of 1:1) was obtained by using (1R)-amino-2-methylphosphinic acid instead of amino-2-methylphosphinic acid used in the step (a) of Example 2, and using benzyl 8-benzyloxycarbonylamino-2-hydroxyoctanoate instead of benzyl (S)-6-benzyloxycarbonylamino-2-hydroxyhexanoate used in the step (b) of Example 2.

$^1$H-NMR(D$_2$O): δ0.52–0.63(6H,m), 1.15–1.24(6H,m), 1.51(4H,m), 1.91(1H,m), 2.55(2H,m), 2.83(4H,m), 3.74 (1H,m), 4.38(1H,m), 7.13–7.27(5H,m).

$^{31}$P-NMR(D$_2$O): δ18.52(1/2P,s), 19.52(1/2P,s).

TSPMS(m/z): 443(M$^+$+1).

Example 34

(S)-6-Amino-2-((1-phenyl-1-(3-phenylpropanoylamino)methyl)(hydroxyphosphinoyl)oxy)hexanoic acid In the same manner as the method of Example 2, the title compound: (S)-6-amino-2-((1-phenyl-1-(3- phenylpropanoylamino)methyl)(hydroxyphosphinoyl)oxy)hexanoic acid (a diastereoisomeric mixture of 3:5) was obtained by using 1-amino-1-phenylmethylphosphinic acid as a starting material.

$^1$H-NMR(D$_2$O): δ1.3–1.5(2H,m), 1.6–1.8(4H,m), 2.6–2.8(2H,m), 2.8–3.0(4H,m), 4.0–4.1(1H,m), 4.4–4.5(1H,m), 7.1–7.3(10H,m).

$^{31}$P-NMR(D$_2$O): δ15.1(3/8P,s), 16.2(5/8P,s).

TSPMS(m/z): 449(M$^+$+1).

Example 35

(S)-6-Amino-2-((1-(3-phenylpropanoylamino)-1-(tetrahydropyran-4-yl)methyl)(hydroxyphosphinoyl)oxy)hexanoic acid In the same manner as the method of Example 2, the title compound: (S)-6-amino-2-((1-(3-phenylpropanoylamino)-1-(tetrahydropyran-4-yl)methyl)(hydroxyphosphinoyl)oxy)hexanoic acid (a diastereoisomeric mixture of 1:1) was obtained by using 1-amino-1-(tetrahydropyran-4-yl)methylphosphinic acid as a starting material.

$^1$H-NMR(D$_2$O): δ0.8–1.1(2H,m), 1.3–1.6(4H,m), 1.6–2.0(5H,m), 2.6–2.8(2H,m), 2.9–3.1(4H,m), 3.2–3.4(2H,m), 3.7–3.9(3H,m), 4.5–4.6(1H,m), 7.2–7.4(5H,m).

$^{31}$P-NMR(D$_2$O): δ17.4(1/2P,s), 18.6(1/2P,s).

FABMS(m/z): 457(M$^+$+1).

Example 36

(S)-5-Amino-2-((3-methyl-1-(3-phenylpropanoylamino)butyl)(hydroxyphosphinoyl)oxy)pentanoic acid In the same manner as the method of Example 2, the title compound: (S)-5-amino-2-((3-methyl-1-(3-phenylpropanoylamino)butyl)(hydroxyphosphinoyl)oxy)pentanoic acid (a diastereoisomeric mixture of 1:1) was obtained by using 1-amino-3-methylbutylphosphinic acid as a starting material, and using benzyl (S)-5-benzyloxycarbonylamino-2-hydroxypentanoate instead of benzyl (S)-6-benzyloxycarbonylamino-2-hydroxyhexanoate in (b) of Example 2.

$^1$H-NMR(D$_2$O): δ0.7–0.8(6H,m), 0.8–0.9(1H,m), 1.2–1.5(2H,m), 1.7–1.9(4H,m), 2.6–2.7(2H,m), 2.9–3.1(4H,m), 4.0–4.1(1H,m), 4.5–4.6(1H,m), 7.3–7.4(5H,m).

$^{31}$P-NMR(D$_2$O): δ20.1(1/2P,s), 20.7(1/2P,s).

TSPMS(m/z): 415(M$^+$+1).

Example 37

(S)-6-Amino-2-((2-hydroxy-1-(3-phenylpropanoylamino)ethyl)(hydroxyphosphinoyl)oxy)hexanoic acid In the same manner as the method of Example 2, the title compound: (S)-6-amino-2-((2-hydroxy-1-(3-phenylpropanoylamino)ethyl)(hydroxyphosphinoyl)oxy)hexanoic acid (a diastereoisomeric mixture of 1:1) was obtained by using 1-amino-2-benzyloxyethylphosphinic acid as a starting material.

$^1$H-NMR(D$_2$O): δ1.4–1.6(2H,m), 1.6–1.9(4H,m), 2.6–2.7(2H,m), 2.9–3.1(4H,m), 3.5–3.7(1H,m), 3.7–3.9(1H,m), 4.1–4.2(1H,m), 4.5–4.6(1H,m), 7.3–7.4(5H,m).

$^{31}$P-NMR(D$_2$O): δ15.9(1/2P,s), 16.4(1/2P,s).

TSPMS(m/z): 403(M$^+$+1).

Example 38

(S)-6-Amino-2-((1-cycloheptyl-1-(3-phenylpropanoylamino)methyl)(hydroxyphosphinoyl)oxy)hexanoic acid In the same manner as the method of Example 2, the title compound: (S)-6-amino-2-((1-cycloheptyl-1-(3-phenylpropanoylamino)methyl)(hydroxyphosphinoyl)oxy)hexanoic acid (a diastereoisomeric mixture of 1:1) was obtained by using 1-amino-1-cycloheptylmethylphosphinic acid as a starting material.

$^1$H-NMR(D$_2$O): δ0.7–1.0(2H,m), 1.2–1.9(17H,m), 2.6–2.8(2H,m), 2.9–3.1(4H,m), 3.8–4.0(1H,m), 4.4–4.5(1H,m), 7.3–7.4(5H,m).

$^{31}$P-NMR(D$_2$O): δ18.8(1/2P,s), 19.7(1/2P,s).

TSPMS(m/z): 469(M$^+$+1).

Example 39

(S)-6-Amino-2-((1-(piperidin-4-yl)-1-(3-phenylpropanoylamino)methyl)(hydroxyphosphinoyl)oxy)hexanoic acid In the same manner as the method of Example 2, the title compound: (S)-6-amino-2-((1-(piperidin-4-yl)-1-(3-phenylpropanoylamino)methyl)(hydroxyphosphinoyl)oxy)hexanoic acid (a diastereoisomeric mixture of 1:1) was obtained by using 1-amino-1-(1-(4-nitrobenzyloxcarbonyl)piperidin-4-yl)methylphosphinic acid as a starting material.

$^1$H-NMR(D$_2$O): δ0.9–1.5(5H,m), 1.5–2.0(6H,m), 2.6–2.9(4H,m), 2.9–3.0(4H,m), 3.1–3.3(2H,m), 3.8–3.9(1H,m), 4.4–4.5(1H,m), 7.3–7.4(5H,m).

$^{31}$P-NMR(D$_2$O): δ16.7(1/2P,s), 17.8(1/2P,s).

TSPMS(m/z): 456(M$^+$+1).

Example 40

(S)-6-Amino-2-((4-amino-1-(3-phenylpropanoylamino)butyl)(hydroxyphosphinoyl)oxy)hexanoic acid In the same manner as the method of Example 2, the title compound: (S)-6-amino-2-((4-amino-1-(3-phenylpropanoylamino)butyl)(hydroxyphosphinoyl)oxy)hexanoic acid (a diastereoisomeric mixture of 4:5) was obtained by using 1-amino-4-(4-nitrobenzyloxycarbonyl)aminobutylphosphinic acid as a starting material.

$^1$H-NMR(D$_2$O): δ1.1–1.6(5H,m), 1.6–1.8(5H,m), 2.6–2.7(4H,m), 2.9–3.0(4H,m), 3.9–4.0(1H,m), 4.5–4.6(1H,m), 7.3–7.4(5H,m).

$^{31}$P-NMR(D$_2$O): δ18.3(4/9P,s), 19.0(5/9P,s).

TSPMS(m/z): 430(M$^+$+1).

Example 41

(S)-6-Amino-2-((1-(4-methylcyclohexyl)-1-(3-phenylpropanoylamino)methyl)(hydroxyphosphinoyl)oxy)hexanoic acid In the same manner as the method of Example 2, the title compound: (S)-6-amino-2-(1-(4-methylcyclohexyl)-1-(3-phenylpropanoylamino)methyl)(hydroxyphosphinoyl)oxy)hexanoic acid (a diastereoisomeric mixture of 1:1) was obtained by using 1-amino-1-(4-methylcyclohexyl)methylphosphinic acid as a starting material.

$^1$H-NMR(D$_2$O): δ0.4–0.9(7H,m), 1.0–1.1(1H,m), 1.3–1.8(11H,m), 2.6–2.8(2H,m), 2.9–3.1(4H,m), 3.8–3.9(1H,m), 4.4–4.5(1H,m), 7.2–7.4(5H,m).

$^{31}$P-NMR(D$_2$O): δ18.7(1/2P,s), 19.9(1/2P,s).

TSPMS(m/z): 469(M$^+$+1).

Example 42

(S)-6-Amino-2-(((1R)-((2S)-amino-3-phenylpropanoylamino)-2-methylpropyl)(hydroxyphosphinoyl)oxy)hexanoic acid (a) N-Benzyloxycarbonyl-L-phenylalanine (56.3 mg) and the crude benzyl (S)-2-((1-amino-2-methylpropyl)

(benzyloxyphosphinoyl)oxy)-6-benzyloxycarbonylaminohexanoate (93.6 mg) obtained in (e) of Example 24 were dissolved in methylene chloride (1.5 ml), and the solution was added with diisopropylethylamine (54.6 ml) and benzotriazol-1-yloxy-tris(dimethylamino) phosphonium hexafluorophosphate (83.3 mg). The mixture was stirred under an argon atmosphere at room temperature for 22 hours. Saturated aqueous sodium chloride was added to the reaction system, and then the organic substances were extracted with ethyl acetate. The organic layer was concentrated under reduced pressure, and the residue was purified by thin-layer chromatography (chloroform:acetone=5:1) to obtain benzyl (S)-2-(1-(((2S)-benzyloxyamino-3-phenylpropanoylamino)-2-methylpropyl)(benzyloxyphosphinoyl)oxy)-6-benzyloxycarbonylaminohexanoate (105.8 mg, 76.8%). This compound was subjected to the measurement of molecular weight and then used in the following reaction without further purification.

TSPMS(m/z): 878(M$^+$+1).

(b) The benzyl (S)-2-(1-(((2S)-benzyloxyamino-3-phenylpropanoylamino)-2-methylpropyl)(benzyloxyphosphinoyl)oxy)-6-benzyloxycarbonylaminohexanoate (28.8 mg) obtained in the above step (a) was dissolved in a mixed solvent of dioxane:water=3:1 (288 ml), and the solution was added with palladium hydroxide (5.8 mg) and then stirred under a hydrogen atmosphere at room temperature for 17 hours. The reaction mixture was filtered with celite, and the filtrate was concentrated under reduced pressure. The residue was purified by thin-layer chromatography (ethyl acetate:methanol:water=2:2:1) and HP20 (Diaion, water to methanol) to obtain the title compound: (S)-6-amino-2-(((1R)-((2S)-amino-3-phenylpropanoylamino)-2-methylpropyl)(hydroxyphosphinoyl)oxy)hexanoic acid (7.5 mg).

$^1$H-NMR(D$_2$O): δ0.82(3H,d), 0.86(3H,d), 1.28–1.45(2H, m), 1.50–1.63(2H,m), 1.64–1.78(2H,m), 2.04–2.15(1H,m), 2.90(2H,t), 2.93(1H,dd), 3.17(1H,dd), 3.84(1H,dd), 4.09 (1H,dd), 4.34–4.41(1H,m), 7.22–7.32(5H,m).

$^{31}$P-NMR(D$_2$O): δ18.82(1P,s).

TSPMS(m/z): 430(M$^+$+1).

Example 43

(S)-6-Amino-2-((2-methyl-(1R)-phenylacetylaminopropyl)(hydroxyphosphinoyl)oxy)hexanoic acid (a) The crude benzyl (S)-2-((1-amino-2-methylpropyl)(benzyloxyphosphinoyl)oxy)-6-benzyloxycarbonylaminohexanoate (88.5 mg) obtained in the step (e) of Example 24 was dissolved in methylene chloride (1.77 ml), and the solution was added with triethylamine (41.3 μl) and phenylacetyl chloride (21.6 μl) and then stirred under an argon atmosphere at room temperature for 19 hours. Saturated aqueous ammonium chloride was added to the reaction system and the organic substances were extracted with ethyl acetate, and then the organic layer was concentrated under reduced pressure. The residue was purified by thin-layer chromatography (chloroform:acetone= 5:1) to obtain benzyl (S)-6-benzyloxycarbonylamino-2-((2-methyl-1-phenylacetylaminopropyl)(benzyloxyphosphinoyl)oxy)hexanoate (60.4 mg, 56%). This compound was subjected to the measurement of molecular weight and then used in the following reaction without further purification.

TSPMS(m/z): 715(M$^+$+1).

(b) In the same manner as the method of (b) in Example 42, the title compound: (S)-6-amino-2-((2-methyl-(1R)-phenylacetylaminopropyl)(hydroxyphosphinoyl)oxy) hexanoic acid was obtained by using the benzyl (S)-6-benzyloxycarbonylamino-2-((2-methyl-1-phenylacetylaminopropyl)(benzyloxyphosphinoyl)oxy) hexanoate obtained in the above step (a) as a starting material.

$^1$H-NMR(D$_2$O): δ0.76(3H,d), 0.81(3H,d), 1.20–1.34(2H, m), 1.48–1.59(2H,m), 1.60–1.68(2H,m), 1.98–2.11(1H,m), 2.84(2H,t), 3.50(1H,d), 3.59(1H,d), 3.85(1H,dd), 4.45–4.51 (1H,m), 7.21–7.33(5H,m).

$^{31}$P-NMR(D$_2$O): δ19.43(1P,s).

FABMS(m/z): 401(M$^+$+1).

Example 44

(S)-6-Amino-2-((1-((2R)-amino-3-phenylpropanoylamino)-2-methylpropyl)(hydroxyphosphinoyl)oxy)hexanoic acid N-Benzyloxycarbonyl-D-phenylalanine was used instead of N-benzyloxycarbonyl-L-phenylalanine in the step (a) of Example 42 to obtain the title compound: (S)-6-amino-2-((1-((2R)-amino-3-phenylpropanoylamino)-2-methylpropyl)(hydroxyphosphinoyl)oxy)hexanoic acid (a diastereoisomeric mixture of 5:2).

$^1$H-NMR(D$_2$O): δ0.43–0.51(4H,m), 0.73–0.84(2H,m), 1.23–1.43(2H,m), 1.47–1.6(2H,m), 1.60–1.74(2H,m), 1.80–2.05(1H,m), 2.79–2.91(2H,m), 2.91–3.14(2H,m), 3.67–3.76(2/7H,m), 3.79–3.89(2/7H,m), 3.98–4.14(1H,m), 4.32–4.44(1H,m), 7.16–7.33(5H,m).

$^{31}$P-NMR(D$_2$O): δ17.90(2/7P,s), 19.37(5/7P,s).

TSPMS(m/z): 430(M$^+$+1).

Example 45

(S)-6-Amino-2-((1-(3-cyclopentylpropanoylamino)-2-methylpropyl)(hydroxyphosphinoyl)oxy)hexanoic acid In the same manner as the method of Example 43, the title compound: (S)-6-amino-2-((1-(3-cyclopentylpropanoylamino)-2-methylpropyl)(hydroxyphosphinoyl)oxy)hexanoic acid (a diastereoisomeric mixture of 2:5) was obtained by using 3-cyclopentylpropionyl chloride instead of phenylacetyl chloride in (a) of Example 43.

$^1$H-NMR(D$_2$O): δ0.78–0.88(6H,m), 1.21–1.74(17H,m), 1.94–2.13(1H,m), 2.14–2.32(2H,m), 2.91(2H,t), 3.79–3.90 (1H,m), 4.36–4.46(1H,m).

$^{31}$P-NMR(D$_2$O): δ18.76(5/7P,s), 19.67(2/7P,s).

TSPMS(m/z): 407(M$^+$+1).

Example 46

(S)-6-Amino-2-((1-(2,4-difluorobenzoylamino)-2-methylpropyl)(hydroxyphosphinoyl)oxy)hexanoic acid (a) 2,4-Difluorobenzoic acid (153.5 mg) and the crude benzyl (S)-2-((1-amino-2-methylpropyl)(benzyloxyphosphinoyl)oxy)-6-benzyloxycarbonylaminohexanoate (144.8 mg) obtained in (e) of Example 24 were dissolved in dimethylformamide (3 ml), and the reaction system was cooled to 0° C. The reaction mixture was added with diisopropylethylamine (250 μl) and benzotriazol-1-yloxy-tris(dimethylamino) phosphonium hexafluorophosphate (429.3 mg) and then stirred under an argon atmosphere at room temperature for 2 hours. Saturated aqueous ammonium chloride was added to the reaction system, and then the organic substances were extracted with ethyl acetate. The organic layer was concentrated under reduced pressure, and the residue was roughly purified by thin-layer chromatography (chloroform:acetone=5:1) to obtain benzyl (S)-6-benzyloxycarbonylamino-2-((1-(2,4-difluorobenzoylamino)-2-methylpropyl)(benzyloxyphosphinoyl)oxy)hexanoate (77.8 mg, 43.5%). This compound was subjected to the measurement of molecular weight and then used in the following reaction without further purification.

TSPMS(m/z): 737($M^+$+1).

(b) In the same manner as the method of (b) in Example 42, the title compound: (S)-6-amino-2-((1-(2,4-difluorobenzoylamino)-2-methylpropyl)(hydroxyphosphinoyl)oxy)hexanoic acid (a diastereoisomeric mixture of 1:2) was obtained by using the benzyl (S)-6-benzyloxycarbonylamino-2-((1-(2,4-difluorobenzoylamino)-2-methylpropyl)(benzyloxyphosphinoyl)oxy)hexanoate obtained in (a) above as a starting material.

$^1$H-NMR($D_2O$): δ0.87(2H,d), 0.92(4H,d), 1.20–1.43(2H, m), 1.49–1.59(2H,m), 1.62–1.71(2H,m), 2.05–2.23(1H,m), 2.85(2H,t), 4.07(2/3H,dd), 4.11(1/3H,dd), 4.38–4.46(1H,m), 6.95–7.02(3H,m), 7.60–7.69(1H,m).

$^{31}$P-NMR($D_2O$): δ18.03(2/3P,s), 18.70(1/3P,s).

TSPMS(m/z): 423($M^+$+1).

Example 47

(S)-6-Amino-2-((1-benzoylamino-2-methylpropyl)(hydroxyphosphinoyl)oxy)hexanoic acid In the same manner as the method of Example 46, the title compound: (S)-6-amino-2-((1-benzoylamino-2-methylpropyl)(hydroxyphosphinoyl)oxy)hexanoic acid (a diastereoisomeric mixture of 1:8) was obtained by using benzoic acid instead of 2,4-difluorobenzoic acid used in the step (a) of Example 46.

$^1$H-NMR($D_2O$): δ0.87(3H,d), 0.94(3H,d), 1.20–1.41(2H, m), 1.43–1.57(2H,m), 1.62–1.71(2H,m), 2.03–2.25(1H,m), 2.78(2H,t), 4.06(8/9H,d), 4.13(1/9H,d), 4.40–4.47(1H,m), 7.45(2H,t), 7.53(1H,t), 7.75(1H,d).

$^{31}$P-NMR($D_2O$): δ18.42(8/9P,s), 19.32(1/9P,s).

FABMS(m/z): 387($M^+$+1).

Example 48

(S)-6-Amino-2-((1-(3-(2-methoxyphenyl)propanoylamino)-2-methylpropyl)(hydroxyphosphinoyl)oxy)hexanoic acid In the same manner as the method of Example 42, the title compound: (S)-6-amino-2-((1-(3-(2-methoxyphenyl)propanoylamino)-2-methylpropyl)(hydroxyphosphinoyl)oxy)hexanoic acid (a diastereoisomeric mixture of 1:3) was obtained by using 3-(2-methoxyphenyl)propanoic acid instead of N-benzyloxycarbonyl-L-phenylalanine used in the step (a) of Example 42.

$^1$H-NMR($D_2O$): δ0.53–0.64(6H,m), 1.21–1.42(2H,m), 1.50–1.61(2H,m), 1.61–1.69(2H,m), 1.81–1.97(1H,m), 2.40–2.50(1H,m), 2.57–2.64(1H,m), 2.75–2.85(2H,m), 2.88(2H,t), 3.74(3H,s), 3.71–3.79(1H,m), 4.35–4.42(1H,m), 6.85(1H,t), 6.92(1H,d), 7.11(1H,dd), 7.16(1H,t).

$^{31}$P-NMR($D_2O$): δ18.88(3/4P,s), 19.70(1/4P,s).

TSPMS(m/z): 387($M^+$+1).

Example 49

(S)-6-Amino-2-((1-(4-methoxyphenyl)acetylamino-2-methylpropyl)(hydroxyphosphinoyl)oxy)hexanoic acid In the same manner as the method of Example 42, the title compound: (S)-6-amino-2-((1-(4-methoxyphenyl)acetylamino-2-methylpropyl)(hydroxyphosphinoyl)oxy)hexanoic acid (a diastereoisomeric mixture of 4:1) was obtained by using 4-methoxyphenylacetic acid instead of N-benzyloxycarbonyl-L-phenylalanine used in the step (a) of Example 42.

$^1$H-NMR($D_2O$): δ0.73(3H,d), 0.82(3H,d), 1.22–1.42(2H, m), 1.50–1.62(2H,m), 1.62–1.71(2H,m), 1.95–2.10(1H,m), 2.90(2H,t), 3.42(1H,d), 3.54(1H,d), 3.73(3H,s), 3.80–3.86 (1H,m), 4.36–4.47(1H,m), 6.89(2H,d), 7.22(2H,d).

$^{31}$P-NMR($D_2O$): δ18.51(1/5P,s), 19.47(4/5P,s).

TSPMS(m/z): 431($M^+$+1).

Example 50

(S)-6-Amino-2-((1-heptanoylamino-2-methylpropyl)(hydroxyphosphinoyl)oxy)hexanoic acid In the same manner as the method of Example 43, the title compound: (S)-6-amino-2-((1-heptanoylamino-2-methylpropyl)(hydroxyphosphinoyl)oxy)hexanoic acid (a diastereoisomeric mixture of 4:5) was obtained by using n-heptanoyl chloride instead of phenylacetyl chloride used in the step (a) of Example 43.

$^1$H-NMR($D_2O$): δ0.73(3H,t), 0.80(6H,dt), 1.10–1.40(8H, m), 1.40–1.70(6H,m), 1.90–2.11(1H,m), 2.12–2.27(2H,m), 2.88(2H,t), 3.76–3.86(1H,m), 4.33–4.44(1H,m).

$^{31}$P-NMR($D_2O$): δ18.86(5/9H,s), 19.71(4/9H,s).

TSPMS(m/z): 395($M^+$+1).

Example 51

(S)-6-Amino-2-((1-(2-amino-2-phenylacetylamino)-2-methylpropyl)(hydroxyphosphinoyl)oxy)hexanoic acid In the same manner as the method of Example 42, the title compound: (S)-6-amino-2-((1-(2-amino-2-phenylacetylamino)-2-methylpropyl)(hydroxyphosphinoyl)oxy)hexanoic acid (a diastereoisomeric mixture of 3:4:2:1) was obtained by using N-benzyloxycarbonyl-L-phenylglycine instead of N-benzyloxycarbonyl-L-phenylalanine used in the above (a) of Example 42.

$^1$H-NMR($D_2O$): δ0.46–0.87(6H,m), 1.09–1.40(2H,m), 1.40–1.72(4H,m), 1.82–2.13(1H,m), 2.76–2.91(2H,m), 3.75–3.90(1H,m), 4.05(0.2H,dq), 4.27(0.3H,dq), 4.40(0.5H, dq), 4.69–4.90(1H,m), 7.28–7.41(5H,m).

$^{31}$P-NMR($D_2O$): δ20.51(3/10P,s), 20.67(4/10P,s), 21.03 (2/10P,s), 21.83(1/10P,s).

TSPMS(m/z): 416($M^+$+1).

Example 52

(S)-6-Amino-2-((2-methyl-1-((pyridin-2-yl)acetylamino)propyl)(hydroxyphosphinoyl)oxy)hexanoic acid In the same manner as the method of Example 42, the title compound: (S)-6-amino-2-((2-methyl-1-((pyridin-2-yl)acetylamino)propyl)(hydroxyphosphinoyl)oxy)hexanoic acid (a diastereoisomeric mixture of 1:5) was obtained by using 2-pyridyl acetate hydrochloride instead of N-benzyloxycarbonyl-L-phenylalanine used in the step (a) of Example 42.

$^1$H-NMR($D_2O$): δ0.77(3H,d), 0.78(3H,d), 1.20–1.42(2H, m), 1.46–1.59(2H,m), 1.60–1.71(2H,m), 1.93–2.11(1H,m), 2.86(2H,t), 3.70–3.79(2H,m), 3.80–3.90(1H,m), 4.36–4.46 (1H,m), 7.29(1H,dd), 7.37(1H,d), 7.78(1H,t), 8.38(1H,d).

$^{31}$P-NMR(D$_2$O): δ18.43(5/6P,s), 19.10(1/6P,s).

TSPMS(m/z): 402(M$^+$+1).

Example 53

(S)-6-Amino-2-((1-(4-methoxybenzoylamino)-2-methylpropyl)(hydroxyphosphinoyl)oxy)hexanoic acid

In the same manner as the method of Example 46, the title compound: (S)-6-amino-2-((1-(4-methoxybenzoylamino)-2-methylpropyl)(hydroxyphosphinoyl)oxy)hexanoic acid (a diastereoisomeric mixture of 5:1) was obtained by using 4-methoxybenzoic acid instead of 2,4-difluorobenzoic acid used in the step (a) of Example 46.

$^1$H-NMR(D$_2$O): δ0.79–0.90(6H,m), 1.10–1.31(2H,m), 1.36–1.49(2H,m), 1.54–1.64(2H,m), 2.06–2.19(1H,m), 2.71(2H,t), 3.74(3H,s), 3.99(1/6H,dd), 4.05(5/6H,dd), 4.35–4.43(1H,m), 6.95(2H,d), 7.68(2H,d).

$^{31}$P-NMR(D$_2$O): δ18.64(1/6P,s), 19.52(5/6P,s).

TSPMS(m/z): 417(M$^+$+1).

Example 54

(S)-6-Amino-2-(((1R)-(4-methoxybenzoylamino)-2-methylpropyl)(hydroxyphosphinoyl)oxy)hexanoic acid

(a) (1R)-Amino-2-methylpropylphosphinic acid (314.4 mg) was dissolved in a mixed solvent of water:dioxane=1:2 (943 μl) and cooled to 0° C., and then added with 5 N aqueous sodium hydroxide (458.6 μl). Then 5 N aqueous sodium hydroxide (917.2 μl) and 4-methoxybenzoyl chloride (782.2 mg) were simultaneously added dropwise to the reaction system over 10 minutes. The mixture was stirred for 1 hour while being kept at 0° C., and then at room temperature for 3 hours. 5 N Hydrochloric acid was added to the mixture to reduce the pH to 2, and the organic substances were extracted with ethyl acetate. The organic layer was concentrated under reduced pressure, and precipitated crystals were washed with diethyl ether to obtain (1R)-(4-methoxybenzoylamino)-2-methylpropylphosphinic acid (558.6 mg, 89.8%). This compound was subjected to the measurement of molecular weight and then used in the following reaction without further purification.

FABMS(m/z): 272(M$^+$+1).

(b) In the same manner as the method of Example 2, the title compound: (S)-6-amino-2-(((1R)-(4-methoxybenzoylamino)-2-methylpropyl)(hydroxyphosphinoyl)oxy)hexanoic acid was obtained by using the (1R)-(4-methoxybenzoylamino)-2-methylpropylphosphinic acid obtained in the above step (a) instead of 2-methyl-1-(3-phenylpropanoylamino)propylphosphinic acid used in the step (b) of Example 2.

$^1$H-NMR(D$_2$O): δ0.89(3H,d), 0.91(3H,d), 1.12–1.34(2H,m), 1.38–1.48(2H,m), 1.56–1.64(2H,m), 2.10–2.21(1H,m), 2.73(2H,t), 3.77(3H,s), 4.07,4.11(1H,d), 4.38–4.44(1H,m), 6.97(2H.,d), 7.72(2H,d).

$^{31}$P-NMR(D$_2$O): δ19.49(1P,s).

TSPMS(m/z): 417(M$^+$+1).

Example 55

(S)-6-Amino-2-((1-dodecanoylamino-2-methylpropyl)(hydroxyphosphinoyl)oxy)hexanoic acid

In the same manner as the method of Example 43, the title compound: (S)-6-amino-2-((1-dodecanoylamino-2-methylpropyl)(hydroxyphosphinoyl)oxy)hexanoic acid (a diastereoisomeric mixture of 1:1) was obtained by using n-dodecanoyl chloride instead of phenylacetyl chloride used in the step (a) of Example 43.

$^1$H-NMR(D$_2$O): δ0.73(3H,t), 0.78–0.89(6H,m), 1.10–1.40(18H,m), 1.41–1.69(6H,m), 2.00–2.32(3H,m), 2.87(2H,m), 3.78–3.93(1H,m), 4.30–4.47(1H,m).

$^{31}$P-NMR(D$_2$O): δ18.97(1/2P,s), 19.80(1/2P,s).

TSPMS(m/z): 465(M$^+$+1).

Example 56

(S)-2-((1-Acetylamino-2-methylpropyl)(hydroxyphosphinoyl)oxy)-6-aminohexanoic acid

In the same manner as the method of Example 43, the title compound: (S)-2-((1-acetylamino-2-methylpropyl)(hydroxyphosphinoyl)oxy)-6-aminohexanoic acid (a diastereoisomeric mixture of 1:3) was obtained by using acetyl chloride instead of phenylacetyl chloride in (a) of Example 43.

$^1$H-NMR(D$_2$O): δ0.78(3H,d), 0.82(3H,d), 1.24–1.46(2H,m), 1.52–1.62(2H,m), 1.63–1.73(2H,m), 1.95(3H,s), 1.95–2.07(1H,m), 2.91(2H,t), 3.75–3.86(1H,m), 4.36–4.46(1H,m).

$^{31}$P-NMR(D$_2$O): δ21.19(3/4P,s), 22.30(1/4P,s).

TSPMS(m/z): 325(M$^+$+1).

Example 57

(S)-6-Amino-2-((1-(3-(4-aminophenyl)propanoylamino)-2-methylpropyl)(hydroxyphosphinoyl)oxy)hexanoic acid

(a) 4-Nitrobenzaldehyde (1 g) was dissolved in methylene chloride (20 ml), and the reaction system was cooled to 0° C. The solution was added with carboethoxymethylenetriphenylphospholan (2.56 g) and stirred at 0° C. for 1 hour. The reaction system was concentrated under reduced pressure without any treatment, and the residue was purified by silica gel column chromatography (50 g, hexane:ethyl acetate=4:1) to obtain ethyl 3-(4-nitrophenyl)acrylate (1.27 g, 86%).

$^1$H-NMR(CDCl$_3$): δ1.36(3H,t), 4.30(2H,q), 6.56(1H,d), 7.67(1H,d), 7.71(1H,d), 8.25(1H,d).

EIMS(m/z): 221(M$^+$).

(b) The ethyl 3-(4-nitrophenyl)acrylate (512.8 mg) obtained in the above step (a) was dissolved in dioxane (5.1 ml), and the solution was added with 5 N sodium hydroxide (2.78 ml) and stirred at room temperature for 3.5 hours. Separation and extraction with diethyl ether was made to remove impurities, and then 5 N hydrochloric acid was added to the aqueous layer to reduce the pH to 2. The precipitated crystals were collected by filtration to obtain 3-(4-nitrophenyl)acrylic acid (270.1 mg, 60.3%).

$^1$H-NMR(DMSO): δ6.75(1H,d), 7.70(1H,d), 7.98(1H,d), 8.24(1H,d), 12.7(1H,brs).

EIMS(m/z): 193(M$^+$).

(c) The 3-(4-nitrophenyl)acrylic acid (99.7 mg) obtained in (b) above and the crude benzyl (S)-2-((1-amino-2-methylpropyl)(benzyloxyphosphinoyl)oxy)-6-benzyloxycarbonylaminohexanoate (154.0 mg) obtained in the step (e) of Example 24 were dissolved in a mixed solvent of dimethylformamide:dimethylsulfoxide=10:1 (2.75 ml). In the same manner as the method of (a) in Example 42, benzyl (S)-6-benzyloxycarbonylamino-2-((2-methyl-1-(3-

(4-nitrophenyl)acryloylamino)propyl)(benzyloxyphosphinoyl)oxy)hexanoate (53 mg, 26.6%) was obtained.

TSPMS(m/z): 772(M$^+$+1).

(d) In the same manner as the method of (b) in Example 42, the title compound: (S)-6-amino-2-((1-(3-(4-aminophenyl)propanoylamino)-2-methylpropyl)(hydroxyphosphinoyl)oxy)hexanoic acid (a diastereoisomeric mixture of 1:5) was obtained by using the benzyl (S)-6-benzyloxycarbonylamino-2-((2-methyl-1-(3-(4-nitrophenyl)acryloylamino)propyl)(benzyloxyphosphinoyl)oxy)hexanoate obtained in the above step (c) as a starting material.

$^1$H-NMR(D$_2$O): δ0.52–0.65(6H,m), 1.22–1.45(2H,m), 1.52–1.62(2H,m), 1.64–1.72(2H,m), 1.81–1.98(1H,m), 2.45–2.59(2H,m), 2.68–2.84(2H,m), 2.90(2H,t), 3.72–3.81(1H,m), 4.35–4.43(1H,m), 6.72(2H,d), 7.03(2H,d).

$^{31}$P-NMR(D$_2$O): δ18.69(5/6P,s), 19.72(1/6P,s).

TSPMS(m/z): 430(M$^+$+1).

Example 58

(S)-6-Amino-2-((1-(3-(3-aminophenyl)propanoylamino)-2-methylpropyl)(hydroxyphosphinoyl)oxy)hexanoic acid In the same manner as the method of Example 57, the title compound: (S)-6-amino-2-((1-(3-(3-aminophenyl)propanoylamino)-2-methylpropyl)(hydroxyphosphinoyl)oxy)hexanoic acid (a diastereoisomeric mixture of 1:4) was obtained by using 3-nitrobenzaldehyde as the starting material.

$^1$H-NMR(D$_2$O): δ0.56–0.67(6H,m), 1.21–1.46(1H,m), 1.50–1.64(2H,m), 1.64–1.73(2H,m), 1.80–2.30(1H,m), 2.45–2.62(2H,m), 2.70–2.84(2H,m), 2.87–2.93(2H,m), 3.73–3.90(1H,m), 4.36–4.45(1H,m), 6.59–6.71(3H,m), 7.08(1H,t).

$^{31}$P-NMR(D$_2$O): δ18.65(4/5P,s), 19.72(1/5P,s).

TSPMS(m/z): 430(M$^+$+1).

Example 59

(S)-6-Amino-2-((2-methyl-1-(trifluoroacetylamino)propyl)(hydroxyphosphinoyl)oxy)hexanoic acid In the same manner as the method of Example 43, the title compound: (S)-6-amino-2-((2-methyl-1-(trifluoroacetylamino)propyl)(hydroxyphosphinoyl)oxy)hexanoic acid (a diastereoisomeric mixture of 1:6) was obtained by using trifluoroacetic anhydride instead of phenylacetyl chloride used in the step (a) of Example 43.

$^1$H-NMR(D$_2$O): δ0.85(3H,d), 0.88(3H,d), 1.26–1.44(2H,m), 1.50–1.64(2H,m), 1.64–1.76(2H,m), 2.03–2.15(1H,m), 2.88(2H,t), 3.87(1/7H,dd), 3.89(6/7H,dd), 4.50–4.60(1H,m).

$^{31}$P-NMR(D$_2$O): δ17.04(6/7P,s), 17.33(1/7P,s).

TSPMS(m/z): 379(M$^+$+1).

Example 60

(S)-6-Amino-2-((2-methyl-1-(3-phenyl-(2S)-(3-phenylpropanoylamino)propanoylamino)propyl)(hydroxyphosphinoyl)oxy)hexanoic acid (a) L-phenylalanine (2 g) was dissolved in a mixed solvent of dioxane:water=1:1 (20 ml), and the reaction system was cooled to 0° C. The solution was added with 1 N aqueous sodium hydroxide (12.1 ml), and further added dropwise with 1 N aqueous sodium hydroxide (12.1 ml) and hydrocinnamoyl chloride (1.98 ml) simultaneously over 25 minutes, and then stirred at 0° C. for 2 hours. 1 N Hydrochloric acid was added to the mixture to adjust the pH to 3, and the precipitated crystals were washed with water and diethyl ether to obtain 3-phenyl-(2S)-(3-phenylpropanoylamino)propanoic acid (2.9 g, 79.9%).

$^1$H-NMR(DMSO-d$_6$): δ2.36(2H,t), 2.72(2H,t), 2.84(1H,dd), 3.04(1H,dd), 4.43(1H,ddd), 7.12–7.29(10H,m), 8.18(1H,d), 12.66(1H,brs).

TSPMS(m/z): 298(M$^+$+1).

(b) In the same manner as the method of Example 46, the title compound: (S)-6-amino-2-((2-methyl-1-(3-phenyl-(2S)-(3-phenylpropanoylamino)propanoylamino)propyl)(hydroxyphosphinoyl)oxy)hexanoic acid (a diastereoisomeric isomer of 3:4) was obtained by using the 3-phenyl-(2S)-(3-phenylpropanoylamino)propanoic acid obtained in the above step (a) instead of 2,4-difluorobenzoic acid used in the step (a) of Example 46.

$^1$H-NMR(D$_2$O): δ0.65–0.84(6H,m), 1.21–1.41(2H,m), 1.49–1.61(2H,m), 1.61–1.71(2H,m), 1.93–2.13(1H,m), 2.33–2.47(2H,m), 2.58–2.66(2H,m), 2.67–2.77(1H,m), 2.82–2.90(2H,m), 2.98–3.14(1H,m), 3.78–3.89(1H,m), 4.35–4.42(1H,m), 4.42–4.55(1H,m), 6.91–6.98(2H,m), 7.08–7.27(8H,m).

$^{31}$P-NMR(D$_2$O): δ18.25(4/7P,s), 18.96(3/7P,s).

TSPMS(m/z): 562(M$^+$+1).

Example 61

(S)-6-Amino-2-((2-methyl-1-(5-oxohexanoylamino)propyl)(hydroxyphosphinoyl)oxy)hexanoic acid (a) 4-Oxohexanoic acid (56.2 μl) was dissolved in methylene chloride (1.4 ml), and the solution was added with triethylamine (98.5 μl) and pivalic chloride (58.0 μl) and stirred under an argon atmosphere at room temperature for 15 minutes. The resulting mixture was added to a methylene chloride (1.4 ml) solution of the crude benzyl (S)-2-((1-amino-2-methylpropyl)(benzyloxyphosphinoyl)oxy)-6-benzyloxycarbonylaminohexanate (140.5 mg) obtained in the step (e) of Example 24, and the mixture was further stirred at room temperature for 4 hours. Saturated aqueous ammonium chloride was added to the mixture, and then the organic substances were extracted with ethyl acetate and the organic layer was concentrated under reduced pressure. The residue was purified by silica gel column chromatography (15 g, hexane:acetone=3:1) to obtain benzyl (S)-6-benzyloxycarbonylamino-2-((2-methyl-1-(5-oxohexanoylamino)propyl)(benzyloxyphosphinoyl)oxy)hexanoate (105.4 mg, 63.1%). This compound was subjected to the measurement of molecular weight and then used in the following reaction without further purification.

TSPMS(m/z): 709(M$^+$+1).

(b) In the same manner as the method of (b) in Example 42, the title compound: (S)-6-amino-2-((2-methyl-1-(5-oxohexanoylamino)propyl)(hydroxyphosphinoyl)oxy)hexanoic acid (a diastereoisomeric mixture of 1:1) was obtained by using the benzyl (S)-6-benzyloxycarbonylamino-2-((2-methyl-1-(5-oxohexanoylamino)propyl)(benzyloxyphosphinoyl)oxy)hexanoate obtained in the above step (a) as a starting material.

$^1$H-NMR(D$_2$O): δ0.76–0.86(6H,m), 1.23–1.50(2H,m), 1.51–1.77(4H,m), 1.72(2H,q), 1.90–2.10(1H,m), 2.09(3H, s), 2.13–2.24(2H,m), 2.49(1H,t), 2.50(1H,t), 2.89(1H,t), 2.90(1H,t), 3.78–3.87(1H,m), 4.35–4.45(1H,m).

$^{31}$P-NMR(D$_2$O): δ18.56(1/2P,s), 19.63(1/2P,s).

TSPMS(m/z): 395(M$^+$+1).

Example 62

(S)-6-Amino-2-((1-((3R)-hydroxybutanoylamino)-2-methylpropyl)(hydroxyphosphinoyl)oxy)hexanoic acid In the same manner as the method of Example 42, the title compound: (S)-6-amino-2-((1-((3R)-hydroxybutanoylamino)-2-methylpropyl)(hydroxyphosphinoyl)oxy)hexanoic acid (a diastereoisomeric mixture of 1:1) was obtained by using (3R)-benzyloxybutanoic acid, prepared by the method described in Helv. Chem. Acta., 155(1988), instead of N-benzyloxycarbonyl-L-phenylalanine in (a) of Example 42.

$^1$H-NMR(D$_2$O): δ0.77–0.87(6H,d), 1.12(3H,d), 1.25–1.45(2H,m), 1.50–1.62(2H,m), 1.62–1.72(2H,m), 1.95–2.10(1H,m), 2.26–2.40(2H,m), 2.90(2H,t), 3.85(1H,dd), 4.00–4.15(1H,m), 4.36–4.45(1H,m).

$^{31}$P-NMR(D$_2$O): δ18.59(1/2P,s), 19.59(1/2P,s).

TSPMS(m/z): 369(M$^+$+1).

Example 63

(S)-6-Amino-2-((1-(3-methoxypropanoylamino)-2-methylpropyl)(hydroxyphosphinoyl)oxy)hexanoic acid (a) 3-Methoxypropanoic acid (1.1 g) was dissolved in methylene chloride (11 ml), and the solution was added with thionyl chloride (2.51 g) and then warmed to 40° C. and stirred for 2 hours. The reaction system was concentrated under reduced pressure without any treatment to obtain crude 3-methoxypropionyl chloride. This compound was used in the following reaction without further purification.

(b) In the same manner as the method of Example 43, the title compound: (S)-6-amino-2-((1-(3-methoxypropanoylamino)-2-methylpropyl)(hydroxyphosphinoyl)oxy)hexanoic acid (a diastereoisomeric mixture of 1:1) was obtained by using the 3-methoxypropionyl chloride obtained in the above step (a) instead of phenylacetyl chloride in (a) of Example 43.

$^1$H-NMR(D$_2$O): δ0.75–0.86(6H,m), 1.25–1.45(2H,m), 1.51–1.62(2H,m), 1.62–1.72(2H,m), 1.92–2.11(1H,m), 2.36–2.52(2H,m), 2.89(2H,t), 3.238(3/2H,s), 3.242(3/2H,s), 3.56–3.67(2H,m), 3.83(1/2H,t), 3.87(1/2H,t), 4.35–4.45(1H,m).

$^{31}$P-NMR(D$_2$O): δ18.57(1/2P,s), 19.61(1/2P,s).

TSPMS(m/z): 369(M$^+$+1).

Example 64

(S)-6-Amino-2-((2-methyl-1-(3,4,5-trimethoxybenzoylamino)propyl)(hydroxyphosphinoyl)oxy)hexanoic acid In the same manner as the method of Example 43, the title compound: (S)-6-amino-2-((2-methyl-1-(3,4,5-trimethoxybenzoylamino)propyl)(hydroxyphosphinoyl)oxy)hexanoic acid (a diastereoisomeric mixture of 1:1) was obtained by using 3,4,5-trimethoxybenzoyl chloride instead of phenylacetyl chloride used in the step (a) of Example 43.

$^1$H-NMR(D$_2$O): δ0.85–0.93(6H,m), 1.17–1.36(2H,m), 1.39–1.54(2H,m), 1.60–1.72(2H,m), 2.05–2.17(1H,m), 2.72(1H,t), 2.74(1H,t), 3.70(3H,s), 3.79(6H,s), 4.07(1H,dt), 4.51–4.60(1H,m), 7.05(2H,d).

$^{31}$P-NMR(D$_2$O): δ18.98(1/2P,s), 19.58(1/2P,s).

TSPMS(m/z): 477(M$^+$+1).

Example 65

(S)-6-Amino-2-((1-(3-carboxypropanoylamino)-2-methylpropyl)(hydroxyphosphinoyl)oxy)hexanoic acid In the same manner as the method of Example 61, the title compound: (S)-6-amino-2-((1-(3-carboxypropanoylamino)-2-methylpropyl)(hydroxyphosphinoyl)oxy)hexanoic acid (a diastereoisomeric mixture of 1:1) was obtained by using monobenzyl succinate instead of 4-oxohexanoic acid used in the step (a) of Example 61.

$^1$H-NMR(D$_2$O): δ0.76–0.86(6H,m), 1.20–1.42(2H,m), 1.51–1.61(2H,m), 1.61–1.70(2H,m), 1.93–2.10(1H,m), 2.36(2H,d), 2.39–2.56(2H,m), 2.88(2H,t), 3.77–3.88(1H,m), 4.33–4.45(1H,m).

$^{31}$P-NMR(D$_2$O): δ18.86(112P,s), 19.96(1/2P,s).

TSPMS(m/z): 383(M$^+$+1).

Example 66

(S)-6-Amino-2-((2-methyl-1-(pyridin-2-carbonylamino)propyl)(hydroxyphosphinoyl)oxy)hexanoic acid In the same manner as the method of Example 61, the title compound: (S)-6-amino-2-((2-methyl-1-(pyridin-2-carbonylamino)propyl)(hydroxyphosphinoyl)oxy)hexanoic acid (a diastereoisomeric mixture of 4:5) was obtained by using picolinic acid instead of 4-oxohexanoic acid used in the step (a) of Example 61.

$^1$H-NMR(D$_2$O): δ0.86–0.94(6H,m), 1.10–1.65(6H,m), 2.06–2.25(1H,m), 2.71(8/9H,t), 2.76(10/9H,t), 4.05(1H,dt), 4.34–4.42(1H,brm), 7.51(1H,brm), 7.87–7.95(2H,brm), 8.49–8.51(1H,brs).

$^{31}$P-NMR(D$_2$O): δ18.20(5/9P,s), 18.94(4/9P,s).

TSPMS(m/z): 388(M$^+$+1).

Example 67

(S)-6-Amino-2-((2-methyl-1-(morpholine-4-carbonylamino)propyl)(hydroxyphosphinoyl)oxy)hexanoic acid In the same manner as the method of Example 43, the title compound: (S)-6-amino-2-((2-methyl-1-(morpholine-4-carbonylamino)propyl)(hydroxyphosphinoyl)oxy)hexanoic acid (a diastereoisomeric mixture of 3:4) was obtained by using 4-morpholinecarbonyl chloride instead of phenylacetyl chloride used in the step (a) of Example 43.

$^1$H-NMR(D$_2$O): δ0.73–0.85(6H,m), 1.24–1.46(2H,m), 1.49–1.71(4H,m), 1.84–2.09(1H,m), 2.89(2H,dt), 3.25–3.39(4H,m), 3.59–3.65(4H,m), 3.76(1H,dt), 4.33–4.43(1H,m).

$^{31}$P-NMR(D$_2$O): δ19.85(4/7P,s), 20.76(3/7P,s).

TSPMS(m/z): 396(M$^+$+1).

Example 68

4-((2-Methyl-1-(3-phenylpropionylamino)propyl)(hydroxyphosphinoyl)oxy)piperidine-4-carboxylic acid (a) 4-Cyano-1-ethoxycarbonyl-4-hydroxypiperidine (304 mg) described in Tetrahedron) 7625(1999) was dissolved in 50% sulfuric acid (3 ml) and the solution was refluxed for 19 hours. The reaction mixture was diluted with water, and then roughly purified with Muromac AG50WX8 (Muromachi Kagaku Kogyo Co., 20 cc, elution with aqueous $NH_4$) to obtain crude 4-hydroxypiperidine-4-carboxylic acid. This crude 4-hydroxypiperidine-4-carboxylic acid was subjected to the measurement of molecular weight and then used in the following reaction without further purification.

TSPMS(m/z): 146($M^+$+1).

(b) The crude 4-hydroxypiperidine-4-carboxylic acid obtained in the above step (a) was dissolved in a mixed solvent of 1 N aqueous sodium hydroxide (1.4 ml) and tetrahydrofuran (2 ml), and the solution was added with benzyl chloroformate (0.1 ml). The reaction mixture was stirred at room temperature for 2 hours and 30 minutes, and then acidified with hydrochloric acid and extracted with ethyl acetate. The organic layer was washed with saturated brine and dried over anhydrous magnesium sulfate, and the solvent was evaporated to obtain crude 1-benzyloxycarbonyl-4-hydroxypiperidine-4-carboxylic acid. This crude 1-benzyloxycarbonyl-4-hydroxypiperidine-4-carboxylic acid was subjected to the measurement of molecular weight and then used in the following reaction without further purification.

TSPMS(m/z): 280($M^+$+1).

(c) To a N,N-dimethylformamide solution (3 ml) of the crude 1-benzyloxycarbonyl-4-hydroxypiperidine-4-carboxylic acid obtained in the above step (b), potassium carbonate (121 mg) and benzyl bromide (0.1 ml) were added, and the mixture was stirred at room temperature for 13 hours. The organic substances were extracted with ethyl acetate, and the extract was washed with saturated brine, and then dried over anhydrous magnesium sulfate. The solvent was evaporated, and then the residue was purified by silica gel column chromatography (10 g, hexane:ethyl acetate= 2:1~1:1) to obtain benzyl 1-benzyloxycarbonyl-4-hydroxypiperidine-4-carboxylate (110 mg, 19% (3 steps)).

$^1$H-NMR($CDCl_3$): δ1.5–1.7(2H,m), 1.9–2.1(2H,m), 3.1–3.3(2H,m), 3.9–4.2(2H,m), 5.13(2H,brs), 5.21(2H,s), 7.3–7.4(10H,m).

TSP(m/z): ($M^+$+1). (d) In the same manner as the method of Example 2, the title compound: 4-((2-methyl-1-(3-phenylpropionylamino)propyl)(hydroxyphosphinoyl)oxy)piperidine-4-carboxylic acid was obtained by using the benzyl 1-benzyloxycarbonyl-4-hydroxypiperidine-4-carboxylate obtained in the above step (c) instead of benzyl (S)-6-benzyloxycarbonylamino-2-hydroxyhexanoate used in the step (b) of Example 2.

$^1$H-NMR($D_2O$): δ0.65(3H,d), 0.66(3H,d), 1.9–2.13(3H,m), 2.15–2.3(2H,m), 2.5–2.75(2H,m), 2.8–3.0(2H,m), 3.76 (1H,dd), 7.18(1H,t), 7.23–7.35(4H,m).

TSPMS(m/z): 413($M^+$+1).

Example 69

1-Amidino-4-((2-methyl-1-(3-phenylpropionylamino)propyl)(hydroxyphosphinoyl)oxy)piperidine-4-carboxylic acid (a) The 4-hydroxypiperidine-4-carboxylic acid (279 mg) obtained in the step (a) of Example 68 and triethylamine (0.6 ml) were dissolved in a mixed solvent of tetrahydrofuran (6 ml) and water (6 ml). The resulting solution was added with 1-($N^1$,$N^2$-bisbenzyloxycarbonylamidino)pyrazole (728 mg) described in Tetrahedron Lett., 3389(1993) and stirred at room temperature for 17.5 hours. The reaction mixture was added with saturated aqueous sodium hydrogencarbonate, washed with ethyl acetate, and then acidified with hydrochloric acid. The organic substances were extracted with ethyl acetate. The organic layer was washed with saturated brine and dried over anhydrous magnesium sulfate. The solvent was evaporated to obtain 1-($N^1$,$N^2$-bisbenzyloxycarbonylamidino)-4-hydroxypiperidine-4-carboxylic acid (404 mg, 46%).

$^1$H-NMR($CDCl_3$): δ1.65(2H,d), 2.14(2H,dd), 3.41(2H, dd), 4.00(2H,d), 5.13(4H,s), 7.2–7.4(10H,m), 7.8–8.3(1H, brs).

TSPMS(m/z): 456($M^+$+1).

(b) To a N,N-dimethylformamide (0.5 ml) solution of the 1-($N^1$,$N^2$-bisbenzyloxycarbonylamidino)-4-hydroxypiperidine-4-carboxylic acid (72 mg) obtained in the above step (a), potassium carbonate (27 mg) and benzyl bromide (20 μl) were added. The reaction mixture was stirred at room temperature for 14 hours, and then extracted with ethyl acetate. The extract was washed with saturated brine and dried over anhydrous magnesium sulfate. The solvent was evaporated, and the residue was purified by silica gel column chromatography (15 g, hexane:ethyl acetate=1:1) to obtain benzyl 1-($N^1$,$N^2$-bisbenzyloxycarbonylamidino)-4-hydroxypiperidine-4-carboxylate (64 mg, 74%).

$^1$H-NMR(DMSO-$d_6$): δ1.68(2H,s), 1.88(2H,dd), 3.20 (2H,dd), 3.7–3.9(2H,m), 4.9–5.1(2H,m), 5.15(2H,s), 7.3–7.5(15H,m).

TSPMS(m/z): 546($M^+$+1).

(c) In the same manner as the method of Example 2, the title compound: 1-amidino-4-((2-methyl-1-(3-phenylpropionylamino)propyl)(hydroxyphosphinoyl)oxy) piperidine-4-carboxylic acid was obtained by using the benzyl 1-($N^1$,$N^2$-bisbenzyloxycarbonylamidino)-4-hydroxypiperidine-4-carboxylate obtained in the above step (b) instead of benzyl (S)-6-benzyloxycarbonylamino-2-hydroxyhexanoate in (b) of Example 2.

$^1$H-NMR($CD_3OD$): δ0.85–1.0(6H,m), 1.95–2.3(5H,m), 3.4–3.8(8H,m), 3.9–4.0(1H,m), 7.1–7.3(5H,m).

TSPMS(m/z): 455($M^+$+1).

Example 70

1-(2-Aminoethyl)-4-((2-methyl-1-(3-phenylpropionylamino)propyl)(hydroxyphosphinoyl) oxy)piperidine-4-carboxylic acid (a) The 4-hydroxypiperidine-4-carboxylic acid (118 mg) obtained in the step (a) of Example 68 was dissolved in 1 N hydrochloric acid/ethanol (5 ml) solution, and the resulting solution was stirred at room temperature for 17 hours and then under reflux for 6 hours. The reaction mixture was concentrated to obtain crude ethyl 4-hydroxypiperidine-4-carboxylate. This crude ethyl 4-hydroxypiperidine-4-carboxylate was used in the following reaction without purification.

(b) To a N,N-dimethylformamide (3 ml) solution of the crude ethyl 4-hydroxy-piperidine-4-carboxylate obtained in the above step (a), (2-benzyloxycarbonylamino)ethyl p-toluenesulfonate (311 mg), obtained from aminoethanol in a conventional manner, and potassium carbonate (245 mg) were added, and the mixture was stirred at room temperature for 14 hours and at 50° C. for hours. The organic substances were extracted with ethyl acetate, and the extract was washed with saturated brine. The organic layer was dried over anhydrous magnesium sulfate, and the solvent was evaporated. The residue was purified by silica gel column chromatography and then with LH-20 (Sephadex) to obtain ethyl 1-(2-benzyloxycarbonylaminoethyl)-4-hydroxypiperidine-4-carboxylate (118 mg, 42% (2 steps)).

$^1$H-NMR(CDCl$_3$): δ1.29(3H,t), 1.61(2H,d), 2.05(2H,dd), 2.39(2H,dd), 2.50(2H,t), 2.69(2H,d), 3.31(2H,d), 4.22(2H, q), 5.10(2H,s), 5.44(1H,brs), 7.3–7.4(5H,m).

TSPMS(m/z): 351(M$^+$+1).

(c) The ethyl 1-(2-benzyloxycarbonylaminoethyl)-4-hydroxypiperidine-4-carboxylate (118 mg) obtained in the above step (b) was dissolved in tetrahydrofuran (0.5 ml), and the solution was added with 1 N aqueous sodium hydroxide (0.35 ml) and stirred at room temperature for 4 hours. Then the reaction mixture was purified by using HP-20 (Diaion, 80 cc, methanol:water=1:1) to obtain sodium salt of 1-(2-benzyloxycarbonylaminoethyl)-4-hydroxypiperidine-4-carboxylic acid (91 mg).

$^1$H-NMR(D$_2$O): δ1.52(2H,d), 1.94(2H,dd), 2.38(2H,dd), 2.53(2H,t), 2.78(2H,d), 3.23(2H,d), 5.01(2H,s), 7.2–7.4(5H, m).

TSPMS(m/z): 323(M$^+$+1).

(d) To a N,N-dimethylformamide (2.5 ml) solution of the sodium salt of 1-(2-benzyloxycarbonylaminoethyl)-4-hydroxypiperidine-4-carboxylic acid (91 mg) obtained in the above step (c), sodium carbonate (27 mg) and benzyl bromide (35 μl) were added, and the mixture was stirred at room temperature for 25 hours. The organic substances were extracted with ethyl acetate, and the extract was washed with saturated brine and dried over anhydrous magnesium sulfate. The solvent was evaporated, and the residue was purified by silica gel column chromatography (8 g, methylene chloride:methanol=10:1) and then by using LH-20 (Sephadex, 80 cc, methylene chloride:methanol=1:1) to obtain benzyl 1-(2-benzyloxycarbonylaminoethyl)-4-hydroxypiperidine-4-carboxylate (66 mg, 61%).

$^1$H-NMR(CDCl$_3$): δ1.62(2H,d), 2.07(2H,dd), 2.38(2H, dd), 2.48(2H,t), 2.68(2H,d), 3.29(2H,t), 5.09(2H,s), 5.20 (2H,s), 5.38(1H,brs), 7.2–7.4(10H,m).

TSPMS(m/z): 413(M$^+$+1).

(e) 1-Amino-2-methylpropylphosphonic acid (2.7 g) described in Synthesis 370(1988) was dissolved in water (27 ml), and the solution was added with 5 N aqueous sodium hydroxide (10.5 ml) and 3-phenylpropanoyl chloride (2.6 ml) and stirred at room temperature for 16 hours. The reaction mixture was washed with diethyl ether and acidified with hydrochloric acid. The organic substances were extracted with ethyl acetate, and the extract was washed with saturated brine to obtain 2-methyl-1-(3-phenylpropanoylamino)propylphosphonic acid (554 mg, 11%).

$^1$H-NMR(CDCl$_3$): δ0.82(3H,d), 0.84(3H,d), 2.0–2.2(1H, m), 2.5–2.7(2H,m), 2.9–3.0(2H,m), 4.1–4.2(1H,m), 6.70 (1H,d), 7.1–7.3(5H,m).

TSPMS(m/z): 286(M$^+$+1).

(f) To a methylene chloride (0.4 ml) solution of the benzyl 1-(2-benzyloxycarbonylaminoethyl)-4-hydroxypiperidine-4-carboxylate (109 mg) obtained in the above step (d), the 2-methyl-1-(3-phenylpropanoylamino)propylphosphonic acid (96 mg) obtained in the above step (e) and N-(dimethylaminopropyl)-N'-ethylcarbodiimide hydrochloride (86 mg) were added, and the resulting mixture was stirred at room temperature for 25.5 hours. The reaction mixture was purified by using LH-20 (Sephadex, 300 cc, methylene chloride:methanol=1:1) to obtain benzyl 1-(2-benzyloxycarbonylaminoethyl)-4-((2-methyl-1-(3-phenylpropanoylamino)propyl)(hydroxyphosphinoyl)oxy) piperidine-4-carboxylate (56 mg, 26%).

$^1$H-NMR(CDCl$_3$): δ0.79(6H,d), 2.0–2.5(5H,m), 2.8–3.5 (12H,m), 3.9–4.1(1H,m), 5.05(2H,s), 5.07(2H,s), 7.1–7.3 (15H,m).

TSPMS(m/z): 680(M$^+$+1).

(g) The benzyl 1-(2-benzyloxycarbonylaminoethyl)-4-((2-methyl-1-(3-phenylpropanoylamino)propyl) (hydroxyphosphinoyl)oxy)piperidine-4-carboxylate (56 mg) obtained in the above step (f) was dissolved in a mixed solvent of dioxane (1.5 ml) and water (0.5 ml), and then the solution was added with palladium hydroxide (13 mg). The mixture was stirred under a hydrogen atmosphere at room temperature for 3 hours. The reaction mixture was filtered with celite, and then the solvent was evaporated. The residue was purified with HP-20 (Diaion, 40 cc, methanol:water=1:1 to acetone:water=1:4)) to obtain the title compound:1-(2-aminoethyl)-4-((2-methyl-1-(3-phenylpropionylamino) propyl)(hydroxyphosphinoyl)oxy)piperidine-4-carboxylic acid (32 mg, 84%).

$^1$H-NMR(D$_2$O): δ0.61(6H,d), 1.8–2.15(3H,m), 2.15–2.4 (2H,m), 2.5–2.7(2H,m), 2.75–2.95(2H,m), 3.2–3.5(8H,m), 3.70(1H,dd), 7.1–7.3(5H,m).

$^{31}$P-NMR(D$_2$O): δ18.7(1P,s).

FABMS(m/z): 456(M$^+$+1).

Example 71

(R)-6-Amino-2-((2-methyl-(1R)-(3-phenylpropanoylamino)propyl) (hydroxyphosphinoyl)oxy)hexanoic acid In the same manner as the method of Example 2, the title compound: (R)-6-amino-2-((2-methyl-(1R)-(3-phenylpropanoylamino)propyl)(hydroxyphosphinoyl)oxy) hexanoic acid was obtained by using (1R)-amino-2-methylphosphinic acid instead of amino-2-methylphosphinic acid used in the step (a) of Example 2, and using benzyl (R)-6-benzyloxycarbonylamino-2-hydroxyhexanoate instead of benzyl (S)-6-benzyloxycarbonylamino-2-hydroxyhexanoate used in the above step (b) of Example 2.

$^1$H-NMR(D$_2$O): δ0.60(6H,d), 1.2–1.5(2H,m), 1.5–1.8 (4H,m), 1.8–2.0(1H,m), 2.5–2.7(2H,m), 2.8–3.0(4H,m), 3.79(1H,dd), 4.41(1H,dt), 7.1–7.4(5H,m).

$^{31}$P-NMR(D$_2$O): δ18.6(1P,s).

FABMS(m/Z): 415(M$^+$+1).

Example 72

7-Amino-2-((2-methyl-1-(3-phenylpropanoylamino) propyl)hydroxyphosphinoyl)methylheptanoic acid In the same manner as the method of Example 22, the title compound: 7-amino-2-((2-methyl-1-(3-phenylpropanoylamino)propyl)hydroxyphosphinoyl) methylheptanoic acid (a diastereoisomeric mixture of 1:3) was obtained by using 5-aminopentanol instead of 4-amino-1-butanol used in the step (a) of Example 22.

$^1$H-NMR(D$_2$O): δ0.6–0.7(6H,m), 1.1–1.7(1OH,m), 1.9–2.1(1H,m), 2.4–2.5(1H,m), 2.5–2.7(2H,m), 2.7–2.9(4H, m), 3.6–3.7(1H,m), 7.1–7.3(5H,m).

$^{31}$P-NMR(D$_2$O): δ38.3(1/4P,s), 37.9(3/4P,s).

TSPMS(m/z): 427(M$^+$+1).

Example 73

(S)-6-Amino-2-((2-methyl-1-(3-phenylpropanoylamino)propyl) (hydroxyphosphinoyl)oxy)hexanoic acid In the same manner as the method of Example 70, the title compound: (S)-6-amino-2-((2-methyl-1-(3- phenylpropanoylamino)propyl)(hydroxyphosphinoyl)oxy) hexanoic acid was obtained by using benzyl (S)-6-benzyloxycarbonylamino-2-hydroxyhexanoate instead of benzyl 1-(2-benzyloxycarbonylaminoethyl)-4-hydroxypiperidine-4-carboxylate used in the step (f) of Example 70. The spectrum data of the resulting compound showed similar values to those of the compound obtained in Example 2.

$^1$H-NMR(D$_2$O): δ0.56(1.5H,d), 0.59(3H,m), 0.66(1.5H,d), 1.2–1.5(2H,m), 1.6–1.8(4H,m), 1.8–2.0(1H,m), 2.5–2.7(2H,m), 2.8–3.0(4H,m), 3.7–3.9(1H,m), 4.3–4.5(1H,m), 7.1–7.3(5H,m).

$^{31}$P-NMR(D$_2$O): δ18.7(0.5P,s), 19.7(0.5P,s).

TSPMS(m/z): 415(M$^+$+1).

Chemical structures of the title compounds according to Examples 1 to 73 are as follows:

| Example No. | Chemical structure |
|---|---|
| 1 | |
| 2 | |
| 3 | |
| 4 | 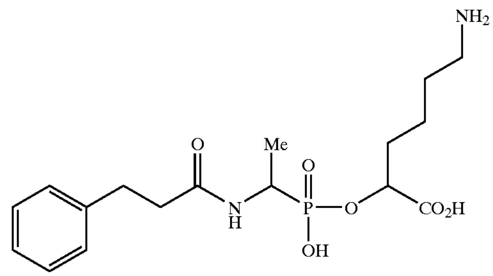 |
| 5 | 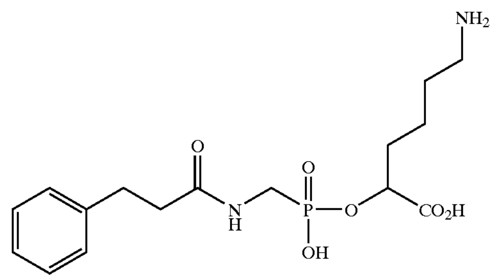 |
| 6 | 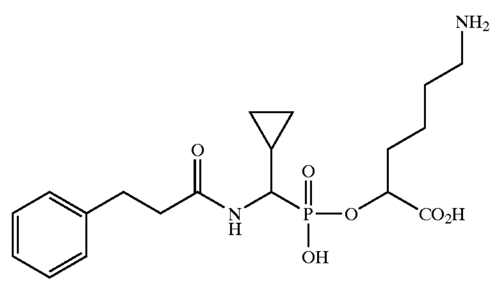 |
| 7 | 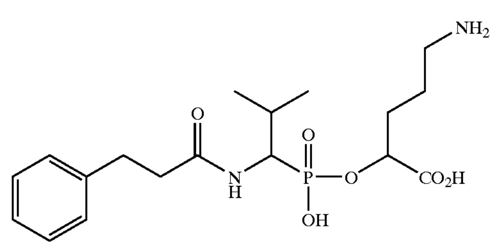 |
| 8 | 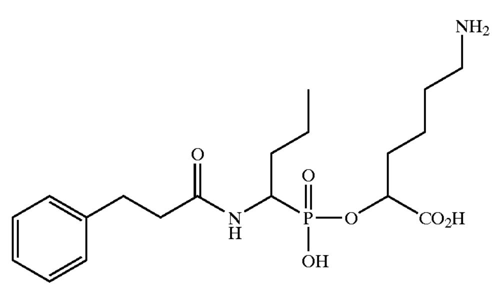 |

-continued
| Example No. | Chemical structure |
|---|---|
| 9 | 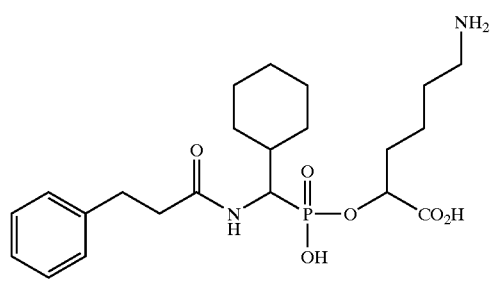 |
| 10 | 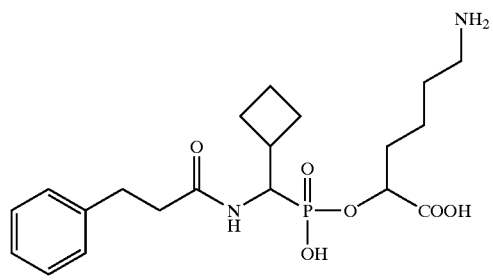 |
| 11 | 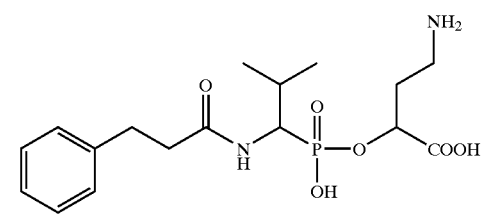 |
| 12 | 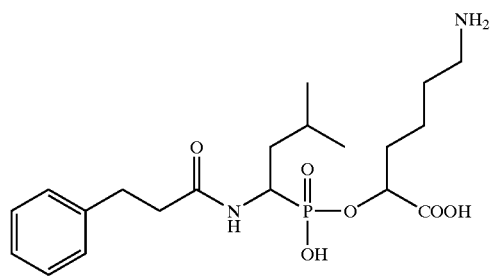 |
| 13 | 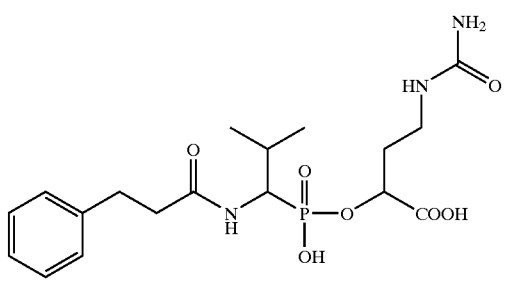 |
-continued
| Example No. | Chemical structure |
|---|---|
| 14 | 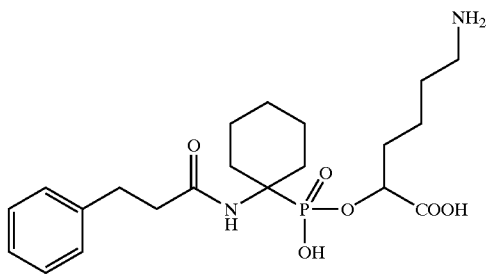 |
| 15 | 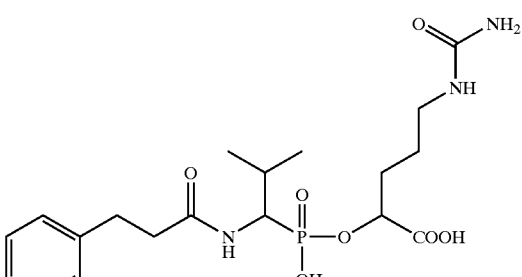 |
| 16 | 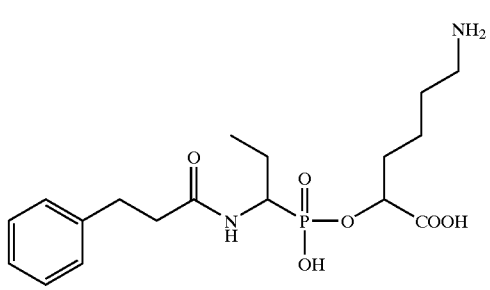 |
| 17 | 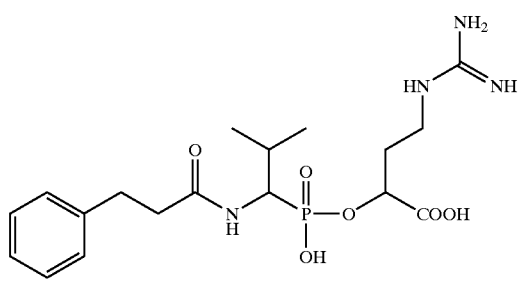 |
| 18 | 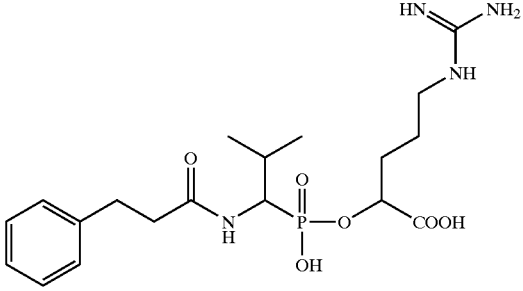 |

-continued
| Example No. | Chemical structure |
|---|---|
| 19 | 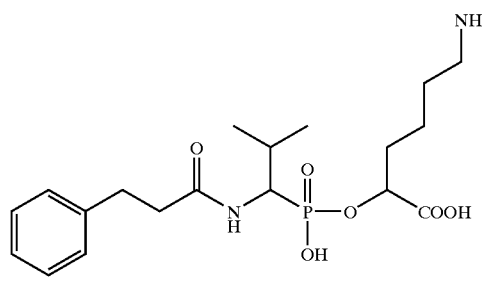 |
| 20 | 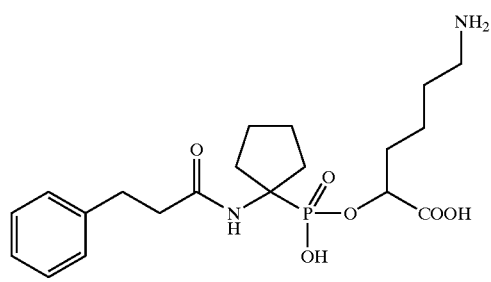 |
| 21 | 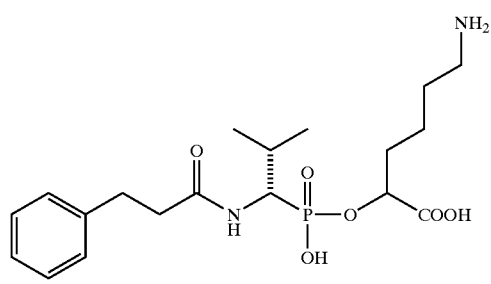 |
| 22 | 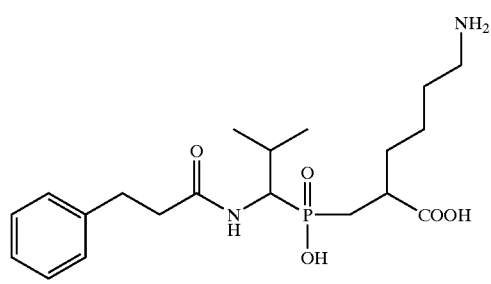 |
| 23 | 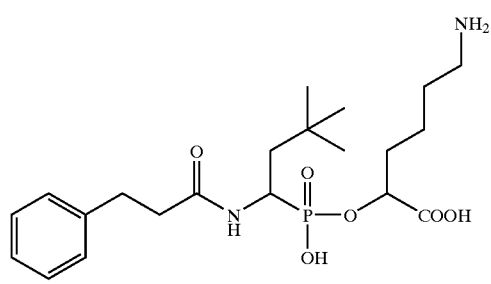 |
-continued
| Example No. | Chemical structure |
|---|---|
| 24 | 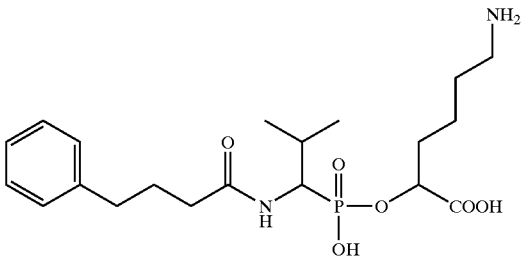 |
| 25 | 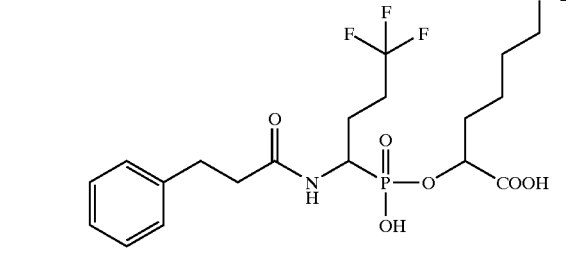 |
| 26 | 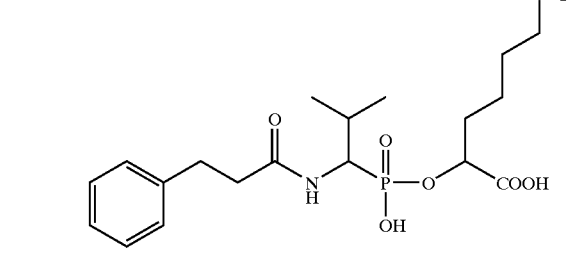 |
| 27 | 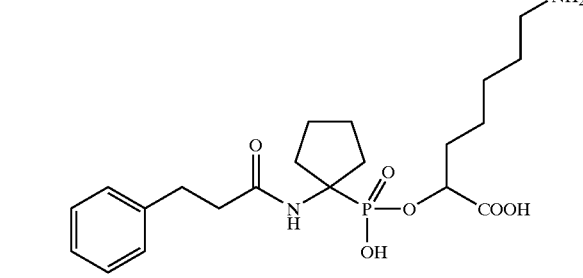 |
| 28 | 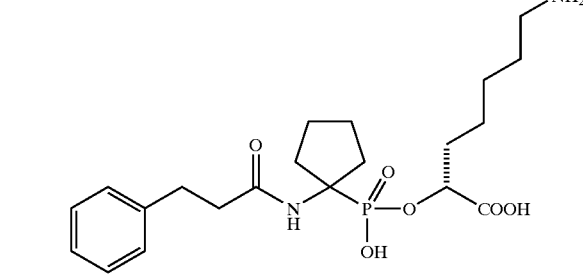 |

| Example No. | Chemical structure |
|---|---|
| 29 | 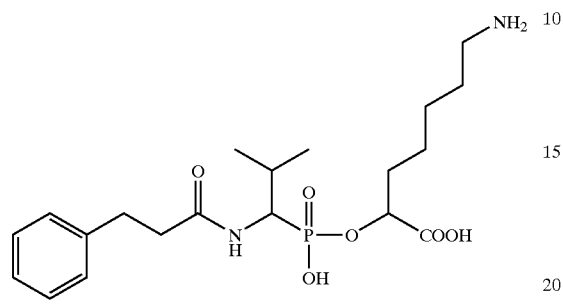 |
| 30 | 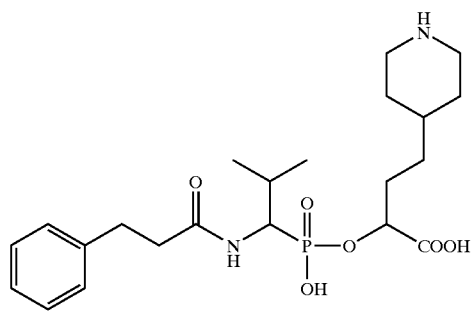 |
| 31 | 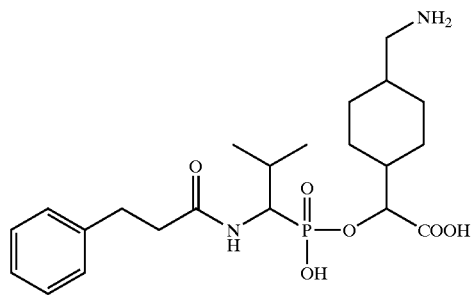 |
| 32 | 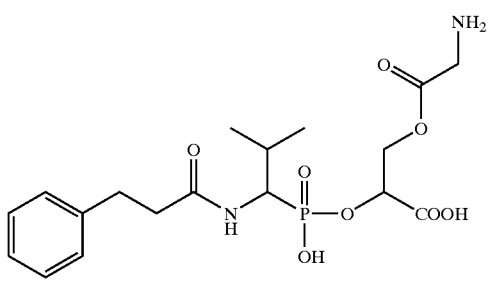 |
| 33 | 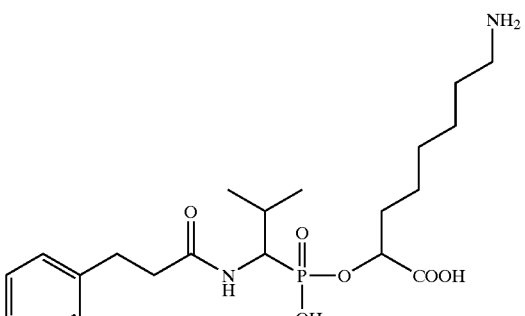 |
| 34 | 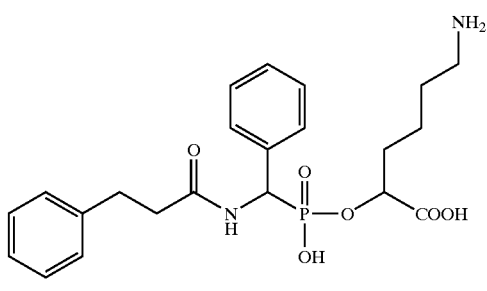 |
| 35 | 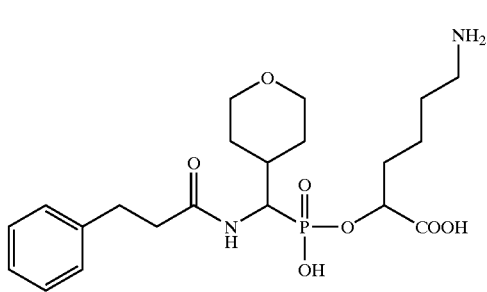 |
| 36 | 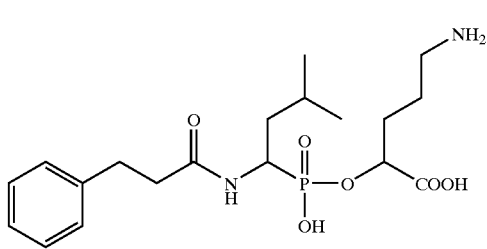 |
| 37 | 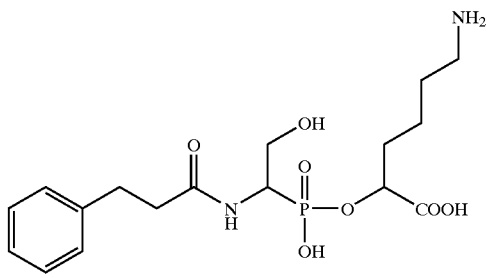 |

-continued
| Example No. | Chemical structure |
|---|---|
| 38 | 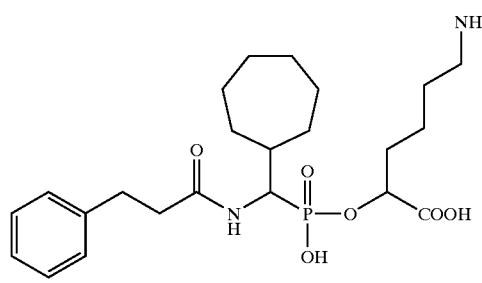 |
| 39 | 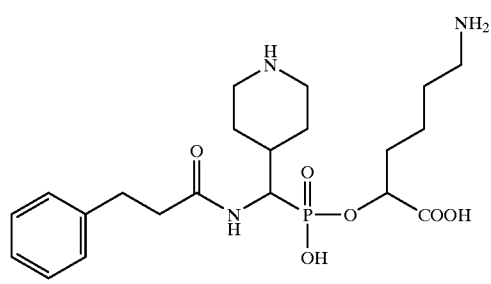 |
| 40 | 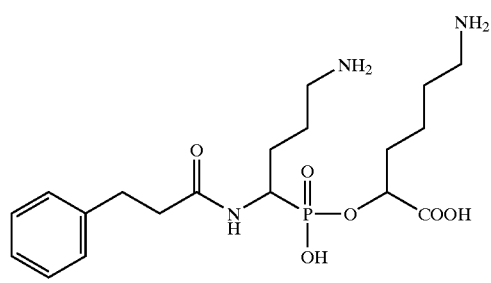 |
| 41 | 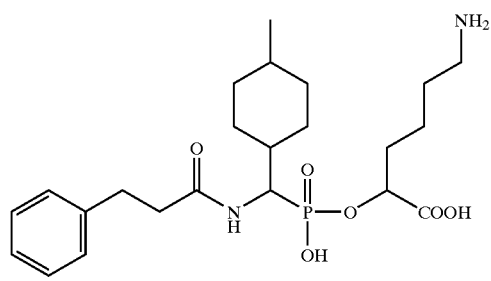 |
| 42 | 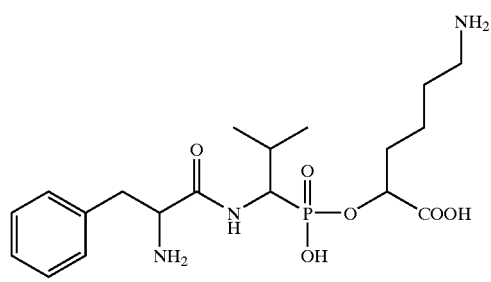 |
-continued
| Example No. | Chemical structure |
|---|---|
| 43 | 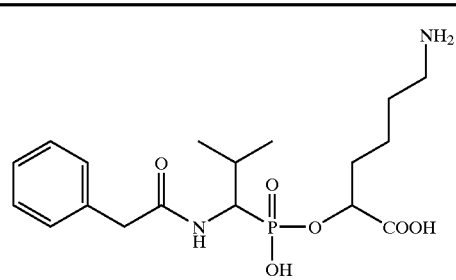 |
| 44 | 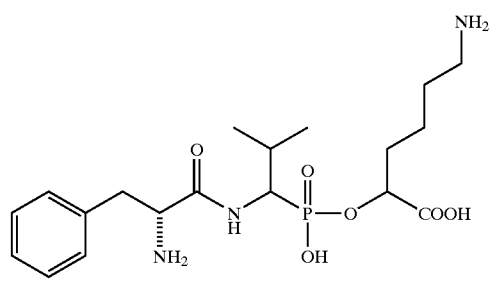 |
| 45 | 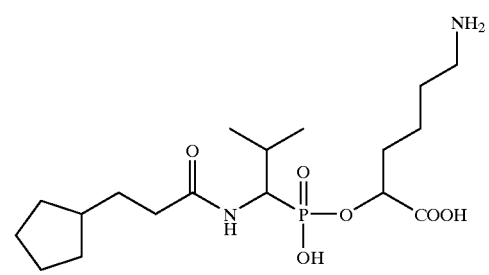 |
| 46 | 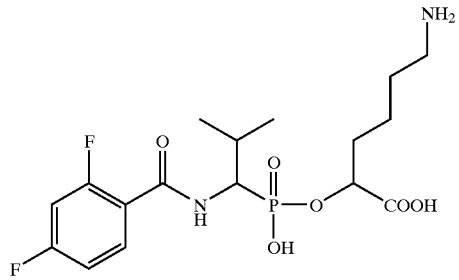 |
| 47 | 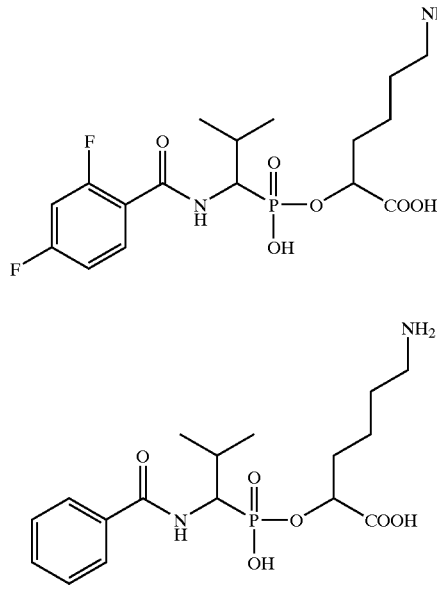 |

-continued
| Example No. | Chemical structure |
|---|---|
| 48 | 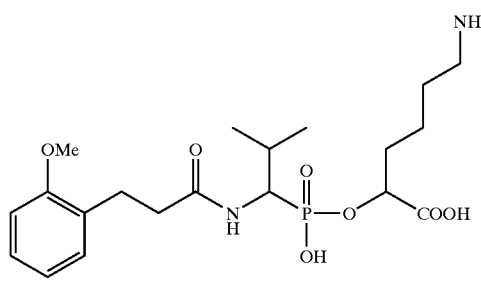 |
| 49 | 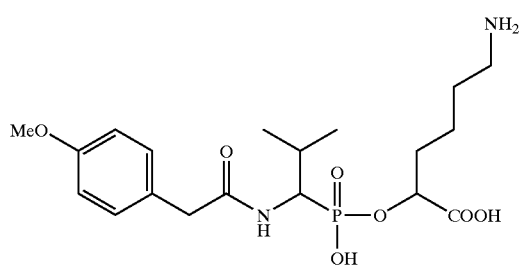 |
| 50 | 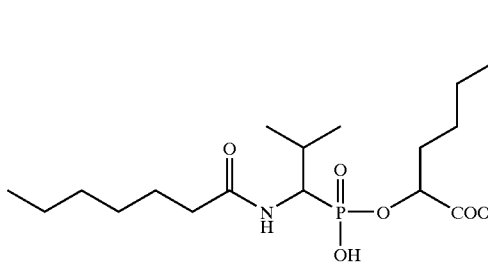 |
| 51 | 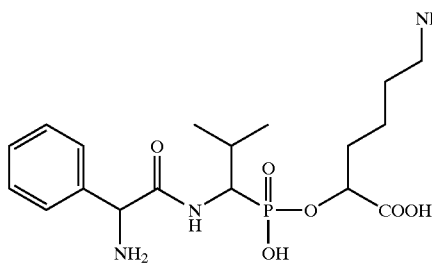 |
| 52 | 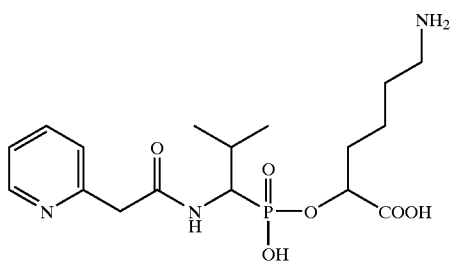 |
-continued
| Example No. | Chemical structure |
|---|---|
| 53 | 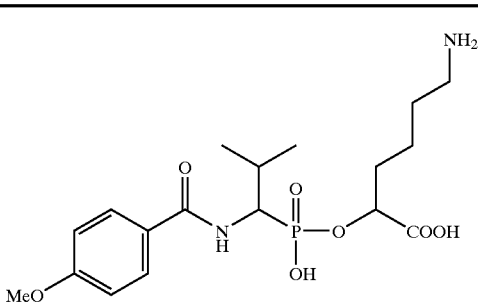 |
| 54 | 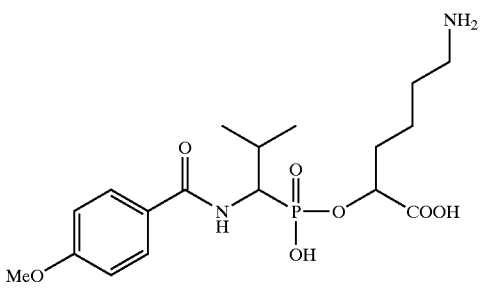 |
| 55 | 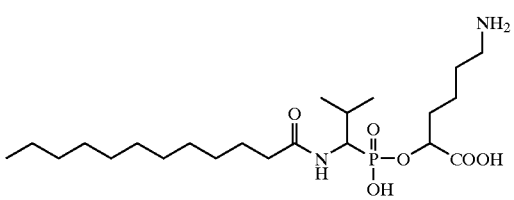 |
| 56 | 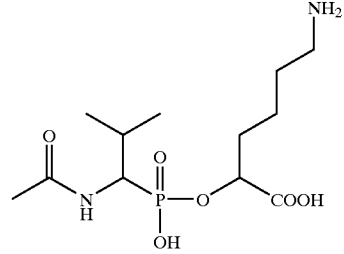 |
| 57 | 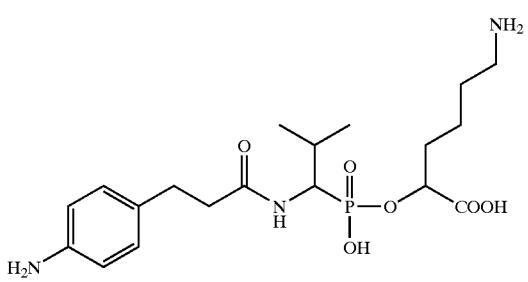 |

-continued
| Example No. | Chemical structure |
|---|---|
| 58 | 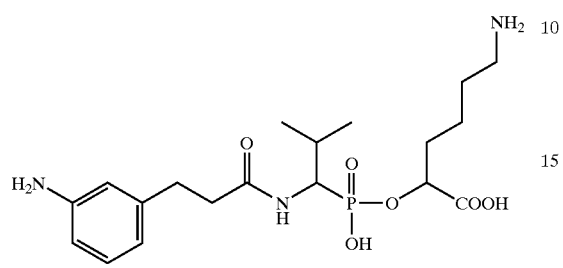 |
| 59 | 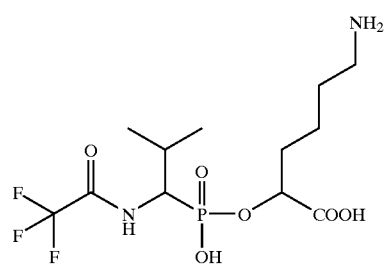 |
| 60 | 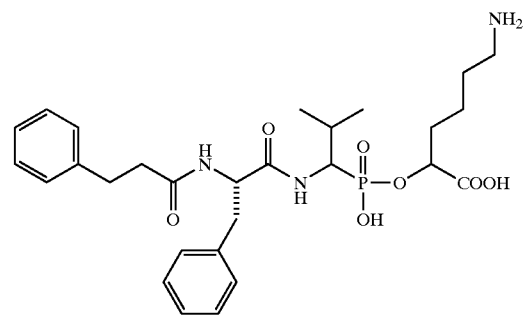 |
| 61 | 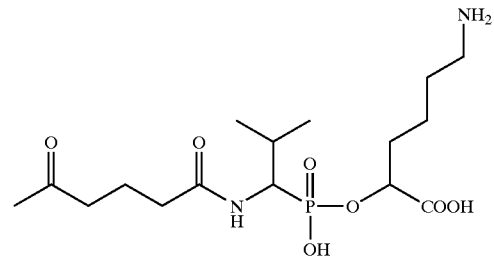 |
| 62 | 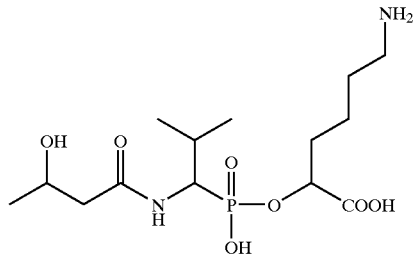 |
-continued
| Example No. | Chemical structure |
|---|---|
| 63 | 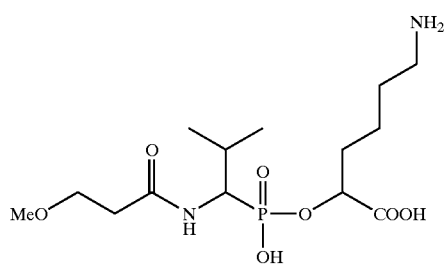 |
| 64 | 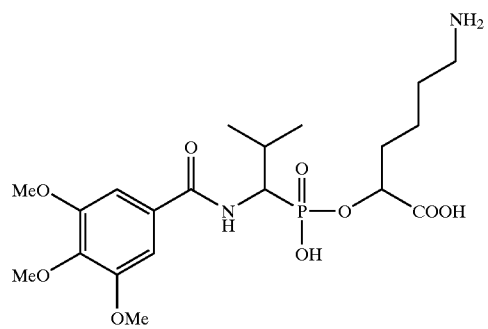 |
| 65 | 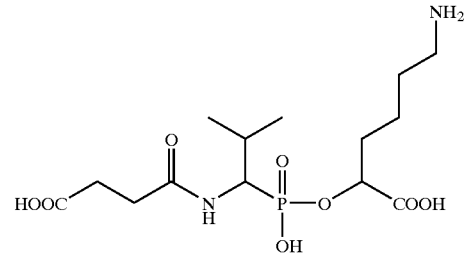 |
| 66 | 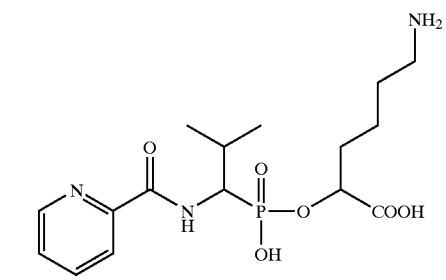 |
| 67 | 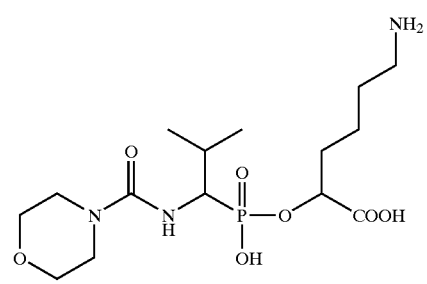 |

| Example No. | Chemical structure |
|---|---|
| 68 | 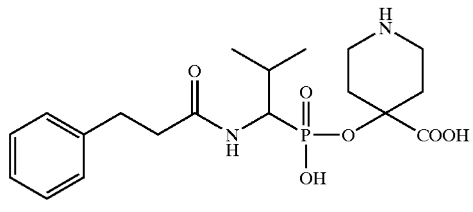 |
| 69 | 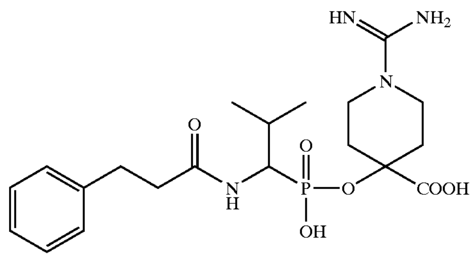 |
| 70 | 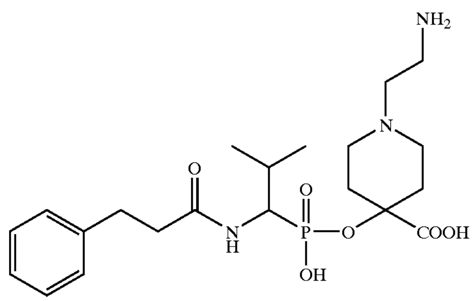 |
| 71 | 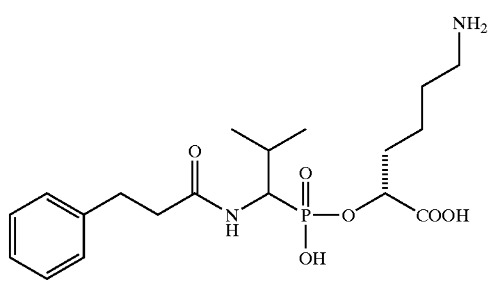 |
| 72 | 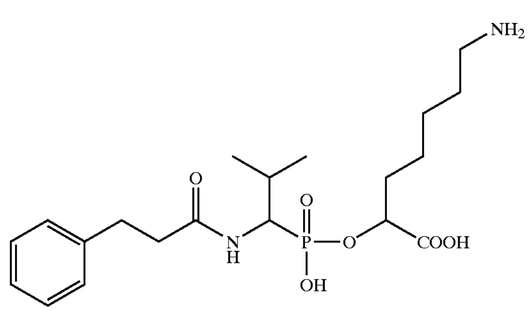 |

| Example No. | Chemical structure |
|---|---|
| 73 | 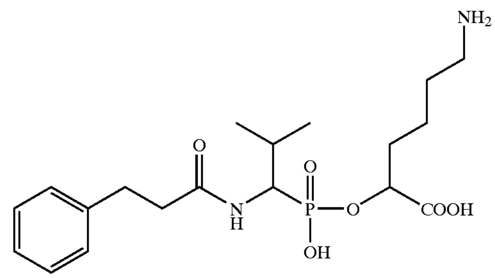 |

Pharmacological Test Example: Inhibitory Activity Against Carboxypeptidase B

Inhibitory activity of the compounds of the present invention against carboxypeptidase B was measured as follows according to the method described in Thromb. Haemost. 371(1998).

(a) Partial Purification of Carboxypeptidase B Precursor (pro-CPB) from Human Plasma Human plasma collected over citric acid was added with 80 mM barium chloride and treated at 4° C. for 30 minutes. The supernatant obtained by centrifugation at 10,000 rpm for 20 minutes was dialyzed against 20 mM HEPES buffer containing 0.15 M sodium chloride (pH 7.4). Furthermore, protein in the fractions obtained with 30% to 80% ammonium sulfate were partially purified by chromatography using a Q-Sepharose column (elution with 50 mM tris-HCl buffer (pH 7.4) gradually containing sodium chloride to 0.5 M).

(b) Activation of pro-CPB pro-CPB (20 μl) was added with 20 μl of a thrombomodulin solution (Thrombomodulin derived from rabbit lung, American Diagnostia Inc., Product No. #237, dissolved at concentration of 300 ng/ml in buffer A as 50 mM tris-HCl buffer (pH 7.4) supplemented with 0.1% Lubrol, 0.1% BSA and 0.15 M sodium chloride), and treated at 25° C. for 3 minutes. Then, the mixture was added with 20 μl of thrombin (Thrombin derived from human plasma, Sigma, Product No. T8885, dissolved at concentration of 3 u/ml in buffer B as 50 mM Tris-HCl buffer (pH 7.4) supplemented with 0.1% BSA, 0.15 M NaCl and 10 mM calcium chloride) and further treated at 25° C. for 30 minutes for activation(*1).

(c) Measurement of CPB Inhibitory Activity

By using a microplate, 4 μl of the sample was added with a mixed solution of 41 μl of buffer C (0.1 M tris-HCl buffer (pH 7.6)) and 25 μl of a substrate solution (Hip-Arg, Sigma, H2508, dissolved in buffer C at concentration of 4 mM.), and further added with 10 μl of the activated CPB solution (*1), and then the mixture was well mixed and allowed to react at 25° C. for 60 minutes. Then, 100 μl of 0.2 M PIPES buffer (pH 7.5) containing 12.5% Tween was added to the mixture to stop the reaction. After 5 minutes, the mixture was added with 100 μl of a coloring solution (2-methoxyethanol containing 1% cyanuryl chloride) and allowed to stand at room temperature for 15 minutes, and then absorbance was measured at 405 nm by using a microplate reader (Bio Rad Model 3550).

Inhibitory activity against carboxypeptidase B was calculated by using the following equation as an inhibitory rate, wherein A represents absorbance in the absence of a tested substance; B represents absorbance in the presence of a tested substance (500 nM); A' and B' represent the aforementioned absorbances obtained by using non-activated enzyme without and with the tested substance, respectively.

Inhibitory rate (%)=[1−{(B−B')/(A−A')}]×100

The results of the carboxypeptidase B inhibitory rates are shown in Table 1, which were calculated by using the above equation and the results of the measurements in the above experiments for the compounds of the present invention.

TABLE 1

| Compound in Examples | Carboxypeptidase B inhibitory rates by tested substance at 500 nM |
|---|---|
| 1 | 30 |
| 2 | >90 |
| 3 | >90 |
| 4 | >90 |
| 5 | 30 |
| 6 | >90 |
| 8 | >90 |
| 9 | >90 |
| 10 | >90 |
| 12 | >90 |
| 14 | >90 |
| 16 | >90 |
| 19 | >90 |
| 20 | >90 |
| 23 | 50 |
| 24 | >90 |
| 25 | 80 |
| 34 | 40 |
| 35 | >90 |
| 37 | 70 |
| 39 | >90 |
| 40 | 30 |
| 41 | >90 |

Toxicity Test Example by Single Administration

The compound of Example 19 of the present invention was dissolved in saline intravenously administered to 6 individuals of ICR male mice of 5 weeks old. At the dose of 1 g/kg of the compound of Example 19, no death of the mice or severe toxicity was observed.

Formulation Example 1

The compound of Example 19 according to the present invention (25 g) was dissolved in water for injection (450 ml), and the solution was added with sodium hydroxide (1.6 g), and adjusted to 500 ml with water for injection. A filtrate was obtained by treating the solution with a membrane for sterile filtration, and aliquots of 1.0 ml were filled in vials. Lyophilization in a conventional manner gave lyophilized vial preparations containing the compound of Example 19 (50 mg). The preparation obtained can be intravenously administered after the preparation is dissolved in saline, or administered by intravenous drip infusion after the resulting solution is added in saline (100 ml) and the like.

Formulation Example 2

The compound of Example 19 according to the present invention (5 g) was dissolved in water for injection (450 ml), and the solution was added with disodium hydrogenphosphate (2.6 g) and then adjusted to 500 ml with water for injection. A filtrate was obtained by treating the solution with a membrane for sterile filtration, and aliquots of 1.0 ml were filled in vials. Lyophilization in a conventional manner gave lyophilized vial preparations containing the compound of Example 19 (10 mg). The preparation obtained can be intravenously administered after the preparation is dissolved in saline, or administered by intravenous drip infusion after the resulting solution is added in saline (100 ml) and the like.

What is claimed is:

1. A compound represented by the following formula (I) or a pharmacologically acceptable salt thereof, or a hydrate thereof or a solvate thereof:

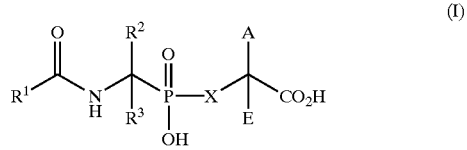

(I)

wherein $R^1$ represents phenylethyl group; $R^2$ represents isopropyl group; $R^3$ represents hydrogen atom; X represents —$CH_2$— or —O—; A represents a group of the following formula (II):

(II)

in which $R^7$ and $R^8$ represent hydrogen atoms; $R^9$ and $R^{10}$ represent hydrogen atoms; m represents 5; and —$(C)_m$— represents a saturated carbon chain, and, E represents hydrogen atom.

2. The compound or the pharmacologically acceptable salt thereof, or the hydrate thereof or the solvate thereof according to claim 1, which is (S)-7-amino-2-((2-methyl-(1R)-(3-phenylpropanoylamino)propyl)(hydroxyphosphinoyl)oxy)heptanoic acid, or 7-amino-2-((2-methyl-1-(3-phenylpropanoylamino)propyl)hydroxyphosphinoyl)-methylheptanoic acid.

3. A medicament composition which comprises as an active ingredient a substance selected from the group consisting of the compound and the pharmacologically acceptable salt thereof, and the hydrate thereof and the solvate thereof according to claim 1.

4. A medicament composition which comprises as an active ingredient a substance selected from the group consisting of the compound and the pharmacologically acceptable salt thereof, and the hydrate thereof and the solvate thereof according to claim 2.

5. A medicament in the form of a pharmaceutical composition which comprises a substance selected from the group consisting of the compound and the pharmacologically acceptable salt thereof, and the hydrate and the solvate thereof according to claim 1 together with a pharmacologically acceptable carrier.

6. A medicament in the form of a pharmaceutical composition which comprises a substance selected from the group consisting of the compound and the pharmacologically acceptable salt thereof, and the hydrate and the solvate thereof according to claim 2 together with a pharmacologically acceptable carrier.

7. The medicament composition according to claim 3 which is used for therapeutic and/or preventive treatment of a thrombotic disease.

8. The medicament composition according to claim 4 which is used for therapeutic and/or preventive treatment of a thrombotic disease.

9. The medicament according to claim 5 which is used for therapeutic and/or preventive treatment of a thrombotic disease.

10. The medicament according to claim 6 which is used for therapeutic and/or preventive treatment of a thrombotic disease.

11. An inhibitor composition against carboxypeptidase B which comprises a substance selected from the group consisting of the compound and the pharmacologically acceptable salt thereof, and the hydrate thereof and the solvate thereof according to claim 1.

12. An inhibitor composition against carboxypeptidase B which comprises a substance selected from the group consisting of the compound and the pharmacologically acceptable salt thereof, and the hydrate thereof and the solvate thereof according to claim 2.

13. A method for therapeutic treatment of a thrombotic disease which comprises administering to a mammal a therapeutically effective amount of a substance selected from the group consisting of the compound and the pharmacologically acceptable salt thereof, and the hydrate thereof and the solvate thereof according to claim 1.

14. A method for therapeutic treatment of a thrombotic disease which comprises administering to a mammal a therapeutically effective amount of a substance selected from the group consisting of the compound and the pharmacologically acceptable salt thereof, and the hydrate thereof and the solvate thereof according to claim 2.

15. A method for preventive treatment of a thrombotic disease which comprises administering to a mammal a preventively effective amount of a substance selected from the group consisting of the compound and the pharmacologically acceptable salt thereof, and the hydrate thereof and the solvate thereof according to claim 1.

16. A method for preventive treatment of a thrombotic disease which comprises administering to a mammal a preventively effective amount of a substance selected from the group consisting of the compound and the pharmacologically acceptable salt thereof, and the hydrate thereof and the solvate thereof according to claim 2.

17. The method according to claim 13, wherein the mammal is a human.

18. The method according to claim 14, wherein the mammal is a human.

19. The method according to claim 15, wherein the mammal is a human.

20. The method according to claim 16, wherein the mammal is a human.

* * * * *